(12) United States Patent
Cassuto

(10) Patent No.:   US 12,577,618 B2
(45) Date of Patent:   Mar. 17, 2026

(54) METHOD FOR SELECTING SPERMATOZOA, IN PARTICULAR FOR MEDICALLY ASSISTED PROCREATION (MAP)

(71) Applicant: Nino Guy Cassuto, Boulogne (FR)

(72) Inventor: Nino Guy Cassuto, Boulogne (FR)

(73) Assignee: Nino Guy Cassuto, Boulogne (FR)

( * ) Notice: Subject to any disclaimer, the term of this patent is extended or adjusted under 35 U.S.C. 154(b) by 824 days.

(21) Appl. No.: 17/759,833

(22) PCT Filed: Jan. 28, 2021

(86) PCT No.: PCT/EP2021/052041
§ 371 (c)(1),
(2) Date: Jul. 29, 2022

(87) PCT Pub. No.: WO2021/152051
PCT Pub. Date: Aug. 5, 2021

(65) Prior Publication Data
US 2023/0077900 A1   Mar. 16, 2023

(30) Foreign Application Priority Data
Jan. 30, 2020   (EP) ..................................... 20305084

(51) Int. Cl.
| | |
|---|---|
| *C12Q 1/68* | (2018.01) |
| *C12P 19/34* | (2006.01) |
| *C12Q 1/686* | (2018.01) |
| *C12Q 1/6883* | (2018.01) |

(52) U.S. Cl.
CPC .......... *C12Q 1/6883* (2013.01); *C12Q 1/686* (2013.01); *C12Q 2600/124* (2013.01); *C12Q 2600/158* (2013.01)

(58) Field of Classification Search
CPC .................. C12Q 1/6883; C12Q 1/686; C12Q 2600/124; C12Q 2600/158
See application file for complete search history.

(56) References Cited

FOREIGN PATENT DOCUMENTS

EP        2532757 A1    12/2012

OTHER PUBLICATIONS

Vivian G. Cheung, et al. "Natural variation in human gene expression assessed in lymphoblastoid cells" Nature Genetics, vol. 33, Mar. 2003, pp. 422-425. (Year: 2003).*
Ronald A. Thisted "What is a P-value?" (May 25, 1998) from— https://galton.uchicago.edu/~thisted/Distribute/pvalue.pdf, pp. 1-6 (Year: 1998).*
H. Juppner "Functional Properties of the PTH/PTHrP Receptor" Bone vol. 17, No. 2, Supplement, Aug. 1995:39S-42S. (Year: 1995).*
Bonache et al, "Sperm gene expression profile is related to pregnancy rate after insemination and is predictive of low fecundity in normozoospermic men", Human Reproduction, vol. 27, No. 6, Jun. 1, 2012, p. 1556-1567.
Johnson et al, "Novel localization of Aurora A kinase in mouse testis suggests multiple roles in spermatogenesis", Jun. 6, 2018, vol. 503, No. 1, p. 51-55.
Nguyen et al, "Gene expression alterations in cryptorchid males using spermatozoal microarray analysis", Jul. 1, 2009, vol. 92, No. 1, p. 182-187.
Leonard et al, "The Aurora A-HP1 gamma pathway regulates gene expression and mitosis in cells from the sperm lineage", BMC Developmental Biology, Biomed Central Ltd., London, GB, vol. 15, No. 1, May 29, 2015, p. 23-33.
Cassuto et al, "A new real-time morphology classification for human spermatozoa: a link for fertilization and improved embryo quality", Jul. 1, 2009, vol. 92, No. 5, p. 1616-1625.
International Search Report and Written Opinion mailed, Apr. 28, 2021, for PCT/EP2021/052041.

* cited by examiner

*Primary Examiner* — Stephen T Kapushoc
(74) *Attorney, Agent, or Firm* — ArentFox Schiff LLP

(57)          ABSTRACT

The present invention relates to a method for analysing a spermatozoon, comprising a step of extracting the nucleic acids from the spermatozoa contained in a first sample of spermatozoa previously obtained from a human subject; a step of measuring the level of expression of at least one marker gene chosen from the group consisting of AURKA, CFAP46, CCDC60, CCDC88B, HDAC4, CACNA1C, CACNA1H, CARHSP1, DNAH2 and SPATA18 from the extracted nucleic acids; and a step of determining the existence of an expression differential of the at least one marker gene in relation to a control. It also relates to a method for selecting spermatozoa and a method for evaluating the quality of a sperm.

7 Claims, 1 Drawing Sheet
Specification includes a Sequence Listing.

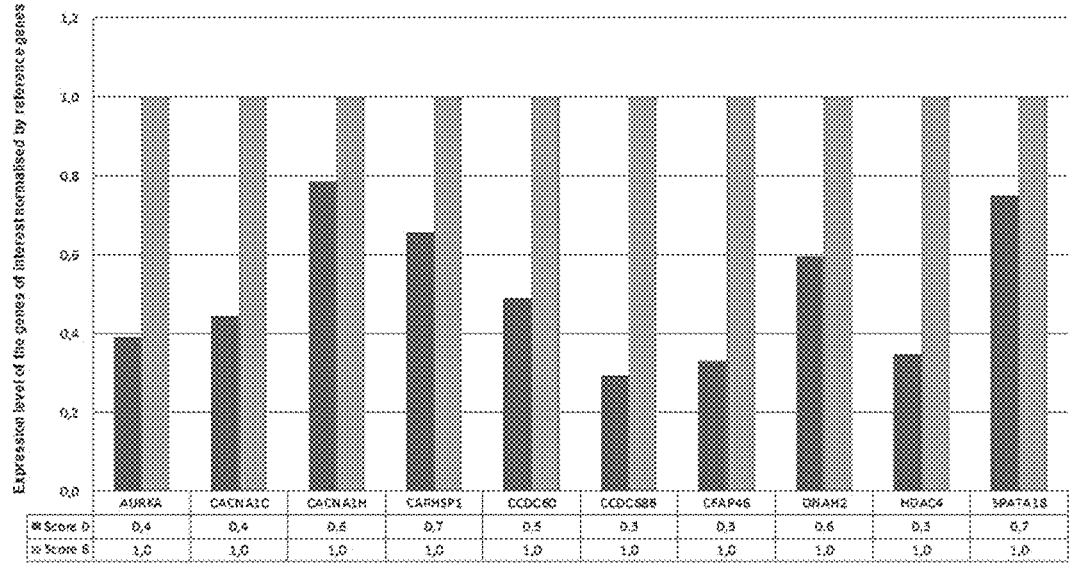

METHOD FOR SELECTING SPERMATOZOA, IN PARTICULAR FOR MEDICALLY ASSISTED PROCREATION (MAP)

CROSS-REFERENCE TO RELATED APPLICATIONS

This application is a National Phase of PCT/EP2021/052041, filed on Jan. 28, 2021, which claims priority to EP Application No. 20305084.4, filed on Jan. 30, 2020, the disclosures of which are hereby incorporated by reference in their entireties.

BACKGROUND

Medically Assisted Procreation (MAP) or Assisted Reproduction (ART) is the set of medical techniques and treatments designed to achieve pregnancy and the birth of a healthy child.

There are male, female and mixed infertilities (when both partners are involved).

A couple is considered hypofertile if they are unable to conceive after 12 months of unprotected sex.

In some cases, this inability to conceive is linked to a deterioration in sperm quality, an ovulation disorder or a mechanical problem in the woman. Sometimes infertility remains unexplained.

In practice, MAP includes many techniques, such as sperm or ovum freezing, artificial insemination (or AIH, a simple and inexpensive technique), in vitro fertilisation (or IVF).

Conventional IVF is the first in vitro technique for achieving pregnancy. It consists, on the day of the oocyte pick-up (D0), in bringing together spermatozoa and oocytes to obtain fertilisation on D1 and then an embryo from D2. The embryos obtained are then transferred into the uterus by means of a catheter under ultrasound control, two, three or five days after fertilisation.

There is a technique more particularly recommended for male infertility or after a failure in classic IVF. It consists in injecting a spermatozoon directly into the oocyte under a microscope.

In vitro fertilisation by ICSI ("IntraCytoplasmic Sperm Injection") now accounts for more than two thirds of IVFs and has a very good success rate. This technique is based on the selection of the "right" spermatozoon to be injected.

This selection involves the identification of morphological indicators capable of signalling the defectiveness of a spermatozoon. IMSI (for "Intracytoplasmic Morphologically Selected Sperm Injection"), for example, is an in vitro fertilisation technique in which the selection of the spermatozoon intended to be micro-injected is carried out by examining its morphology at high magnification (more than ×6000 compared to a magnification of ×400 during an ICSI). Indeed, it allows spermatozoa whose altered morphology is not detectable at ×400 magnification ("low magnification") not to be selected for injection. This technique is more efficient than ICSI for altered sperm.

SUMMARY

The main drawback of spermatozoon selection at high magnification is the time factor, as it takes between one and three hours depending on the sperm sample to select the "right" spermatozoa. Furthermore, as the evaluation is carried out by a biologist, there is also a human factor, as there is some subjectivity in the evaluation. As a result, this selection technique remains time-consuming and relatively expensive, and its indications are poorly defined. However, in some indications of male infertility, this technique not only allows a better pregnancy rate but also a reduction of major malformations in the foetus.

The work of the inventors has aimed to overcome the above drawbacks by providing a method for selecting spermatozoa which makes it possible to define the indications in which the identification of the spermatozoon to be injected has to be carried out at high magnification.

The invention therefore relates to a method for analysing a spermatozoon, comprising the following steps:
    a) extracting nucleic acids from spermatozoa contained in a first spermatozoa sample previously obtained from a human subject;
    b) measuring the expression level of at least one marker gene selected from the group consisting of AURKA, CFAP46, CCDC60, CCDC881, HDAC4, CACNA1C, CACNA1H, CARHSP1, DNAH2 and SPATA18 or a homologous gene thereof, from the extracted nucleic acids; and
    c) determining the existence of an expression differential of the at least one marker gene compared to a control.

DETAILED DESCRIPTION

A spermatozoon is a male reproductive cell, comprising a head (including the nucleus) and a means of locomotion called the flagellum.

"Nucleic acid" refers to DNA, RNA, coding or non-coding nucleic sequences.

The determination of the expression level of the gene can be performed by any method known to the skilled person.

Preferably, the sperm and spermatozoa samples used in the methods according to the invention are samples prepared by double density gradient centrifugation. Such a method is further detailed in Example 2.

By "homologous" it is meant a polynucleotide sequence having a degree of identity of at least 90%, preferably at least 95%, and even more preferably 99% with the wild-type (full length) gene sequence. The degree of identity refers to a sequence identity between two sequences. The identity can be determined by comparing a position in each sequence that can be aligned for comparison. When an equivalent position in the compared sequences is occupied by the same base, then the molecules are identical at that position. Various alignment algorithms and/or programmes can be used for the determination of the homology of two sequences, including FASTA and BLAST.

Preferably, the at least one marker gene is selected from the group consisting of AURKA, CFAP46, CCDC60, CCDC88B, HDAC4, CACNA1C, CACNA1H, CARHSP1, DNAH2 and SPATA18.

More preferably, the at least one marker gene is AURKA or a homologous gene thereof, even more preferably AURKA.

The invention is also directed to a method for selecting a spermatozoon, comprising the analysis method according to the invention, followed by the following step:
    d) selecting the spermatozoon from a second spermatozoa sample previously obtained from a human subject: if there is an expression differential, the selection of the spermatozoon is carried out by observation at a magnification greater than ×5000; if there is no expression differential, the selection of the spermatozoon is carried out by observation at a magnification less than ×500.

The selection method according to the invention is an in vitro method. It allows the selection of a spermatozoon capable of fertilizing an ovum, that is, a mobile spermatozoon with little or no alteration of its morphology.

Such a spermatozoon has a score of 5 or 6 according to the HVB classification (also known as the Cassuto Barak classification, see in particular the article "A new real-time morphology classification for human spermatozoa: a link for fertilization and improved embryo quality" by NG Cassuto et al, Fertility and Sterility, Vol. 92, No. 5, pages 1616-1625, November 2009).

The HVB score corresponds to the evaluation and classification of the morphology of the sperm head at high optical magnification (such as ×6100) and takes into account three elements of the sperm head: the shape of the head (H=Head), the presence of a vacuole in the nucleus (V=Vacuole) and the base of the head (B=Base).

The formula for determining the score is as follows:
+2 points for a head normal in size and shape, according to WHO criteria (World Health Organization, "Laboratory manual for the examination of human semen and sperm-cervical mucus interaction", 4th ed. Cambridge: Cambridge University Press, 1999). In other words, by "head normal in size and shape" it is meant an oval-shaped head with a regular outline; length 3 to 5 mm, width 2 to 3 mm;
+3 points for a head without a vacuole, and
+1 point for a base that is normal in size and shape, that is, it is in line with the oval of the head.

High scoring spermatozoa, score 5 and 6, have normal morphology while low scoring spermatozoa (score 0) are characterised by abnormal head and base morphology in size and shape and the presence of at least one vacuole.

The spermatozoa sample(s) may be from ejaculate previously obtained from a human subject. The human subject is preferably a man suffering from infertility or inability to conceive a child, such as for example a man suffering from partial obstructive azoospermia, oligozoospermia, asthenozoospermia and/or teratozoospermia or any other indications resulting in infertility or inability to conceive a child.

More particularly, in step d), the selection is carried out "by observation", that is, by optical or photonic microscopy.

By "magnification" it is meant the magnification of the optical apparatus (microscope) used to perform the observation. It is obtained by multiplying the individual magnifications of the various elements of the optical apparatus (objective, eyepiece, zoom, etc.). It is denoted as "xY", with Y the magnification used.

Preferably, when the selection is performed at a magnification greater than ×5000, this magnification is preferably greater than ×5500, more preferably greater than ×6000, such as ×6100 or ×6300.

The magnification greater than ×5000 is generally obtained with an objective (×100), an eyepiece (×10), a lens providing a first magnification (×1.5) and then a zoom whose magnification makes it possible to obtain the desired final magnification.

Preferably, the objective is an oil immersion objective.

Preferably, when the selection is performed at a magnification greater than ×5000, it is performed with an inverted microscope equipped with Nomarski interference contrast optic.

An inverted microscope is an optical microscope in which the sample is illuminated from above and observed from below.

By "Nomarski interference contrast optic" it is meant an optic with differential interference contrast (DIC). It is a technique used in microscopy, both reflection and transmission microscopy, to reveal contrasts in microscopic objects without specific staining or preparation, similar to phase contrast.

Preferably, when the selection is performed at a magnification lower than ×500, this magnification is preferably lower than ×450, such as for example, ×200 to ×400.

Preferably, when the selection is performed at a magnification lower than ×500, it is performed with a simple inverted microscope, such as for example provided with an objective (×40) and an eyepiece (×10).

The invention is also directed to a method for evaluating the quality of a sperm, comprising the analysis method according to the invention, followed by the following step:
e) if an expression differential is established in step c), then the sperm comprises at least 90% of spermatozoa with altered morphology; if no expression differential is established in step c), then the sperm comprises at least 5% of spermatozoa with unaltered morphology.

By "spermatozoon with altered morphology", it is meant a spermatozoon with a score of 0 according to the HVB classification.

By "spermatozoon with unaltered morphology", it is meant a spermatozoon with a score of 5 or 6 according to the HVB classification.

Preferably, if no expression differential is established in step c), then the sperm comprises at least 5% of spermatozoa with unaltered morphology and less than 50% of spermatozoa with altered morphology.

Advantageously, in the methods according to the invention, in step b), the expression level of the marker gene(s) is measured by the level of transcription of the RNA or cDNA of said gene.

Preferably, the expression level is measured by PCR amplification of nucleic acids, even more preferably by the number of cycle(s) (Cp) by real-time PCR.

Advantageously, in the methods according to the invention, in step b), in addition to the expression level of the at least one gene, the expression level of at least one reference gene is performed.

By "reference gene" it is meant a gene whose expression level does not vary between a spermatozoon of score 0 and a spermatozoon of score 6.

Preferably, the reference gene is chosen from B2M, PRM1.

Preferably, the measurement of the expression level of at least two reference genes is performed, more preferably B2M and/or PRM1.

Advantageously, the average expression level (Cp) of the two reference genes is calculated as follows:

$$\text{GRs Average } Cp=\tfrac{1}{2}\times(\text{B2M Average } Cp+\text{PRM1Average } Cp)$$

By measuring the reference gene(s), a normalised expression level is obtained. Preferably, the normalization of the expression level (Cp) of the marker gene measured in step b) with respect to an expression level of the at least one reference gene is performed according to:

$$\Delta Cp_{GM}=[Cp_{GM}]-[Cp_{GR}]$$

Where GM represents the marker gene and GR represents the at least one reference gene.

Preferably, the control in step c) is the expression level of the at least one marker gene, measured in a spermatozoa sample with unaltered morphology.

The control can be determined by the same method as the expression level of the marker gene, preferably by PCR, even more preferably by the number of cycle(s) (Cp) by real-time PCR.

Advantageously, for each marker gene, the control is given by the following ΔCpGM control value:

TABLE 1

| Control ΔCp values for each gene | |
| --- | --- |
| | $[\Delta Cp_{GM}]_{control}$ |
| AURKA | 8.83 |
| CACNA1C | 11.05 |
| CACNA1H | 6.84 |
| CARHSP1 | 1.04 |
| CCDC60 | 7.42 |
| CCDC88B | 10.61 |
| CFAP46 | 9.55 |
| DNAH2 | 8.78 |
| HDAC4 | 9.73 |
| SPATA18 | 3.33 |

Preferably, the differential between the expression level of the marker gene from the nucleic acids extracted from the spermatozoa sample previously obtained from a human subject and the control, is a subexpression of the marker gene.

Advantageously, in step b), the measurement of the expression level (Cp) of each gene is performed by quantitative real-time PCR (qPCR); and in step c), for a marker gene, the expression differential is calculated according to the following steps:

i) normalizing the expression level (Cp) of the marker gene measured in step b) to an expression level of a reference gene according to $$\Delta Cp_{GM}=[Cp_{GM}]-[Cp_{GR}]$$

where GM represents the marker gene and GR represents the reference gene; and then ii) determining the expression differential $\Delta\Delta Cp_{GM}$ according to $$\Delta\Delta Cp_{GM}=[\Delta Cp_{GM}]-[\Delta Cp_{GM}]_{control}$$

By "each gene" it is meant in particular:

a marker gene from the nucleic acids extracted from the spermatozoa sample previously obtained from a human subject, at least one reference gene.

Advantageously, in step b), for each gene, the expression level is an average expression level obtained from an average of at least two measurements of expression level (Cp).

As an example, the average Cp for each gene can be calculated according to $$\text{Average } Cp = \frac{1}{n}\sum_{i=1}^{n}(Cp)$$

With n the number of measurement(s) of Cp for a given gene, n being greater than or equal to 2, preferably between 2 and 4, more preferably 3.

In the present application, the ranges of values are understood to include the limits.

Advantageously, in step b), the expression level of a reference gene is:

the average expression level of said reference gene, or an average expression level of the reference genes calculated according to $$GRs \text{ Average } Cp = \frac{1}{k}\sum_{i=1}^{k}(GRi \text{ average } Cp)$$

When the expression level of k reference genes is measured, k being greater than or equal to 2.

Preferably, k is equal to 2.

Preferably, and as indicated above, the measurement of the expression level of at least two reference genes is performed, more preferably, the measurement of the expression level of the reference genes B2M and PRM1.

In this case, the average expression level of the reference genes B2M and PRM1 is calculated as follows:

$$GRs \text{ Average } Cp=\frac{1}{2}\times(B2M \text{ Average } Cp+PRM1 \text{ Average } Cp)$$

Advantageously, the existence of an expression differential is established when an expression differential of at least 10% is determined between the expression level of the at least one gene extracted from the spermatozoa sample and the control.

Preferably, the differential is at least 12%, more preferably at least 15%.

Advantageously, in the methods according to the invention, the expression level of at least two genes, advantageously 5, and preferably 10 genes, is measured in step c).

By at least two genes, it is targeted AURKA and CFAP46, AURKA and CCDC60, AURKA and CCDC88B, AURKA and HDAC4, AURKA and CACNA1C, AURKA and CACNA1H, AURKA and CARHSP1, AURKA and DNAH2, AURKA and SPATA18, CFAP46 and CCDC60, CFAP46 and CCDC88B, CFAP46 and HDAC4, CFAP46 and CACNA1C, CFAP46 and CACNA1 H, CFAP46 and CARHSP1, CFAP46 and DNAH2, CFAP46 and SPATA18, CCDC60 and CCDC88B, CCDC60 and HDAC4, CCDC60 and CACNA1C, CCDC60 and CACNA1H, CCDC60 and CARHSP1, CCDC60 and DNAH2, CCDC60 and SPATA18, CCDC88B and HDAC4, CCDC88B and CACNA1C, CCDC88B and CACNA1H, CCDC88B and CARHSP1, CCDC88B and DNAH2, CCDC88B and SPATA18, HDAC4 and CACNA1C, HDAC4 and CACNA1H, HDAC4 and CARHSP1, HDAC4 and DNAH2, HDAC4 and SPATA18, CACNA1C and CACNA1H, CACNA1C and CARHSP1, CACNA1C and DNAH2, CACNA1C and SPATA18, CACNA1H and CARHSP1, CACNA1H and DNAH2, CACNA1H and SPATA18, CARHSP1 and DNAH2, CARHSP1 and SPATA18, DNAH2 and SPATA18, preferably AURKA and CFAP46.

By at least five genes, it is preferably targeted AURKA, CFAP46, CCDC60, HDAC4 and CCDC88B.

By at least ten genes, it is preferably targeted AURKA, CFAP46, CCDC60, HDAC4, CCDC88B, CACNA1C, CACNA1H, CARHSP1, DNAH2 and SPATA18.

If the method highlights both the existence of differentials for one or more genes and the absence of differentials for one or more genes, then the analysis will be considered insignificant.

Finally, the invention is directed to the in vitro use of at least one gene selected from the group consisting of the AURKA, CFAP46, CCDC60, CCDC88B, HDAC4, CACNA1C, CACNA1 H, CARHSP1, DNAH2 and SPATA18 genes or homologous genes, or of the combination of the 10 genes or homologous genes, for the determination of the method of visual selection of a spermatozoon.

It is also directed to the in vitro use of at least one gene selected from the group consisting of AURKA, CFAP46, CCDC60, CCDC88B, HDAC4, CACNA1C, CACNA1H, CARHSP1, DNAH2 and SPATA18 or homologous genes, or the combination of the 10 genes or homologous genes, for the determination of sperm quality.

The present invention is illustrated, in a non-limiting manner, by the following examples and the following FIGURE:

FIG. 1 represents a histogram of the expression level of the genes of interest AURKA, CFAP46, CCDC60, CCDC88B, HDAC4, CACNA1C, CACNA1 H, CARHSP1, DNAH2 and SPATA18. Their expression levels are normalised by two reference (invariant) genes, PRM1 and B2M. The graph represents the ratio of the expression level of these genes of interest for spermatozoa of sample score 0 to the expression level of these same genes for spermatozoa of sample score 6.

EXAMPLE 1: IDENTIFICATION OF A CORRELATION BETWEEN THE MORPHOLOGY OF SPERMATOZOA AND THE EXPRESSION OF A SET OF GENES

1.1 Description of the Study

The aim was to measure the relative expression of genes by qPCR, using 10 human sperm samples divided into 2 groups, with HVB scores for sperm quality of 0 and 6 respectively.

This study selected 12 genes (10 genes of interest and 2 reference genes). Expression profiles of the genes were measured by real-time PCR for all 10 (2 groups of 5) men.

Sperm samples from the 10 men collected by masturbation, prepared by double density gradient centrifugation and packed in Qiazol reagent were received and stored at −80° C. Tubes were identified by their "tube no."; these unique identifiers were used throughout the process to ensure the confidentiality of the donor's personal data.

TABLE 2

| | Sperm scores | | |
|---|---|---|---|
| Donor | Sperm sample tube no. | HVB Scores* | Sample score** |
| 1 | 01 | 0/10/90 | 0 |
| 2 | 02 | 10/65/25 | 6 |
| 3 | 03 | 0/10/90 | 0 |
| 4 | 04 | 0/10/90 | 0 |
| 5 | 05 | 0/10/90 | 0 |
| 6 | 06 | 15/65/20 | 6 |
| 7 | 07 | 5/65/30 | 6 |
| 8 | 08 | 10/60/30 | 6 |
| 9 | 09 | 10/60/30 | 6 |
| 10 | 10 | 0/10/90 | 0 |

*HVB scores for a sperm sample are presented as follows: % spermatozoa with score 6-5/% spermatozoa with score 4-3-2-1/% spermatozoa with score 0.
**The sample score was assigned as follows:
Sperm from men with a sample score of 0 has at least 90% spermatozoa with a score of 0.
Sperm from men with a sample score of 6 has at least 5% of spermatozoa with a score of 5 and 6 and less than 50% of spermatozoa with a score of 0, preferably less than 30%.

The genes studied are as follows:

TABLE 3

| Genes studied | |
|---|---|
| Gene of interest (GI) | Gene name |
| SPATA18 | spermatogenesis associated 18 |
| CCDC60 | coiled-coil domain containing 60 |
| CACNA1H | calcium voltage-gated channel subunit alpha1 H |
| CCDC88B | coiled-coil domain containing 88B |
| DNAH2 | dynein axonemal heavy chain 2 |
| CACNA1C | calcium voltage-gated channel subunit alpha1 C |
| CARHSP1 | calcium regulated heat stable protein 1 |
| HDAC4 | histone deacetylase 4 |
| CFAP46 | cilia and flagella associated protein 46 |
| AURKA | aurora kinase A |

1.2 Sample Processing: RNA Preparation

RNA extraction of the 10 samples was performed using the miRNeasy Kit (QIAGEN) following the manufacturer's protocol. In short, each sperm sample was lysed in 700 μL of QIAzol® lysis reagent in a 2 mL SafeLock microcentrifuge tube containing a 5 mm stainless bead. Each sample was then ground using the Qiagen TissueLyzer for 2×2 minutes at 20 Hz. The homogenate was incubated on the work surface at room temperature (15-25° C.) for 5 min. 140 μL of chloroform was added to the homogenate to seal the tube. The tube was shaken vigorously for 15 seconds and placed back on the work surface for another 2-3 min. The lysate was centrifuged at 12,000×g for 15 min at 4° C. in a microcentrifuge. The upper aqueous phase (approximately 350 μL) was carefully transferred to a clean 2 mL microcentrifuge. The rest of the procedure was performed following the manufacturer's protocol on an automated workstation (QIAcube-QIAGEN), according to the pre-installed protocol, in order to optimise reproducibility and normalisation of miRNA extraction. At the end of the procedure, each RNA was eluted in 30 μL of ultra-pure $H_2O$. A 3 μL aliquot part was pipetted into a new centrifuge tube for quality validation and all tubes were immediately stored in an ultra-low temperature freezer (−80° C.). Thus 10 RNA samples are obtained.

1.3 Analysis of Relative Expression of the Genes

1.3.1 Preparation of cDNA Models

The cDNA models were prepared using the ReadyScript cDNA synthesis kit (Sigma-Aldrich) from 100 ng of total RNA template according to the manufacturer's protocol. The ReadyScript cDNA master mix contains a mixture of random primers and oligo(dT) in a specific ratio to ensure optimal representation of all transcription sequences in the cDNA product. The cDNA synthesis was performed using 96-well plates in a final reaction volume of 20 μL using the C1000 thermal cycler (Bio-Rad) according to the following thermal program: 5 minutes at 25° C., 30 minutes at 42° C., 5 minutes at 85° C.

The cDNA templates were diluted 1/11th in 0.1×TE prior to the qPCR experiments.

1.3.2 Real-Time TaqMan qPCR Experiments

The qPCR experiments were performed using TaqMan gene expression assays (TaqMan Gene Expression Assays, Applied Biosystems) on LightCycler480 (Roche Diagnostics). Genes PRM1 and B2M were used as reference genes (GR).

TABLE 4

List of TaqMan identifiers

| Gene of interest/reference gene | "TaqMan Gene Expression Assay" Identifier |
|---|---|
| SPATA18 | Hs01102818_m1 |
| CCDC60 | Hs00905317_m1 |
| CACNA1H | Hs01103527_m1 |
| CCDC88B | Hs00989955_g1 |
| DNAH2 | Hs01044842_m1 |
| CACNA1C | Hs00167681_m1 |
| CARHSP1 | Hs00183933_m1 |
| HDAC4 | Hs01041648_m1 |
| CFAP46 | Hs00929098_m1 |
| AURKA | Hs01582072_m1 |
| B2M | Hs00187842_m1 |
| PRM1 | Hs00358158_g1 |

All qPCRs were performed using 384-well plates distributed into 3 technical replicates, in a final reaction volume of 10 μL, using TaqMan Fast Advanced Master Mix (2×).

1.3.3 qPCR Programme

The qPCR cycles consisted of 20 seconds at 95° C. for enzyme activation, followed by 45 cycles of 3 seconds for denaturation and 30 seconds for annealing and extension with fluorescence measurement. The qPCRs were performed on the LightCycler 480 platform (Roche). The Roche Diagnostics standard procedure was used to control real-time qPCR equipment. The intensity of the xenon lamp was checked before each analysis.

1.4 Statistical Analyses 1.4.1 Validation of Reference Genes

In order to increase the stability of the qPCR experiment, it is recommended to use several reference genes in order to obtain an average expression stability of the reference genes using the Vandesompele method of M-Values (Hellemans J et al. Genome Bio 2007). In this method, one reference gene is tested against the other reference gene in a pairwise variation excluding the least stable gene from the analysis. The most stable reference gene has the lowest M-values. Reference genes are accepted for a stability such that the M-value crosses the 0.25 threshold. For this experiment, only two reference genes were used: β2-microglobulin (B2M) and protamine 1 (PRM1). The expression of the M-values for these genes was evaluated:

B2M: 0.14

PRM1: 0.16

These values are within a reasonable range of M-values (<0.2), so both genes are strong candidates for reference genes.

1.4.2 Specificity Test Using Negative Controls

This specificity test consists in checking the possible cross-reactivity of the primers during the PCR process. For each gene, two negative controls were used to highlight any primer cross-reactivity, such as homo- or heterodimer formation, PCR contamination, genomic DNA contamination, etc.:

An "NTC" (No Template Control) control which corresponds to a PCR reaction mixture, processed in exactly the same way as other real-time PCR reactions, but in which no cDNA has been added. This control detects any external contamination or other factors that may cause a non-specific increase in fluorescence signal.

A "No RT" (No Reverse Transcriptase Control) control which corresponds to a sample treated in exactly the same way as the other real-time PCR reactions, but in which the cDNA template has been voluntarily replaced by an RNA template.

Each of the 2 tests was performed simultaneously for each of the 12 genes on a 384-well PCR plate. For each gene, the Cp ("Crossing Point") values of the 2 negative "NTC" and "No RT" controls must be within 45 Cp, or 10 Cp higher than the highest Cp value for the corresponding RNA.

The NTC and No RT controls are validated.

1.4.3 Calculations of the Relative Expression Analysis of the 10 Genes of Interest (GI) Between Score 0 and Score 6 Sperms and Results Statistical calculations were performed using Delta.Cp (DCp) values according to the formula described below.

Cp values are given for each GI and GR and for each donor.

The n=3 values are evaluated for each donor, for each GI, GR and according to the formula described below (Livak et al. 2001).

For each donor, the average Cp of each reference gene was calculated as follows: The average Cp for each gene, reference genes (GRs) and genes of interest (GIs), is calculated using the following formula:

$$\text{Average } Cp = \frac{1}{n}\sum_{i=1}^{n}(Cp)$$

The average Cp of the 2 reference genes (GRs), for each donor, was calculated as follows:

GRs Average $Cp = \frac{1}{2} \times (\text{B2M Average } Cp + \text{PRM1 Average } Cp)$ Delta.Cp is calculated for each gene of interest (GI) according to the following formula:

$\Delta Cp_{GI} = [\text{Average } Cp_{GI}] - [\text{Average } Cp \text{ GR}]$

The statistical results are as follows:

TABLE 5

Statistical results of normalised expression levels for each gene

| | ΔCp score 0 Median* | ΔCp score 6 Median** | ΔCp Limit*** |
|---|---|---|---|
| AURKA | 9.50 | 8.16 | 8.83 |
| CACNA1C | 12.03 | 10.07 | 11.05 |
| CACNA1H | 6.95 | 6.74 | 6.84 |
| CARHSP1 | 1.10 | 0.99 | 1.04 |
| CCDC60 | 7.62 | 7.23 | 7.42 |
| CCDC88B | 11.76 | 9.47 | 10.61 |
| CFAP46 | 10.04 | 9.06 | 9.55 |
| DNAH2 | 9.07 | 8.49 | 8.78 |
| HDAC4 | 10.00 | 9.45 | 9.73 |
| SPATA18 | 3.29 | 3.38 | 3.33 |

*Statistical median based on 5 patients with a score sample of 0.
**Statistical median based on 5 patients with a sample score of 6.
***Limits: threshold values.

In order to set forth the results in a comparative diagram, the following calculations were performed:

Delta.Delta.Cp (ΔΔCp) is calculated for each GI according to the following formula:

$\Delta\Delta Cp_{GI} = [\Delta Cp_{GI}]_{Score\ 0} - [\Delta Cp_{GI}]_{score\ 6}$ The ratio is calculated for each GI according to the following formula:

$$\text{Ratio}_{GI} = 2^{-(\Delta\Delta Cp)}$$

To facilitate visualisation of the results, the arbitrary value of 1 is assigned to the score 6 values.

The results show a general trend of subexpression for all 10 genes (blue bar) in a sample marked as having a low HVB score. The results are represented in FIG. 1.

In order to evaluate these preliminary results, for each gene of interest a Mann-Whitney test was used. The table below shows the Pvalues given by this test:

TABLE 6

Values for each gene

| Gene name | Pvalue |
|---|---|
| AURKA | 0.004316 |
| CACNA1C | 0.3057 |
| CACNA1H | 0.6764 |
| CARHSP1 | 0.4697 |
| CCDC60 | 0.09758 |
| CCDC88B | 0.1028 |
| CFAP46 | 0.01651 |
| DNAH2 | 0.1815 |
| HDAC4 | 0.07368 |
| SPATA18 | 0.6764 |

Applying an alpha error of 5%, 2 genes, AURKA and CFAP46 showed a significant Pvalue and 3 genes showed a non-significant but still interesting Pvalue.

The box diagrams in FIG. 1 show the 5 preferred genes to discriminate the two groups of HVB scores.

2. Conclusion

In this study, analysis of the expression level of 12 genes was performed by real-time PCR, using sperm samples taken from 10 men.

This study identified 12 genes as determinants of spermatozoa quality in men.

The expression level of these genes correlates with some precise and well-defined morphology of the living spermatozoon head, which is mobile at high magnification.

EXAMPLE 2: IMPLEMENTATION OF THE METHOD FOR SELECTING A SPERMATOZOON FOR MAP

A first sperm sample previously obtained from a patient is processed as follows:

1. Preparation by Double Density Gradient Centrifugation

Spermatozoa migration was performed with a double-layer gradient.

In one tube, 1 mL of total spermatozoa was prepared on a two-layer concentration gradient of 45% and 90% sperm isolate separation medium and centrifuged at 300 g for 15 min. The supernatant was discarded and the sperm pellet was washed with HAM'S culture medium supplemented with 10% Human Serum Albumin (HSA) and centrifuged at 300 g for 5 min. The final pellet of total migrated spermatozoa was resuspended in 1 mL of HAM'S culture supplemented with 10% HSA.

2. Gene Expression by qPCR

Gene expression by qPCR is performed as follows on the final pellet obtained in the previous step:

Preparation of the RNA as described in section 1.2 above,

Execution of qPCR on the marker gene(s) and reference genes as described in sections 1.3.2 and 1.3.3 above, Calculation of the average Cp for each gene, Calculation of the average Cp GRs for the reference genes B2M and PRM1, Calculation of the $\Delta$Cp for each marker gene and comparison with the control $\Delta$CpGM values (Table 1) in order to evaluate whether there is an expression differential.

If an expression differential ("positive") is highlighted on the basis of the gene expression analysis performed on the first sample, MAP is performed with high magnification selection of spermatozoa in a second sperm sample from the same patient. This will allow the selection of a spermatozoon with a more condensed chromatin, increase the pregnancy rate, decrease major malformations and possibly highlight a genetic factor in male infertility.

If a differential expression ("positive") is not highlighted on the basis of the gene expression analysis performed on the first sample, MAP is performed using the conventional method (low magnification).

Sequences of genes:
>NM_145263.3 Homo sapiens spermatogenesis associated 18 (SPATA18), transcript variant 1, mRNA (SEQ ID NO: 1)

ACCCAGGGCGGGGCGGCGCGGGCGTTGCCACGACGCGGGCCGCGCGCGTCCCTGGCAGCCAACCCGTCCA

CGTCAAGGTTTGTTTAATAATCGCCAGGGTATCTATGGCCGGGCTCAGGCGGCTGCTGGGGAGCCAGGAG

ACCGCGCGGGACGGCGGATGAGGCGCGGCGGCTGCGGCCCAGGGCACCTCCCCTCTGGCTTCCCGAACCC

GGCCAGGTCCGACCCGAGGGGGAGGATGGAAACACCTGCCGCGCTCTGAGCCCCCCAGAAGAGAACACCC

TTCCCGCCATATCACCCCACGGTCCTGCGGAGGCCACCGCCTGGTCCCCCCAAGTCTCCATCGCGCAGCG

TGGGGCCGAGAGGAATAGTGAGCGATGGCGGAAAACCTGAAAAGACTGGTCTCAAACGAAACTTTACGAA

CGTTGCAGGAAAAGCTAGACTTCTGGCTGAAGGAGTACAACACAAACACGTGTGATCAAAATCTAAACCA

TTGCCTTGAACTCATTGAGCAAGTTGCCAAGGTGCAGGGACAACTCTTTGGGATCCTCACAGCAGCAGCC

CAAGAAGGAGGACGTAATGATGGTGTGGAAACAATCAAGTCACGCCTTTTGCCTTGGCTGGAGGCTTCCT

TTACTGCTGCTTCCCTGGGAAAATCTGTTGACAGCAAGGTCCCCTCTCTGCAGGACACGTTTGATAGGGA

GAGACATAAAGATCCCAGTCCTCGGGATCGGGATATGCAACAGTTAGACTCTAATTTGAACTCAACCCGG

AGTCAATGCAACCAGGTTCAAGACGATCTGGTTGAAACTGAAAAGAATCTTGAAGAAAGCAAGAACAGAT

-continued

```
CGGCCATATCCCTTTTGGCTGCAGAGGAGGAAATAAATCAGCTGAAAAAGCAGCTTAAATCTCTTCAAGC

TCAGGAGGATGCCCGCCACAGAAACACAGATCAGAGGAGCTCAGAGAATAGGCGGTCAGAGCCTTGGAGC

TTGGAGGAGCGGAAGCGTGAGCAGTGGAACTCACTCAAGCAGAATGCAGACCAGCAGGACACAGAAGCCA

TGTCCGATTATAAGAAACAGCTCCGAAACCTGAAGGAGGAGATAGCTGTTCTGTCTGCTGAGAAAAGTGC

ACTCCAAGGAAGGTCCTCCAGGAGCCGGTCTCCCAGCCCTGCCCCTCGCAGCCGTAGCTGCAGCCGCAGC

AGATCTGCCAGCCCCTCCACCGCTGTCAAGGTCAGGAGACCGTCCCCAAACCGCTCCAAGCTGTCCAATG

TGGCGCGCAAGGCTGCCCTCTTGTCCCGGTTCAGCGATTCCTATTCCCAGGCCCGCCTGGACGCGCAGTG

CCTGCTGCGGCGCTGCATCGACAAGGCTGAGACCGTTCAGCGGATCATCTACATCGCCACAGTGGAGGCA

TTCCATGTAGCAAAAATGGCATTCAGACACTTCAAGATCCATGTGAGAAATCGTTGACACCATCTTATG

TGGGGTCGAATGACTTTGAGAATGCTGTCTTGGATTATGTCATTTGTCATCTTGATCTATATGATTCTCA

AAGCAGTGTCAATGATGTGATCCGAGCCATGAATGTCAATCCCAAGATTTCATTCCCTCCTGTCGTTGAC

TTTTGCCTTCTCAGTGACTTCATCCAGGAGATATGTTGCATTGCCTTTGCAATGCAGGCCTTAGAACCAC

CCCTAGATATTGCATATGGAGCAGATGGAGAAGTTTTTAATGATTGCAAATACCGCCGCAGCTACGACTC

GGATTTCACTGCTCCCTTAGTCCTCTATCACGTGTGGCCTGCTCTCATGGAGAATGACTGTGTCATTATG

AAGGGAGAAGCTGTCACCAGGAGAGGGGCTTTTTGGAATTCGGTGCGATCTGTAAGTCGTTGTCGAAGCA

GGAGTTTAAGTCCCATTTGCCCCCCGTAGCCAAATTGGTTTAAACACGATGTCTCGAAGTCGGAGTCCTTC

TCCAATAAGATGTGGATTGCCAAGATTTTAAAAGCACCAGACCTGCTCCTTTGACCCAGTGCGTGGAAAC

AGCTGCTTTCTCCAGTGCCGCCATCTGTCTTCTGTGTCTGCCTCAGACCTCACTTAAGATAATGTCAAAA

GGCAATTCTGTGTATCACCCCACACAGAGAGTTAAATGTTTTGGCTTGGCGCATTTGTAACTTTAGATAT

ATTGCATTCTATTTTATTTTATAGATACTAATTCCATTAATTTCATAAAAATGATTGTATAGGCATTTAG

GATCATATTCATTCGAAGCAAAGTCCGTTACAAAGGTTCAAGATTTCCATCTCAAAACACTACGCTCTTT

TATGGGAACTGTGTGAACTGAAGTGGAAAGCATCTACCATGCTGAGGCTAAAAGAAAAGATGAATCATTT

TAGTTTGCAGATGGATCGTAAATATAATTGTTGGTATCAGCTTTAGCTCAAAACCAATATTAGGTGTTTT

AATTTCCTTTTAAGGTTTGGAAGACAGCCCTAATCTCAGGTTGGGGAGCTCATGTTAGTAGCAGTGACTT

AAGGCTAAGTGTAGAAGATAATTTAAGATACATTTTCTTTATATATTAGCCAACAAATTATATTTATTGG

TTGGCTTGCTTTTCCGTTCTGATTTTGAGAGTGCCCAGTTTGGTTTAGTTGACCAATGAATGTCAAAGCT

ACTTAGTTGAGAGAATTTCCTTGTTCATAAATGTAGAGCAGTGATTTGATTAGAAGCCAGCTTTGAGATA

AATGTTAATTACCTCATGCATATCTCCTGGGAATATTTCAAACTGTTTTAATGCATGTGTTATATATAAA

AGTTTCTTGGGACATGCTCTTCACCTGTTCTACCTAGTTATTTGCAAATTCAGACCTCCTATTGAACTCT

GTCTGACCAAAACTACTTAAACTCAAGGCCCAAAACTAGGGGCACCATTTACTGATTTTAAATTGAGTAT

ATATCCCTTGACTTCTTCACTGTCAAATACTTTTGAAACTTCACGTTCAAGATAAGAATGGAATGTTGCT

TTCTTGCAATAAGTAATGTTCTTTCTGCCTTTTTTTCACTTTTAAGTCAGCCTTAAACACATGCCTCACA

AACATCTACTTTCTCCACATACCTTTGAGAGAGACACTGAATTGGCCTCAGCTCAGTTTTGCATAAGCTT

AGTGCCAGAACCAGCACCTGATGCTTTTCAGGTGAAAATAAAACAAACAGCTTCTCTAAAGCATCTTACC

CCTGTGCTGGAGGTTTGAGGGACCTCTTCAGTGCCTGCCCCTTGAGTCTAATGGTCACCACCTCATTCTG

AAGTATGAGTTGAATTTTTTGCCCTCTTTGCATATTTACATTAGTCATCACTTTGAAGCAATGCAGTGTG

CTGGAAGGAGCACTATCTGCCTAGGTAACTGCTAGTCATGACTTGGTCATCAGCTTGCTTTGTGGCACTG

AGCAAGTTACTTCACTTCTCTGAGCCTTGGTTTTATCATAGGGTGAGGAGGTTGGATACAATTAGTGCCC

CTCTTAACCCTGCAGACTCAATGTTCCCTTTTATAACAAGTATTTTATTCTGAATATGAAATGAAAATTA

AAGTTAATATAATCATCTATGTGCATGTATAATTTTAAGCAGTGAACATAGTACCCTAACTATAATATAA
```

-continued

```
AGCAGAAAAAAAGGCAACTTTTAATAAAATAAAATGTATTTCAATAAAAAAGCTTGGGTATAACCACCCT

AGAAGATAAAATTAAGTCATTAGATGGCTGAACCTGCATGTAGAGCCACCAGCTACAAATGAAAATCAAT

GTGTGTATTGGCAACAGAAAATCACGGTGTTGTCATTGGATGTGACTTTCTGAAGTGGTGGGCAATTCTT

GTTAATGTTTTAAACAAAAAAAAAAAAAACCTTACAGTCTTGCCCTGATTTACACAGCAGTCACATTCCTG

GAAAATTCAAGTGTTTATTAAAACTATGCAACAGTTACTGTGTGTTATACGTTGAAAGGTCTTCACTAAT

ATCTCACTAAGTAATGAGAATGCCTACATATCAGAATTTTTTTTTTCAGGAGCCAAGCACATATACTGAT

TTGGAAAAAGGCACAGGTAGCTCAGTTTATTTGCTTTCTACCCTGCCTGGCCACTTGCTGTTTCTTCAGT

TTCTAATTTGAGCTGTAACTACACAAGGAAAGCTAAATAGTCTGGAAAATTTTTGGAAAGAATCCACAAA

GCCAAAGGAGACTGGCCTATACTCATTTTATCTGGGGATGTACCTTACCCTTAGAGACTTTGAAAAATGT

GAAGCTCTTATTTTGTAACCTGGGTAAATGTTAGTTTCTAGATTTTCGGCTTAACATCTAATAATAACAT

TTAAAAAGTGCTTTTGTAACTATTAGTTATTTGCAATAAAATGCTTTCCTTCTACAGTCCCAAGTTCAAA

AAAAAAAAAAAAAA
```

>NM_001297608.1 *Homo sapiens* spermatogenesis associated 18 (SPATA18),
transcript variant 2, mRNA (SEQ ID NO: 2)

```
ACCCAGGGCGGGGCGGCGCGGGCGTTGCCACGACGCGGGCCGCGCGCGTCCCTGGCAGCCAACCCGTCCA

CGTCAAGGTTTGTTTAATAATCGCCAGGGTATCTATGGCCGGGCTCAGGCGGCTGCTGGGGAGCCAGGAG

ACCGCGCGGGACGGCGGATGAGGCGCGGCGGCTGCGCGCCCAGGGCACCTCCCCTCTGGCTTCCCGAACCC

GGCCAGGTCCGACCCGAGGGGGAGGATGGAAACACCTGCCGCGCTCTGAGCCCCCCAGAAGAGAACACCC

TTCCCGCCATATCACCCCACGGTCCTGCGGAGGCCACCGCCTGGTCCCCCCAAGTCTCCATCGCGCAGCG

TGGGGCCGAGAGGAATAGTGAGCGATGGCGGAAAACCTGAAAAGACTGGTCTCAAACGAAACTTTACGAA

CGTTGCAGGAAAAGCTAGACTTCTGGCTGAAGGAGTACAACACAAACACGTGTGATCAAAATCTAAACCA

TTGCCTTGAACTCATTGAGCAAGTTGCCAAGGTGCAGGGACAACTCTTTGGGATCCTCACAGCAGCAGCC

CAAGAAGGAGGACGTAATGATGGTGTGGAAACAATCAAGTCACGCCTTTTGCCTTGGCTGGAGGCTTCCT

TTACTGCTGCTTCCCTGGGAAAATCTGTTGACAGCAAGGTCCCCTCTCTGCAGGACACGTTTGATAGGGA

GAGACATAAAGATCCCAGTCCTCGGGATCGGGATATGCAACAGTTAGACTCTAATTTGAACTCAACCCGG

AGTCAATGCAACCAGGTTCAAGACGAGCTTAAATCTCTTCAAGCTCAGGAGGATGCCCGCCACAGAAACA

CAGATCAGAGGAGCTCAGAGAATAGGCGGTCAGAGCCTTGGAGCTTGGAGGAGCGGAAGCGTGAGCAGTG

GAACTCACTCAAGCAGAATGCAGACCAGCAGGACACAGAAGCCATGTCCGATTATAAGAAACAGCTCCGA

AACCTGAAGGAGGAGATAGCTGTTCTGTCTGCTGAGAAAAGTGCACTCCAAGGAAGGTCCTCCAGGAGCC

GGTCTCCCAGCCCTGCCCCTCGCAGCCGTAGCTGCAGCCGCAGCAGATCTGCCAGCCCCTCCACCGCTGT

CAAGGTCAGGAGACCGTCCCCAAACCGCTCCAAGCTGTCCAATGTGGCGCGCAAGGCTGCCCTCTTGTCC

CGGTTCAGCGATTCCTATTCCCAGGCCCGCCTGGACGCGCAGTGCCTGCTGCGGCGCTGCATCGACAAGG

CTGAGACCGTTCAGCGGATCATCTACATCGCCACAGTGGAGGCATTCCATGTAGCAAAAATGGCATTCAG

ACACTTCAAGATCCATGTGAGAAAATCGTTGACACCATCTTATGTGGGGTCGAATGACTTTGAGAATGCT

GTCTTGGATTATGTCATTTGTCATCTTGATCTATATGATTCTCAAAGCAGTGTCAATGATGTGATCCGAG

CCATGAATGTCAATCCCAAGATTTCATTCCCTCCTGTCGTTGACTTTTGCCTTCTCAGTGACTTCATCCA

GGAGATATGTTGCATTGCCTTTGCAATGCAGGCCTTAGAACCACCCCTAGATATTGCATATGGAGCAGAT

GGGAAGTTTTTAATGATTGCAAATACCGCCGCAGCTACGACTCGGATTTCACTGCTCCCTTAGTCCTCT

ATCACGTGTGGCCTGCTCTCATGGAGAATGACTGTGTCATTATGAAGGGAGAAGCTGTCACCAGGAGAGG

GGCTTTTTGGAATTCGGTGCGATCTGTAAGTCGTTGTCGAAGCAGGAGTTTAAGTCCCATTTGCCCCCGT

AGCCAAATTGGTTTAAACACGATGTCTCGAAGTCGGAGTCCTTCTCCAATAAGATGTGGATTGCCAAGAT
```

-continued

```
TTTAAAAGCACCAGACCTGCTCCTTTGACCCAGTGCGTGGAAACAGCTGCTTTCTCCAGTGCCGCCATCT

GTCTTCTGTGTCTGCCTCAGACCTCACTTAAGATAATGTCAAAAGGCAATTCTGTGTATCACCCCACACA

GAGAGTTAAATGTTTTGGCTTGGCGCATTTGTAACTTTAGATATATTGCATTCTATTTTATTTTATAGAT

ACTAATTCCATTAATTTCATAAAAATGATTGTATAGGCATTTAGGATCATATTCATTCGAAGCAAAGTCC

GTTACAAAGGTTCAAGATTTCCATCTCAAAACACTACGCTCTTTTATGGGAACTGTGTGAACTGAAGTGG

AAAGCATCTACCATGCTGAGGCTAAAAGAAAAGATGAATCATTTTAGTTTGCAGATGGATCGTAAATATA

ATTGTTGGTATCAGCTTTAGCTCAAAACCAATATTAGGTGTTTTAATTTCCTTTTAAGGTTTGGAAGACA

GCCCTAATCTCAGGTTGGGGAGCTCATGTTAGTAGCAGTGACTTAAGGCTAAGTGTAGAAGATAATTTAA

GATACATTTTCTTTATATATTAGCCAACAAATTATATTTATTGGTTGGCTTGCTTTTCCGTTCTGATTTT

GAGAGTGCCCAGTTTGGTTTAGTTGACCAATGAATGTCAAAGCTACTTAGTTGAGAGAATTTCCTTGTTC

ATAAATGTAGAGCAGTGATTTGATTAGAAGCCAGCTTTGAGATAAATGTTAATTACCTCATGCATATCTC

CTGGGAATATTTCAAACTGTTTTAATGCATGTGTTATATATAAAAGTTTCTTGGGACATGCTCTTCACCT

GTTCTACCTAGTTATTTGCAAATTCAGACCTCCTATTGAACTCTGTCTGACCAAAACTACTTAAACTCAA

GGCCCAAAACTAGGGGCACCATTTACTGATTTTAAATTGAGTATATATCCCTTGACTTCTTCACTGTCAA

ATACTTTTGAAACTTCACGTTCAAGATAAGAATGGAATGTTGCTTTCTTGCAATAAGTAATGTTCTTTCT

GCCTTTTTTTCACTTTTAAGTCAGCCTTAAACACATGCCTCACAAACATCTACTTTCTCCACATACCTTT

GAGAGAGACACTGAATTGGCCTCAGCTCAGTTTTGCATAAGCTTAGTGCCAGAACCAGCACCTGATGCTT

TTCAGGTGAAAATAAAACAAACAGCTTCTCTAAAGCATCTTACCCCTGTGCTGGAGGTTTGAGGGACCTC

TTCAGTGCCTGCCCCTTGAGTCTAATGGTCACCACCTCATTCTGAAGTATGAGTTGAATTTTTTGCCCTC

TTTGCATATTTACATTAGTCATCACTTTGAAGCAATGCAGTGTGCTGGAAGGAGCACTATCTGCCTAGGT

AACTGCTAGTCATGACTTGGTCATCAGCTTGCTTTGTGGCACTGAGCAAGTTACTTCACTTCTCTGAGCC

TTGGTTTTATCATAGGGTGAGGAGGTTGGATACAATTAGTGCCCCTCTTAACCCTGCAGACTCAATGTTC

CCTTTTATAACAAGTATTTTATTCTGAATATGAAATGAAAATTAAAGTTAATATAATCATCTATGTGCAT

GTATAATTTTAAGCAGTGAACATAGTACCCTAACTATAATATAAAGCAGAAAAAAAGGCAACTTTTAATA

AAATAAAATGTATTTCAATAAAAAAAGCTTGGGTATAACCACCCTAGAAGATAAAATTAAGTCATTAGATG

GCTGAACCTGCATGTAGAGCCACCAGCTACAAATGAAAATCAATGTGTGTATTGGCAACAGAAAATCACG

GTGTTGTCATTGGATGTGACTTTCTGAAGTGGTGGGCAATTCTTGTTAATGTTTTAAACAAAAAAAAAAA

AACCTTACAGTCTTGCCCTGATTTACACAGCAGTCACATTCCTGGAAAATTCAAGTGTTTATTAAAACTA

TGCAACAGTTACTGTGTGTTATACGTTGAAAGGTCTTCACTAATATCTCACTAAGTAATGAGAATGCCTA

CATATCAGAATTTTTTTTTTCAGGAGCCAAGCACATATACTGATTTGGAAAAAGGCACAGGTAGCTCAGT

TTATTTGCTTTCTACCCTGCCTGGCCACTTGCTGTTTCTTCAGTTTCTAATTTGAGCTGTAACTACACAA

GGAAAGCTAAATAGTCTGGAAAATTTTTGGAAAGAATCCACAAAGCCAAAGGAGACTGGCCTATACTCAT

TTTATCTGGGGATGTACCTTACCCTTAGAGACTTTGAAAAATGTGAAGCTCTTATTTTGTAACCTGGGTA

AATGTTAGTTTCTAGATTTTCGGCTTAACATCTAATAATAACATTTAAAAAGTGCTTTTGTAACTATTAG

TTATTTGCAATAAAATGCTTTCCTTCTACAGTCCCAAGTTCAAAAAAAAAAAAAAAAAA
```

>NM_178499.4*Homo sapiens* coiled-coil domain containing 60 (CCDC60), mRNA
(SEQ ID NO: 3)

```
AGTTGCCTACTTTCCCCGCAGTGCGATAAACCCCTCGTTGGGGCCGCCTTAGTTCTCGGCCGCTCTCGGA

GGATGGCGATCTGGGAGCCCCTCCATGGGACCCCTCTCACACTTTGTCACTGGAATTTTATTTATTTTTT

AGTTCATATTTTATTTTGCTTATAGAAGAGAAAGATATCCCTTCCGAAGAGGAGGAAGCTTACAGAAGTT

TATAACCTTTCAAAAAGTAAATAAGTCCAGGCTTGCCTGATTCTGCCCTACCCGGACTTCCTTATCCCGT

CTGTGGGAGACCCAGGTGCTTTCTCATTACTCTTCAGAAGGAAACCGCTTTGGAGTTCGTGTAATTGGGA
```

-continued

```
CTTGGGGATCAGGGAGAAGTTGCCGAAACTTCTCATACCAGTAACTACTGAAGTAGAAGATTCTGGAAAA

ATCCTTGTCTTGGGGGCACAGGCTAAAACCTGAAGGATTTTTAAGATGACCAAGGTTCCAGCCACCAAGA

AGCTTCAGAGTTCCCCCAACTCGGGGGCTGTCCGGCCCTTTTATGCCTCGGAGAACCTAAGGCAGGTCCC

AGACAAGCCAATGAAGAGCATCAAGTATATGGACAAGGAAATAATAAACCTCAAAAAGGACCTTATACGA

AGCCGCTTTTTGATCCAGTCTGTGAAGATAGGCCGTGGATATTTTGCTATTCTGAGGGAAGAGACTGCAA

AGAAAAAGAAGCAACAACAACTTCAGAAACTGAAAGAGGAGGAAAGAAATAAATTCCAGCCAGCCGAAAA

GATCTCAGAAATCCACTATGGGGACACCTTATTGAGCACATATGATGATGAGAAGTTGAAGACACTGGGA

GCTAGAGTCACACGTCGCCCATTCACTCCCATCCACAGCTGCATCATTTCTCCCTCGCTAACCGAGGCTC

ACGTCGAGCCCCTCTTCCGCCAGCTCTGTGCTCTCCACTGGCTTCTGGAGGCCCTGACTATTGACCACAC

CCACCACACCATGAAGCCTGTGATCACCTGCTGGAACCCAAAGGACCCGGGTGGAAGCAAGAGCACCATT

AAAAAAATCAATAAGGACAAGTCCATGGGACAGAAATGGGAGCATTTCATCACAGCGCCAAAGACCAAGA

AATTCAAAATTCCCACAATGCGAGTCACCAACCGCAAACCAAGCCGGCGAGGCTCCACACTCAGTCTGAG

TCGGGCCAGTGGGGGGTCCTCTCCCCAGAGCAGCATGATCTCTGTGAACCCTGGCTCGGATGAGCCCCCA

AGTGTGAACACCCAGGTGACCAGCAGCAAGGACATTGAGGACAATGAGTCATCTTCAACCAAGCCAGATG

AAGAACCTCTGTATATGAATCTGCAGAAGCTCCTGGAGATGGTTCGGGAAGATGCCCGGAGGACAGTCAC

AATAGAAAATGGGATGCAAAGAAAAGCACCCAGCATCTTGTCAGTGCTGAAACAAAACAAGAGTAATTCT

GCTTATAAGGAAATGCAGACCACTCTCAAATCAAGTGAGAGATCCAGCAGTACAAGTGCAGAAAGCCACA

TCCAACCAGTCCAGAAGAAGTCTAAAAACCGCACTAATTGTGACATCAACATCCACTACAAGAGTGGGGT

GTGTAACACCATGAGGGCCAAGTTTTACAGCGTAGCCCAGGAGGCTGGCTTCTGCCTGCAGGACAAGATG

GAAATCCTCATGAAGCGCCAAGAAGAGAGAGGTATCCAGAAGTTCCGTGCTTTTGTCCTTGTCTCAAATT

TTCAAAAGGACATAGCAAAAATGAGACATCACATATCTGTAGTAAAAGGAGATGCAGAAGAAATTGCAGA

CCACTGGTACTTTGATCTGTTGTCCAAACTGCCAGAGGATCTAAAGAACTTCCGCCCCGCCAAAAAGATC

CTGGTGAAACTGCAGAAGTTTGGAGAAAACCTGGACTTGCGGATTCGACCCCATGTCCTCCTGAAGGTGC

TGCAGGATCTGAGGATTTGGGAACTGTGCTCCCCTGACATCGCTGTGGCTATTGAGTTTGTGCGAGAACA

CATCATCCATATGCCTCAAGAGGATTACATCAGCTGGCTGCAGAGCCGGATCAACATACCCATTGGGCCC

TACAGCGCCCTGAGGTAGGCTGGGCCTGGGTTGACCAGCTGTCTCAGTGGAGGAGTGTTTGCCTATATCA

TGTTCCTGTATCCTGCCTGTGTTCCTGCCTCCTGACTACCCTCATGGATGCTCTTTATGGATGACCCTTT

ACAGTAGGGTCATCTGGAGACTGACTTCCAGCAACATTTTTAGAGGGGGATGGCCCCGGTGGCCCTCCCC

TCAATTCCACACCCCAGACCCAACCTACCAGTCTCTGTTCTTCAATGATCCAGCCTGACTCTACCTACTT

CCTCTTCAGATTCCTTCACCCTATTTACCTTCCTCAAGTACTGGAGAATAAAATTGAACTGAATGTTTGA

AAAAA
```

>NM_001005407.1 *Homo sapiens* calcium voltage-gated channel subunit alpha1
H (CACNA1H), transcript variant 2, mRNA
                                                    (SEQ ID NO: 4)
```
CGAGGCCGCCGCCGTCGCCTCCGCCGGGCGAGCCGGAGCCGGAGTCGAGCCGCGCCGGGAGCCGGGCGG

GCTGGGGACGCGGGCCGGGGGCGGAGGCGCTGGGGGCCGGGGCCGGGGCCGGGGGCGGAGGCGCTGGGGG

CCGGGGCCGGGGCCGGGCGCCGAGCGGGGTCCGCGGTGACCGCGCCGCCCGGGCGATGCCCGCGGGGACG

CCGCCGGCCAGCAGAGCGAGGTGCTGCCGGCCGCCACCATGACCGAGGGCGCACGGGCCGCCGACGAGGT

CCGGGTGCCCCCTGGGCGCGCCGCCCCCCTGGCCCTGCGGCGTTGGTGGGGGCGTCCCCGGAGAGCCCGGG

GCGCCGGGACGCGGAGGCGGAGCGGGGGTCCGAGCTCGGCGTGTCACCCTCCGAGAGCCCGGCGGCCGAGC

GCGGCGCGGAGCTGGGTGCCGACGAGGAGCAGCGCGTCCCGTACCCGGCCTTGGCGGCCACGGTCTTCTT

CTGCCTCGGTCAGACCACGCGGCCGCGCAGCTGGTGCCTCCGGCTGGTCTGCAACCCATGGTTCGAGCAC
```

-continued

```
GTGAGCATGCTGGTAATCATGCTCAACTGCGTGACCCTGGGCATGTTCCGGCCCTGTGAGGACGTTGAGT

GCGGCTCCGAGCGCTGCAACATCCTGGAGGCCTTTGACGCCTTCATTTTCGCCTTTTTTGCGGTGGAGAT

GGTCATCAAGATGGTGGCCTTGGGGCTGTTCGGGCAGAAGTGTTACCTGGGTGACACGTGGAACAGGCTG

GATTTCTTCATCGTCGTGGCGGGCATGATGGAGTACTCGTTGGACGGACACAACGTGAGCCTCTCGGCTA

TCAGGACCGTGCGGGTGCTGCGGCCCCTCCGCGCCATCAACCGCGTGCCTAGCATGCGGATCCTGGTCAC

TCTGCTGCTGGATACGCTGCCCATGCTCGGGAACGTCCTTCTGCTGTGCTTCTTCGTCTTCTTCATTTTC

GGCATCGTTGGCGTCCAGCTCTGGGCTGGCCTCCTGCGGAACCGCTGCTTCCTGGACAGTGCCTTTGTCA

GGAACAACAACCTGACCTTCCTGCGGCCGTACTACCAGACGGAGGAGGGCGAGGAGAACCCGTTCATCTG

CTCCTCACGCCGAGACAACGGCATGCAGAAGTGCTCGCACATCCCCGGCCGCCGCGAGCTGCGCATGCCC

TGCACCCTGGGCTGGGAGGCCTACACGCAGCCGCCAGGCCGAGGGGGGTGGGCGCTGCACGCAACGCCTGCA

TCAACTGGAACCAGTACTACAACGTGTGCCGCTCGGGTGACTCCAACCCCCACAACGGTGCCATCAACTT

CGACAACATCGGCTACGCCTGGATTGCCATCTTCCAGGTGATCACGCTGGAAGGCTGGGTGGACATCATG

TACTACGTCATGGACGCCCACTCATTCTACAACTTCATCTATTTCATCCTGCTCATCATCGTGGGCTCCT

TCTTCATGATCAACCTGTGCCTGGTGGTGATTGCCACGCAGTTCTCGGAGACGAAGCAGCGGGAGAGTCA

GCTGATGCGGGAGCAGCGGGCACGCCACCTGTCCAACGACAGCACGCTGGCCAGCTTCTCCGAGCCTGGC

AGCTGCTACGAAGAGCTGCTGAAGTACGTGGGCCACATATTCCGCAAGGTCAAGCGGCGCAGCTTGCGCC

TCTACGCCCGCTGGCAGAGCCGCTGGCGCAAGAAGGTGGACCCCAGTGCTGTGCAAGGCCAGGGTCCCGG

GCACCGCCAGCGCCGGGCAGGCAGGCACACAGCCTCGGTGCACCACCTGGTCTACCACCACCATCACCAC

CACCACCACCACTACCATTTCAGCCATGGCAGCCCCCGCAGGCCCGGCCCCGAGCCAGGCGCCTGCGACA

CCAGGCTGGTCCGAGCTGGCGCGCCCCCCTCGCCACCTTCCCCAGGCCGCGGACCCCCCGACGCAGAGTC

TGTGCACAGCATCTACCATGCCGACTGCCACATAGAGGGGCCGCAGGAGAGGGCCCGGGTGGCACATGCC

GCAGCCACTGCCGCTGCCAGCCTCAGACTGGCCACAGGGCTGGGCACCATGAACTACCCCACGATCCTGC

CCTCAGGGGTGGGCAGCGGCAAAGGCAGCACCAGCCCCGGACCCAAGGGGAAGTGGGCCGGTGGACCGCC

AGGCACCGGGGGGCACGGCCCGTTGAGCTTGAACAGCCCTGATCCCTACGAGAAGATCCCGCATGTGGTC

GGGGAGCATGGACTGGGCCAGGCCCCTGGCCATCTGTCGGGCCTCAGTGTGCCCTGCCCCCTGCCCAGCC

CCCCAGCGGGCACACTGACCTGTGAGCTGAAGAGCTGCCCGTACTGCACCCGTGCCCTGGAGGACCCGGA

GGGTGAGCTCAGCGGCTCGGAAAGTGGAGACTCAGATGGCCGTGGCGTCTATGAATTCACGCAGGACGTC

CGGCACGGTGACCGCTGGGACCCCACGCGACCACCCCGTGCGACGGACACACCAGGCCCAGGCCCAGGCA

GCCCCCAGCGGCGGGCACAGCAGAGGGCAGCCCCGGGCGAGCCAGGCTGGATGGGCCGCCTCTGGGTTAC

CTTCAGCGGCAAGCTGCGCCGCATCGTGGACAGCAAGTACTTCAGCCGTGGCATCATGATGGCCATCCTT

GTCAACACGCTGAGCATGGGCGTGGAGTACCATGAGCAGCCCGAGGAGCTGACTAATGCTCTGGAGATCA

GCAACATCGTGTTCACCAGCATGTTTGCCCTGGAGATGCTGCTGAAGCTGCTGGCCTGCGGCCCTCTGGG

CTACATCCGGAACCCGTACAACATCTTCGACGGCATCATCGTGGTCATCAGCGTCTGGGAGATCGTGGGG

CAGGCGGACGGTGGCTTGTCTGTGCTGCGCACCTTCCGGCTGCTGCGCGTGCTGAAGCTGGTGCGCTTTC

TGCCAGCCCTGCGGCGCCAGCTCGTGGTGCTGGTGAAGACCATGGACAACGTGGCTACCTTCTGCACGCT

GCTCATGCTCTTCATTTTCATCTTCAGCATCCTGGGCATGCACCTTTTCGGCTGCAAGTTCAGCCTGAAG

ACAGACACCGGAGACACCGTGCCTGACAGGAAGAACTTCGACTCCCTGCTGTGGGCCATCGTCACCGTGT

TCCAGATCCTGACCCAGGAGGACTGGAACGTGGTCCTGTACAACGGCATGGCCTCCACCTCCTCCTGGGC

CGCCCTCTACTTCGTGGCCCTCATGACCTTCGGCAACTATGTGCTCTTCAACCTGCTGGTGGCCATCCTC

GTGGAGGGCTTCCAGGCGGAGGGCGATGCCAACAGATCCGACACGGACGAGGACAAGACGTCGGTCCACT
```

-continued

```
TCGAGGAGGACTTCCACAAGCTCAGAGAACTCCAGACCACAGAGCTGAAGATGTGTTCCCTGGCCGTGAC

CCCCAACGGGCACCTGGAGGGACGAGGCAGCCTGTCCCCTCCCCTCATCATGTGCACAGCTGCCACGCCC

ATGCCTACCCCCAAGAGCTCACCATTCCTGGATGCAGCCCCCAGCCTCCCAGACTCTCGGCGTGGCAGCA

GCAGCTCCGGGGACCCGCCACTGGGAGACCAGAAGCCTCCGGCCAGCCTCCGAAGTTCTCCCTGTGCCCC

CTGGGGCCCCAGTGGCGCCTGGAGCAGCCGGCGCTCCAGCTGGAGCAGCCTGGGCCGTGCCCCCAGCCTC

AAGCGCCGCGGCCAGTGTGGGGAACGTGAGTCCCTGCTGTCTGGCGAGGGCAAGGGCAGCACCGACGACG

AAGCTGAGGACGGCAGGGCCGCGCCCGGGCCCCGTGCCACCCCACTGCGGCGGGCCGAGTCCCTGGACCC

ACGGCCCCTGCGGCCGGCCGCCCTCCCGCCTACCAAGTGCCGCGATCGCGACGGGCAGGTGGTGGCCCTG

CCCAGCGACTTCTTCCTGCGCATCGACAGCCACCGTGAGGATGCAGCCGAGCTTGACGACGACTCGGAGG

ACAGCTGCTGCCTCCGCCTGCATAAAGTGCTGGAGCCCTACAAGCCCCAGTGGTGCCGGAGCCGCGAGGC

CTGGGCCCTCTACCTCTTCTCCCCACAGAACCGGTTCCGCGTCTCCTGCCAGAAGGTCATCACACACAAG

ATGTTTGATCACGTGGTCCTCGTCTTCATCTTCCTCAACTGCGTCACCATCGCCCTGGAGAGGCCTGACA

TTGATCCCGGCAGCACCGAGCGGGTCTTCCTCAGCGTCTCCAATTACATCTTCACGGCCATCTTCGTGGC

GGAGATGATGGTGAAGGTGGTGGCCCTGGGGCTGCTGTCCGGCGAGCACGCCTACCTGCAGAGCAGCTGG

AACCTGCTGGATGGGCTGCTGGTGCTGGTGTCCCTGGTGGACATTGTCGTGGCCATGGCCTCGGCTGGTG

GCGCCAAGATCCTGGGTGTTCTGCGCGTGCTGCGTCTGCTGCGGACCCTGCGGCCTCTGAGGGTCATCAG

CCGGGCCCCGGGCCTCAAGCTGGTGGTGGGAGACGCTGATATCATCACTCAGGCCCATTGGGAACATCGTC

CTCATCTGCTGCGCCTTCTTCATCATTTTTGGCATTTTGGGTGTGCAGCTCTTCAAAGGGAAGTTCTACT

ACTGCGAGGGCCCCGACACCAGGAACATCTCCACCAAGGCACAGTGCCGGGCCGCCCACTACCGCTGGGT

GCGACGCAAGTACAACTTCGACAACCTGGGCCAGGCCCTGATGTCGCTGTTCGTGCTGTCATCCAAGGAT

GGATGGGTGAACATCATGTACGACGGGCTGGATGCCGTGGGTGTCGACCAGCAGCCTGTGCAGAACCACA

ACCCCTGGATGCTGCTGTACTTCATCTCCTTCCTGCTCATCGTCAGCTTCTTCGTGCTCAACATGTTCGT

GGGCGTCGTGGTCGAGAACTTCCACAAGTGCCGGCAGCACCAGGAGGCGGAGGAGGCGCGGCGGCGAGAG

GAGAAGCGGCTGCGGCGCCTAGAGAGGAGGCGCAGGAAGGCCCAGCGCCGGCCCTACTATGCCGACTACT

CGCCCACGCGCCGCTCCATTCACTCGCTGTGCACCAGCCACTATCTCGACCTCTTCATCACCTTCATCAT

CTGTGTCAACGTCATCACCATGTCCATGGAGCACTATAACCAACCCAAGTCGCTGGACGAGGCCCTCAAG

TACTGCAACTACGTCTTCACCATCGTGTTTGTCTTCGAGGCTGCACTGAAGCTGGTAGCATTTGGGTTCC

GTCGGTTCTTCAAGGACAGGTGGAACCAGCTGGACCTGGCCATCGTGCTGCTGTCACTCATGGGCATCAC

GCTGGAGGAGATAGAGATGAGCGCCGCGCTGCCCATCAACCCCACCATCATCCGCATCATGCGCGTGCTT

CGCATTGCCCGTGTGCTGAAGCTGCTGAAGATGGCTACGGGCATGCGCGCCCTGCTGGACACTGTGGTGC

AAGCTCTCCCCCAGGTGGGGAACCTGGGCCTTCTTTTCATGCTCCTGTTTTTTATCTATGCTGCGCTGGG

AGTGGAGCTGTTCGGGAGGCTGGAGTGCAGTGAAGACAACCCCTGCGAGGGCCTGAGCAGGCACGCCACC

TTCAGCAACTTCGGCATGGCCTTCCTCACGCTGTTCCGCGTGTCCACGGGGGACAACTGGAACGGGATCA

TGAAGGACACGCTGCGCGAGTGCTCCCGTGAGGACAAGCACTGCCTGAGCTACCTGCCGGCCCTGTCGCC

CGTCTACTTCGTGACCTTCGTGCTGGTGGCCCAGTTCGTGCTGGTGAACGTGGTGGTGGCCGTGCTCATG

AAGCACCTGGAGGAGAGCAACAAGGAGGCACGGGAGGATGCGGAGCTGGACGCCGAGATCGAGCTGGAGA

TGGCGCAGGGCCCCGGGAGTGCACGCCGGGTGGACGCGGACAGGCCTCCCTTGCCCCAGGAGAGTCCGGG

CGCCAGGGACGCCCCAAACCTGGTTGCACGCAAGGTGTCCGTGTCCAGGATGCTCTCGCTGCCCAACGAC

AGCTACATGTTCAGGCCCGTGGTGCCTGCCTCGGCGCCCCACCCCCGCCCGCTGCAGGAGGTGGAGATGG

AGACCTATGGGGCCGGCACCCCCTTGGGCTCCGTTGCCTCTGTGCACTCTCCGCCCGCAGAGTCCTGTGC

CTCCCTCCAGATCCCATTGGCTGTGTCGTCCCCAGCCAGGAGCGGCGAGCCCCTCCACGCCCTGTCCCCT
```

-continued

CGGGGCACAGCCCGCTCCCCCAGTCTCAGCCGGCTGCTCTGCAGACAGGAGGCTGTGCACACCGATTCCT

TGGAAGGGAAGATTGACAGCCCTAGGGACACCCTGGATCCTGCAGAGCCTGGTGAGAAAACCCCGGTGAG

GCCGGTGACCCAGGGGGGCTCCCTGCAGTCCCCACCACGCTCCCCACGGCCCGCCAGCGTCCGCACTCGT

AAGCATACCTTCGGACAGCGCTGCGTCTCCAGCCGGCCGGCGGCCCCAGGCGGAGAGGAGGCCGAGGCCT

CGGACCCAGCCGACGAGGAGGTCAGCCACATCACCAGCTCCGCCTGCCCCTGGCAGCCCACAGCCGAGCC

CCATGGCCCCGAAGCCTCTCCGGTGGCCGGCGGCGAGCGGGACCTGCGCAGGCTCTACAGCGTGGATGCT

CAGGGCTTCCTGGACAAGCCGGGCCGGGCAGACGAGCAGTGGCGGCCCTCGGCGGAGCTGGGCAGCGGGG

AGCCTGGGGAGGCGAAGGCCTGGGGCCCTGAGGCCGAGCCCGCTCTGGGTGCGCGCAGAAAGAAGAAGAT

GAGCCCCCCCTGCATCTCGGTGGAACCCCCTGCGGAGGACGAGGGCTCTGCGCGGCCCTCCGCGGCAGAG

GGCGGCAGCACCACACTGAGGCGCAGGACCCCGTCCTGTGAGGCCACGCCTCACAGGGACTCCCTGGAGC

CCACAGAGGGCTCAGGCGCCGGGGGGGACCCTGCAGCCAAGGGGGAGCGCTGGGGCCAGGCCTCCTGCCG

GGCTGAGCACCTGACCGTCCCCAGCTTTGCCTTTGAGCCGCTGGACCTCGGGGTCCCCAGTGGAGACCCT

TTCTTGGACGGTAGCCACAGTGTGACCCCAGAATCCAGAGCTTCCTCTTCAGGGGCCATAGTGCCCCTGG

AACCCCCAGAATCAGAGCCTCCCATGCCCGTCGGTGACCCCCCAGAGAAGAGGCGGGGGCTGTACCTCAC

AGTCCCCCAGTGTCCTCTGGAGAAACCAGGGTCCCCCTCAGCCACCCCTGCCCCAGGGGGTGGTGCAGAT

GACCCCGTGTAGCTCGGGGCTTGGTGCCGCCCACGGCTTTGGCCCTGGGGTCTGGGGGCCCCGCTGGGGT

GGAGGCCCAGGCAGAACCCTGCATGGACCCTGACTTGGGTCCCGTCGTGAGCAGAAAGGCCCGGGGGAGGA

TGACGGCCCAGGCCCTGGTTCTCTGCCCAGCGAAGCAGGAGTAGCTGCCGGGCCCCACGAGCCTCCGTCC

GTTCTGGTTCGGGTTTCTCCGAGTTTTGCTACCAGCCGAGGCTGTGCGGGCAACTGGGTCAGCCTCCCGT

CAGGAGAGAAGCCGCGTCTGTGGGACGAAGACCGGGCACCCGCCAGAGAGGGGAAGGTACCAGGTTGCGT

CCTTTCAGGCCCCGCGTTGTTACAGGACACTCGCTGGGGGCCCTGTGCCCTTGCCGGCGGCAGGTTGCAG

CCACCGCGGCCCAATGTCACCTTCACTCACAGTCTGAGTTCTTGTCCGCCTGTCACGCCCTCACCACCCT

CCCCTTCCAGCCACCACCCTTTCCGTTCCGCTCGGGCCTTCCCAGAAGCGTCCTGTGACTCTGGGAGAGG

TGACACCTCACTAAGGGGCCGACCCCATGGAGTAACGCGCCCGGCCCCGATGCGAATCAGGCCTCCCCTA

CATCTGGGGGCGTTGGCCGCGAGATTCCCATTGACACCTTTGTTTCGTGTGCTTTTAAATTCAGGTTAAA

TGTTGCAATAATCTGATGCAGAAGACTCAGCTTCTCAAGGGAGAGGGAGGGGGCGGAGCGGAATAAATAG

TAACTTATTTAAGAAATGCAAAAAAAAAA

>NM_021098.2 *Homo sapiens* calcium voltage-gated channel subunit alpha1 H
(CACNA1H) , transcript variant 1, mRNA
(SEQ ID NO: 5)
CGAGGCCGCCGCCGTCGCCTCCGCCGGGCGAGCCGGAGCCGGAGTCGAGCCGCGCCGGGAGCCGGGCGG

GCTGGGGACGCGGGCCGGGGGCGGAGGCGCTGGGGGCCGGGGCCGGGGCCGGGGGCGGAGGCGCTGGGGG

CCGGGGCCGGGGCCGGGCGCCGAGCGGGGTCCGCGGTGACCGCGCCGCCCGGGCGATGCCCGCGGGGACG

CCGCCGGCCAGCAGAGCGAGGTGCTGCCGGCCGCCACCATGACCGAGGGCGCACGGGCCGCCGACGAGGT

CCGGGTGCCCCTGGGCGCGCCGCCCCCTGGCCCTGCGGCGTTGGTGGGGGCGTCCCCGGAGAGCCCCGGG

GCGCCGGGACGCGAGGCGGAGCGGGGGTCCGAGCTCGGCGTGTCACCCTCCGAGAGCCCGGCGGCCGAGC

GCGGCGCGGAGCTGGGTGCCGACGAGGAGCAGCGCGTCCCGTACCCGGCCTTGGCGGCCACGGTCTTCTT

CTGCCTCGGTCAGACCACGCGGCCGCGCAGCTGGTGCCTCCGGCTGGTCTGCAACCCATGGTTCGAGCAC

GTGAGCATGCTGGTAATCATGCTCAACTGCGTGACCCTGGGCATGTTCCGGCCCTGTGAGGACGTTGAGT

GCGGCTCCGAGCGCTGCAACATCCTGGAGGCCTTTGACGCCTTCATTTTCGCCTTTTTTGCGGTGGAGAT

GGTCATCAAGATGGTGGCCTTGGGGCTGTTCGGGCAGAAGTGTTACCTGGGTGACACGTGGAACAGGCTG

GATTTCTTCATCGTCGTGGCGGGCATGATGGAGTACTCGTTGGACGGACACAACGTGAGCCTCTCGGCTA

-continued

```
TCAGGACCGTGCGGGTGCTGCGGCCCCTCCGCGCCATCAACCGCGTGCCTAGCATGCGGATCCTGGTCAC

TCTGCTGCTGGATACGCTGCCCATGCTCGGGAACGTCCTTCTGCTGTGCTTCTTCGTCTTCTTCATTTTC

GGCATCGTTGGCGTCCAGCTCTGGGCTGGCCTCCTGCGGAACCGCTGCTTCCTGGACAGTGCCTTTGTCA

GGAACAACAACCTGACCTTCCTGCGGCCGTACTACCAGACGGAGGAGGGCGAGGAGAACCCGTTCATCTG

CTCCTCACGCCGAGACAACGGCATGCAGAAGTGCTCGCACATCCCCGGCCGCCGCGAGCTGCGCATGCCC

TGCACCCTGGGCTGGGAGGCCTACACGCAGCCGCAGGCCGAGGGGGTGGGCGCTGCACGCAACGCCTGCA

TCAACTGGAACCAGTACTACAACGTGTGCCGCTCGGGTGACTCCAACCCCCACAACGGTGCCATCAACTT

CGACAACATCGGCTACGCCTGGATTGCCATCTTCCAGGTGATCACGCTGGAAGGCTGGGTGGACATCATG

TACTACGTCATGGACGCCCACTCATTCTACAACTTCATCTATTTCATCCTGCTCATCATCGTGGGCTCCT

TCTTCATGATCAACCTGTGCCTGGTGGTGATTGCCACGCAGTTCTCGGAGACGAAGCAGCGGGAGAGTCA

GCTGATGCGGGAGCAGCGGGCACGCCACCTGTCCAACGACAGCACGCTGGCCAGCTTCTCCGAGCCTGGC

AGCTGCTACGAAGAGCTGCTGAAGTACGTGGGCCACATATTCCGCAAGGTCAAGCGGCGCAGCTTGCGCC

TCTACGCCCGCTGGCAGAGCCGCTGGCGCAAGAAGGTGGACCCCAGTGCTGTGCAAGGCCAGGGTCCCGG

GCACCGCCAGCGCCGGGCAGGCAGGCACACAGCCTCGGTGCACCACCTGGTCTACCACCACCATCACCAC

CACCACCACCACTACCATTTCAGCCATGGCAGCCCCCGCAGGCCCGGCCCCGAGCCAGGCGCCTGCGACA

CCAGGCTGGTCCGAGCTGGCGCGCCCCCCTCGCCACCTTCCCCAGGCGCGCGGACCCCCCGACGCAGAGTC

TGTGCACAGCATCTACCATGCCGACTGCCACATAGAGGGGCCGCAGGAGAGGGCCCGGGTGGCACATGCC

GCAGCCACTGCCGCTGCCAGCCTCAGACTGGCCACAGGGCTGGGCACCATGAACTACCCCACGATCCTGC

CCTCAGGGGTGGGCAGCGGCAAAGGCAGCACCAGCCCCGGACCCAAGGGGAAGTGGGCCGGTGGACCGCC

AGGCACCGGGGGGCACGGCCCGTTGAGCTTGAACAGCCCTGATCCCTACGAGAAGATCCCGCATGTGGTC

GGGGAGCATGGACTGGGCCAGGCCCCTGGCCATCTGTCGGGCCTCAGTGTGCCCTGCCCCCTGCCCAGCC

CCCCAGCGGGCACACTGACCTGTGAGCTGAAGAGCTGCCCGTACTGCACCCGTGCCCTGGAGGACCCGGA

GGGTGAGCTCAGCGGCTCGGAAAGTGGAGACTCAGATGGCCGTGGCGTCTATGAATTCACGCAGGACGTC

CGGCACGGTGACCGCTGGGACCCCACGCGACCACCCCGTGCGACGGACACACCAGGCCCAGGCCCAGGCA

GCCCCCAGCGGCGGGCACAGCAGAGGGCAGCCCCGGGCGAGCCAGGCTGGATGGGCCGCCTCTGGGTTAC

CTTCAGCGGCAAGCTGCGCCGCATCGTGGACAGCAAGTACTTCAGCCGTGGCATCATGATGGCCATCCTT

GTCAACACGCTGAGCATGGGCGTGGAGTACCATGAGCAGCCCGAGGAGCTGACTAATGCTCTGGAGATCA

GCAACATCGTGTTCACCAGCATGTTTGCCCTGGAGATGCTGCTGAAGCTGCTGGCCTGCGGCCCTCTGGG

CTACATCCGGAACCCGTACAACATCTTCGACGGCATCATCGTGGTCATCAGCGTCTGGGAGATCGTGGGG

CAGGCGGACGGTGGCTTGTCTGTGCTGCGCACCTTCCGGCTGCTGCGCGTGCTGAAGCTGGTGCGCTTTC

TGCCAGCCCTGCGGCGCCAGCTCGTGGTGCTGGTGAAGACCATGGACAACGTGGCTACCTTCTGCACGCT

GCTCATGCTCTTCATTTTCATCTTCAGCATCCTGGGCATGCACCTTTTCGGCTGCAAGTTCAGCCTGAAG

ACAGACACCGGAGACACCGTGCCTGACAGGAAGAACTTCGACTCCCTGCTGTGGGCCATCGTCACCGTGT

TCCAGATCCTGACCCAGGAGGACTGGAACGTGGTCCTGTACAACGGCATGGCCTCCACCTCCTCCTGGGC

CGCCCTCTACTTCGTGGCCCTCATGACCTTCGGCAACTATGTGCTCTTCAACCTGCTGGTGGCCATCCTC

GTGGAGGGCTTCCAGGCGGAGGGCGATGCCAACAGATCCGACACGGACGAGGACAAGACGTCGGTCCACT

TCGAGGAGGACTTCCACAAGCTCAGAGAACTCCAGACCACAGAGCTGAAGATGTGTTCCCTGGCCGTGAC

CCCCAACGGGCACCTGGAGGGACGAGGCAGCCTGTCCCCTCCCCTCATCATGTGCACAGCTGCCACGCCC

ATGCCTACCCCCAAGAGCTCACCATTCCTGGATGCAGCCCCCAGCCTCCCAGACTCTCGGCGTGGCAGCA

GCAGCTCCGGGGACCCGCCACTGGGAGACCAGAAGCCTCCGGCCAGCCTCCGAAGTTCTCCCTGTGCCCC
```

-continued

```
CTGGGGCCCCAGTGGCGCCTGGAGCAGCCGGCGCTCCAGCTGGAGCAGCCTGGGCCGTGCCCCCAGCCTC

AAGCGCCGCGGCCAGTGTGGGGAACGTGAGTCCCTGCTGTCTGGCGAGGGCAAGGGCAGCACCGACGACG

AAGCTGAGGACGGCAGGGCCGCGCCCGGGCCCCGTGCCACCCCACTGCGGCGGGCCGAGTCCCTGGACCC

ACGGCCCCTGCGGCCGGCCGCCCTCCCGCCTACCAAGTGCCGCGATCGCGACGGGCAGGTGGTGGCCCTG

CCCAGCGACTTCTTCCTGCGCATCGACAGCCACCGTGAGGATGCAGCCGAGCTTGACGACGACTCGGAGG

ACAGCTGCTGCCTCCGCCTGCATAAAGTGCTGGAGCCCTACAAGCCCCAGTGGTGCCGGAGCCGCGAGGC

CTGGGCCCTCTACCTCTTCTCCCCACAGAACCGGTTCCGCGTCTCCTGCCAGAAGGTCATCACACACAAG

ATGTTTGATCACGTGGTCCTCGTCTTCATCTTCCTCAACTGCGTCACCATCGCCCTGGAGAGGCCTGACA

TTGATCCCGGCAGCACCGAGCGGGTCTTCCTCAGCGTCTCCAATTACATCTTCACGGCCATCTTCGTGGC

GGAGATGATGGTGAAGGTGGTGGCCCTGGGGCTGCTGTCCGGCGAGCACGCCTACCTGCAGAGCAGCTGG

AACCTGCTGGATGGGCTGCTGGTGCTGGTGTCCCTGGTGGACATTGTCGTGGCCATGGCCTCGGCTGGTG

GCGCCAAGATCCTGGGTGTTCTGCGCGTGCTGCGTCTGCTGCGGACCCTGCGGCCTCTGAGGGTCATCAG

CCGGGCCCCGGGCCTCAAGCTGGTGGTGGAGACGCTGATATCATCACTCAGGCCCATTGGGAACATCGTC

CTCATCTGCTGCGCCTTCTTCATCATTTTTGGCATTTTGGGTGTGCAGCTCTTCAAAGGGAAGTTCTACT

ACTGCGAGGGCCCCGACACCAGGAACATCTCCACCAAGGCACAGTGCCGGGCCGCCCACTACCGCTGGGT

GCGACGCAAGTACAACTTCGACAACCTGGGCCAGGCCCTGATGTCGCTGTTCGTGCTGTCATCCAAGGAT

GGATGGGTGAACATCATGTACGACGGGCTGGATGCCGTGGGTGTCGACCAGCAGCCTGTGCAGAACCACA

ACCCCTGGATGCTGCTGTACTTCATCTCCTTCCTGCTCATCGTCAGCTTCTTCGTGCTCAACATGTTCGT

GGGCGTCGTGGTCGAGAACTTCCACAAGTGCCGGCAGCACCAGGAGGCGGAGGAGGCGCGGCGGCGAGAG

GAGAAGCGGCTGCGGCGCCTAGAGAGGAGGCGCAGGAGCACTTTCCCCAGCCCAGAGGCCCAGCGCCGGC

CCTACTATGCCGACTACTCGCCCACGCGCCGCTCCATTCACTCGCTGTGCACCAGCCACTATCTCGACCT

CTTCATCACCTTCATCATCTGTGTCAACGTCATCACCATGTCCATGGAGCACTATAACCAACCCAAGTCG

CTGGACGAGGCCCTCAAGTACTGCAACTACGTCTTCACCATCGTGTTTGTCTTCGAGGCTGCACTGAAGC

TGGTAGCATTTGGGTTCCGTCGGTTCTTCAAGGACAGGTGGAACCAGCTGGACCTGGCCATCGTGCTGCT

GTCACTCATGGGCATCACGCTGGAGGAGATAGAGATGAGCGCCGCGCTGCCCATCAACCCCACCATCATC

CGCATCATGCGCGTGCTTCGCATTGCCCGTGTGCTGAAGCTGCTGAAGATGGCTACGGGCATGCGCGCCC

TGCTGGACACTGTGGTGCAAGCTCTCCCCCAGGTGGGGAACCTGGGCCTTCTTTTCATGCTCCTGTTTTT

TATCTATGCTGCGCTGGGAGTGGAGCTGTTCGGGGAGGCTGGAGTGCAGTGAAGACAACCCCTGCGAGGGC

CTGAGCAGGCACGCCACCTTCAGCAACTTCGGCATGGCCTTCCTCACGCTGTTCCGCGTGTCCACGGGGG

ACAACTGGAACGGGATCATGAAGGACACGCTGCGCGAGTGCTCCCGTGAGGACAAGCACTGCCTGAGCTA

CCTGCCGGCCCTGTCGCCCGTCTACTTCGTGACCTTCGTGCTGGTGGCCCAGTTCGTGCTGGTGAACGTG

GTGGTGGCCGTGCTCATGAAGCACCTGGAGGAGAGCAACAAGGAGGCACGGGAGGATGCGGAGCTGGACG

CCGAGATCGAGCTGGAGATGGCGCAGGGCCCCGGGAGTGCACGCCGGGTGGACGCGGACAGGCCTCCCTT

GCCCCAGGAGAGTCCGGGCGCCAGGGACGCCCCAAACCTGGTTGCACGCAAGGTGTCCGTGTCCAGGATG

CTCTCGCTGCCCAACGACAGCTACATGTTCAGGCCCGTGGTGCCTGCCTCGGCGCCCCACCCCCGCCCGC

TGCAGGAGGTGGAGATGGAGACCTATGGGGCCGGCACCCCCTTGGGCTCCGTTGCCTCTGTGCACTCTCC

GCCCGCAGAGTCCTGTGCCTCCCTCCAGATCCCATTGGCTGTGTCGTCCCCAGCCAGGAGCGGCGAGCCC

CTCCACGCCCTGTCCCCTCGGGGCACAGCCCGCTCCCCCAGTCTCAGCCGGCTGCTCTGCAGACAGGAGG

CTGTGCACACCGATTCCTTGGAAGGGAAGATTGACAGCCCTAGGGACACCCTGGATCCTGCAGAGCCTGG

TGAGAAAACCCCGGTGAGGCCGGTGACCCAGGGGGGCTCCCTGCAGTCCCCACCACGCTCCCCACGGCCC

GCCAGCGTCCGCCACTCGTAAGCATACCTTCGGACAGCGCTGCGTCTCCAGCCGGCCGGCGGCCCCAGGCG
```

-continued

GAGAGGAGGCCGAGGCCTCGGACCCAGCCGACGAGGAGGTCAGCCACATCACCAGCTCCGCCTGCCCCTG

GCAGCCCACAGCCGAGCCCCATGGCCCCGAAGCCTCTCCGGTGGCCGGCGGCGAGCGGGACCTGCGCAGG

CTCTACAGCGTGGATGCTCAGGGCTTCCTGGACAAGCCGGGCCGGGCAGACGAGCAGTGGCGGCCCTCGG

CGGAGCTGGGCAGCGGGGAGCCTGGGGAGGCGAAGGCCTGGGGCCCTGAGGCCGAGCCCGCTCTGGGTGC

GCGCAGAAAGAAGAAGATGAGCCCCCCCTGCATCTCGGTGGAACCCCCTGCGGAGGACGAGGGCTCTGCG

CGGCCCTCCGCGGCAGAGGGCGGCAGCACCACACTGAGGCGCAGGACCCCGTCCTGTGAGGCCACGCCTC

ACAGGGACTCCCTGGAGCCCACAGAGGGCTCAGGCGCCGGGGGGGACCCTGCAGCCAAGGGGGAGCGCTG

GGGCCAGGCCTCCTGCCGGGCTGAGCACCTGACCGTCCCCAGCTTTGCCTTTGAGCCGCTGGACCTCGGG

GTCCCCAGTGGAGACCCTTTCTTGGACGGTAGCCACAGTGTGACCCCAGAATCCAGAGCTTCCTCTTCAG

GGGCCATAGTGCCCCTGGAACCCCCAGAATCAGAGCCTCCCATGCCCGTCGGTGACCCCCCAGAGAAGAG

GCGGGGGCTGTACCTCACAGTCCCCCAGTGTCCTCTGGAGAAACCAGGGTCCCCCTCAGCCACCCCTGCC

CCAGGGGGTGGTGCAGATGACCCCGTGTAGCTCGGGGCTTGGTGCCGCCCACGGCTTTGGCCCTGGGGTC

TGGGGGCCCCGCTGGGGTGGAGGCCCAGGCAGAACCCTGCATGGACCCTGACTTGGGTCCCGTCGTGAGC

AGAAAGGCCCGGGGAGGATGACGGCCCAGGCCCTGGTTCTCTGCCCAGCGAAGCAGGAGTAGCTGCCGGG

CCCCACGAGCCTCCGTCCGTTCTGGTTCGGGTTTCTCCGAGTTTTGCTACCAGCCGAGGCTGTGCGGGCA

ACTGGGTCAGCCTCCCGTCAGGAGAGAAGCCGCGTCTGTGGGACGAAGACCGGGCACCCGCCAGAGAGGG

GAAGGTACCAGGTTGCGTCCTTTCAGGCCCCGCGTTGTTACAGGACACTCGCTGGGGGCCCTGTGCCCTT

GCCGGCGGCAGGTTGCAGCCACCGCGGCCCAATGTCACCTTCACTCACAGTCTGAGTTCTTGTCCGCCTG

TCACGCCCTCACCACCCTCCCCTTCCAGCCACCACCCTTTCCGTTCCGCTCGGGCCTTCCCAGAAGCGTC

CTGTGACTCTGGGAGAGGTGACACCTCACTAAGGGGCCGACCCCATGGAGTAACGCGCCCGGCCCCGATG

CGAATCAGGCCTCCCCTACATCTGGGGGCGTTGGCCGCGAGATTCCCATTGACACCTTTGTTTCGTGTGC

TTTTAAATTCAGGTTAAATGTTGCAATAATCTGATGCAGAAGACTCAGCTTCTCAAGGGAGAGGGAGGGG

GCGGAGCGGAATAAATAGTAACTTATTTAAGAAATGCAAAAAAAAAA

>NM_032251.5 *Homo sapiens* coiled-coil domain containing 88B (CCDC88B),
mRNA (SEQ ID NO: 6)

CTCAGGGCAGGTGCAGCTGCCACAGTGAGACGGGCACCCCGACCCGGGCATGGAGGGGGGCAAGGGGCCC

AGGCTCAGAGACTTCCTGAGTGGGAGTCTGGCTACCTGGGCGCTGGGACTGGCCGGGCTGGTCGGGGAGG

CGGAGGACTCGGAGGGGGAAGAAGAGGAAGAGGAGGAAGAGCCGCCCCTTTGGTTGGAGAAGAGATTCCT

GCGCCTCAGCGATGGGGCCCTGCTCCTCCGGGTGCTGGGCATCATTGCCCCCAGCTCCCGAGGGGGACCT

CGGATGCTCAGAGGCCTTGACGGACCTGCTGCCTGGCGAGTGTGGAACCTGAACCACCTGTGGGGCCGAC

TGAGGGACTTCTACCAGGAGGAGCTGCAGCTGCTGATCCTGTCGCCACCCCCAGACCTCCAGACATTGGG

ATTTGACCCTCTCTCAGAAGAAGCGGTGGAGCAGCTGGAAGGCGTTCTTCGGCTACTGTTGGGAGCGTCA

GTACAGTGTGAGCACCGGGAACTCTTCATCCGCCACATCCAGGGCCTCAGTCTCGAGGTCCAGAGCGAGC

TGGCCGCTGCCATCCAGGAGGTGACCCAGCCGGGGGCCGGCGTGGTGCTGGCACTGTCTGGGCCAGATCC

TGGGGAGCTGGCACCTGCCGAGCTGGAGATGCTGTCCCGGAGCCTGATGGGGACACTGTCGAAGCTGGCA

CGGGAGCGTGACCTGGGGGCCCAGCGGCTGGCTGAACTGCTGCTGGAGCGAGAACCCCTCTGCTTGAGGC

CTGAGGCTCCCTCTAGGGCTCCCGCCGAGGGCCCCTCGCACCATCTGGCCCTGCAGCTGGCCAACGCCAA

GGCTCAGCTGCGGCGTCTGCGGCAGGAGCTGGAGGAGAAGGCCGAGCTGCTGCTAGACTCCCAGGCCGAG

GTGCAGGGTTTGGAGGCCGAAATAAGAAGGCTCCGCCAGGAGGCCCAGGCGCTGTCGGGACAGGCCAAGC

GGGCCGAGCTGTACCGCGAGGAGGCAGAGGCGCTGCGGGAGCGGGCCGGCCGCCTGCCCCGCCTGCAGGA

GGAGCTGAGGCGCTGCCGCGAGCGGCTGCAGGCGGCTGAGGCCTACAAGAGTCAGCTGGAGGAGGAGCGG

-continued

```
GTGCTCTCGGGGGTGCTGGAGGCGTCCAAGGCGCTGCTGGAAGAGCAGCTGGAGGCTGCCCGAGAGCGCT

GCGCCCGGCTGCACGAGACCCAGCGCGAGAACCTGCTGCTGCGAACCCGGCTGGGCGAGGCCCATGCGGA

GCTGGACTCTCTGCGGCATCAGGTGGACCAGCTGGCTGAGGAGAATGTGGAGCTGGAGCTGGAGCTTCAG

CGGAGCTTGGAGCCACCTCCAGGATCCCCTGGGGAGGCACCCCTAGCAGGAGCGGCCCCCTCGCTGCAAG

ATGAGGTGAGGGAGGCAGAGGCTGGGCGGCTTCGGACCCTTGAGAGGGAGAACCGGGAGCTTCGGGGGCT

GCTTCAGGTGCTTCAGGGGCAGCCAGGGGGCCAGCACCCCCTGCTGGAGGCACCGAGAGAGGACCCTGTT

CTTCCAGTGCTGGAGGAGGCTCCCCAGACTCCTGTGGCCTTCGACCACAGCCCTCAGGGCTTGGTTCAGA

AGGCAAGGGATGGAGGCCCCCAGGCCTTGGACTTGGCTCCCCCGGCATTAGACTCAGTGCTCGAGGCATC

AGCTGAGTGTCCCCAGGCACCTGATTCAGACCCACAGGAGGCAGAGAGTCCCCTTCAGGCAGCTGCCATG

GACCCCCAGGCCTCAGACTGGTCCCCGCAAGAGTCAGGCTCTCCTGTGGAGACACAGGAGTCCCCGGAGA

AGGCTGGCCGTAGATCCTCTCTCCAGAGCCCTGCCTCTGTGGCCCCACCTCAGGGTCCAGGGACCAAAAT

TCAGGCCCCGCAGTTGCTGGGAGGAGAGACAGAGGGAAGAGAGGCTCCCCAAGGCGAGTTGGTGCCTGAG

GCCTGGGGGTTGAGACAGGAGGGCCCTGAGCACAAGCCAGGGCCTTCGGAGCCCAGCTCTGTGCAGCTGG

AGGAGCAGGAGGGCCCAAACCAGGGCCTGGACCTGGCCACGGGACAAGCAGAGGCCAGAGAGCATGACCA

GAGGCTGGAAGGGACGGTCAGGGACCCAGCCTGGCAAAAACCACAGCAGAAGTCAGAAGGGGCTCTTGAG

GTCCAGGTCTGGGAAGGCCCAATCCCAGGGGAGAGCCTGGCCAGTGGTGTCGCAGAGCAGGAGGCCCTCA

GGGAGGAGGTGGCACAGTTGAGGAGAAAGGCTGAGGCCCTTGGAGATGAGCTGGAAGCCCAGGCCCGCAA

GCTGGAGGCCCAAAACACGGAGGCTGCCCGCCTCTCCAAGGAGCTGGCCCAAGCGCGAAGGGCAGAGGCC

GAGGCCCACCGGGAGGCAGAGGCCCAGGCCTGGGAGCAAGCCCGGCTGCGGGAGGCAGTGGAGGCTGCTG

GCCAGGAGCTGGAGTCTGCGTCCCAGGAACGGGAGGCGCTGGTGGAGGCGCTGGCAGCAGCGGGCCGGGA

GCGGAGGCAGTGGGAGCGTGAGGGGTCCAGGCTGCGGGCCCAGTCGGAGGCCGCCGAGGAACGGATGCAG

GTGCTGGAGAGCGAGGGCCGCCAGCACTTGGAGGAGGCTGAGAGGGAGCGCCGGGAGAAGGAGGCCCTCC

AGGCGGAGCTGGAGAAAGCTGTGGTGCGGGGCAAGGAGTTGGGGGACCGGCTGGAGCATTTGCAGCGTGA

GCTGGAGCAGGCGGCTCTCGAGCGCCAGGAATTTCTGCGAGAAAAGGAAAGCCAGCACCAGAGGTACCAG

GGCTTGGAGCAGCGGCTGGAAGCTGAGCTGCAGGCGGCGGCGACCAGCAAGGAGGAGGCGCTGATGGAGC

TCAAGACCAGGGCCCTGCAGCTGGAAGAGGAGCTGTTCCAGCTGCGCCAGGGCCCCGCGGGGCTGGGGCC

CAAAAAGCGTGCGGAGCCTCAGCTGGTGGAGACCCAGAATGTGCGGCTTATTGAGGTGGAGCGCAGTAAT

GCGATGCTGGTGGCAGAGAAGGCAGCTTTGCAGGGGCAGCTGCAGCACCTGGAGGGGCAGCTGGGGAGCC

TGCAGGGCCGTGCCCAGGAGCTGCTGCTGCAGAGCCAGCGGGCGCAGGAGCACAGCAGCCGCCTGCAGGC

CGAGAAGTCTGTGCTGGAGATTCAGGGCCAGGAGCTGCACCGGAAGCTGGAGGTGCTGGAGGAGGAGGTG

CGGGCGGCACGGCAGTCCCAGGAGGAGACCCGCGGGCAGCAGCAGGCCCTGCTTCGGGACCACAAGGCCC

TGGCACAGCTGCAGCGGCGGCAGGAGGCCGAGCTAGAGGGACTGCTGGTGCGGCACCGAGACCTCAAGGC

CAACATGCGGGCACTGGAGCTGGCCCACCGGGAGCTGCAGGGCCGGCACGAGCAGCTGCAGGCCCAGCGG

GCCAGCGTGGAGGCACAGGAGGTGGCCCTGCTGGCAGAGCGTGAACGCCTGATGCAAGATGGGCATCGGC

AGCGGGGCCTGGAGGAGGAGCTGCGGAGGCTTCAGAGCGAGCACGACAGGGCTCAGATGCTGCTGGCAGA

GTTGTCTCGGGAGCGGGGTGAGCTGCAGGGTGAACGCGGGGAGCTACGGGGCCGGCTGGCGCGGCTGGAG

CTGGAGCGGGCACAGCTGGAGATGCAGAGCCAGCAGCTGCGCGAGTCCAACCAGCAGCTGGACCTGAGCG

CCTGCCGGCTGACCACGCAGTGTGAGCTATTGACACAGCTGCGAAGTGCCCAGGAAGAGGAGAACCGGCA

GCTGCTGGCTGAAGTTCAGGCCCTGAGCCGGGAGAACAGGGAGCTCCTGGACGCGCAGCCTGGAGAGTCGG

GACCACCTGCACCGCGAACAGCGGGAGTACCTGGACCAGCTTAATGCCCTGCGCCGCGAGAAGCAGAAGC
```

-continued

```
TCGTGGAGAAGATCATGGACCAATACCGCGTGCTGGAGCCTGTGCCCCTGCCCCGGACCAAGAAGGGCAG

CTGGCTGGCAGACAAGGTGAAGAGGCTGATGCGGCCCCGGCGGGAGGGGGGCCCCCCTGGGGGGCTGCGC

CTGGGGGCCGATGGGGCTGGCAGCACCGAGAGCCTGGGGGGCCCCCCGGAGACGGAGCTTCCTGAGGGCA

GGGAGGCAGATGGGACAGGGTCCCCTTCCCCGGCACCCATGCGCCGGGCCCAGAGCTCCCTCTGCCTGCG

GGATGAGACCTTGGCAGGCGGGCAGCGGCGGAAACTCAGCTCAAGGTTCCCGGTGGGGCGAAGCTCTGAG

TCATTCAGCCCTGGGGACACCCCTAGGCAACGATTCCGACAGCGCCATCCAGGCCCCCTGGGGGCGCCCG

TCTCCCACAGCAAAGGACCTGGTGTGGGATGGGAGAACTCCGCTGAGACCCTGCAGGAACACGAAACAGA

TGCCAACCGAGAGGGCCCTGAGGTACAGGAACCGGAGAAACGTCCCCTCACCCCATCCCTCAGCCAGTGA

CACCGTGGGAACAGCAGGCTTGGGAGTGCAGCCTTCTCGGCACTGGAGTGTCAGCGGAGGCCCCAGGCAG

CCCAAGAGCTCAGGGAGCCAGGGACCCCAAGGGGAGTCCTTGGACAAGGAGGCCTGGGCCCTGAGATCCT

CCACGGTCAGCGCCGGGGCCCGGAGATGGAGCTGGGACGAGTGTGTGGACAGGGGGGATGGCTGGCCCCC

ACGAGCAGCTCCAGGCTGGAGTTCTGGTTCTTCCAGGTGGCTCCCGCTGAGGCAGCGGTCTCTGGGGGAT

CCCCCAGCTGAAGGAGGCTGGCAGGAGTTGGCAAGAGAACCCCCTGCCCTGTCCAGGTGGGAAGCTGAGT

CCCAGTGCTGGGGGACTGTGGCCTGGGCTGATCTTGAGCCTTAACTGGACATGAGGGGCATGAGAATAAA

GCTGAACTGCAGCCTCCTGAAAAAAAAAAAAA
```

>NM_020877.3*Homo sapiens* dynein axonemal heavy chain 2 (DNAH2), transcript variant 1, mRNA (SEQ ID NO: 7)

```
CTTCTACATCGCGAATATCCCTCGCCGGCCTGGCGCCCGGCGCCATCTGCTGGACCCGTTCCGGCTGGGG

CGCACAGACCTGGGCGCGGGGTCGGGCGATTGGGTTCTCCCTGCCTTTTCAATGTCCTGCGGGGCGGTGG

CTCACTGTCTCTCGCCCCAGCCCTTCCAGCTGGGTCCTGACACCAGGCCCCCCGCACCCTTCGGCTCGCC

AGATGTGGCTACTTTCCTTTAGTCCCGGAGCCTTCAAGCCCTGGGTCCCTGAGGGGTAGACCTGGGCGGG

GTGGGGCCGCGAAGCAGGGATCCAGGGCGCCTGCGCGGAGGAGGCGGGCTCCGAGGGGCCGCACACCGGC

CACTCGCCCCTCCCTGCCCGGGGTTGCCATGGGGACGCGTGCAGACGCCGGCCCGAGAGGGCTGCGAGGG

GCAACTTCTTAGAGTGGCCCATCGGTCGGTCTAGGGAGGGGAGGGTCAGCGTGGCAAGGTGTGTGTCGGG

GGCAGAGGGAAGGAGGGAAGGAGTGCTGGGGAGAAGGGGCAGTAGTGTCGGGGTAGGAAGGGACAGTTGT

TGGGGAGAAGAGGCAGTTGTGGAGGGAGAGGGAGCAAGGAATATTTGTGTGGGGGAGGGGGAGGAGAAGG

GGCAGTTGTGACAGCTGGGGGGGAAGAGCCATTCTGAGGGGAAATTTGCCTGCTGGTAACCAGTTTAAGG

ATACCAGCTGCTGGTATAAATACTGCTGGATAAATACTGCTGGATTTATACTGCAGGATAAATACTGCTG

GCCCCTGCGGTATTTCCTAGTACTAGAGTGAGCCCCGACTTAGCAGAGCAGTTCCTCCTGGGGCCTGCGG

TGTGGGATCGCGTGGTGAACCCCACGGTGCATGCGCCTCAGGCTCTAGTTTGAGGCAGGAAAGCGCAGCT

TGATGCTTCTCTGGAGACTGATGGAGGAAGCCTCCTTGCTGTAGTTGGTTTTATTGATTTGCTGGCCTAA

CAGAACGTTTTTCCTTGGAGCAAAGTACAAATCCTTCAAGTTTGAAATTCATAACCTGAGATCAATGCCT

GTGGCAGCCTGTGGGGATGAGGAAGGAGAGCCACAGGTGCCGTTAGGCTGCAGCCTAATGAAAAGAGAGT

GCCCAGCGCCTCAGACTTTGCGCCTGGGATTCTGAGCACCTGTCCGAGATCCCCGCTTCCTGCCATCCTA

CCTTTCTGAGAGAGGCACCACTGTGACCTTCCTCGTGCCCCAATTGCTTTTTCCTCATGACACAATTTGA

AATTTATGATTGGATGACTTTTGTCCTTCTTTCTTCCAATCTGTTCTCAGGGCATTTTGAGTCAAATAAA

TGATCCTGACTGATCTTAACCATTAGCACAGAGTTCCTCAGCCAACTCTGCTAAGAGACCTCAGTACACA

CAAAACAGTGTTCCTGCCCCTCAGGACTTCAAAGCGATAGACCCAGGTTTTGCCTGCACGATGTCCAGCA

AAGCTGAGAAGAAGCAGCGATTGAGTGGCCGAGGAAGCTCCCAGGCAAGCTGGTCAGGGCGGGCCACTCG

GGCTGCTGTGGCCACACAGGAGCAGGGGAATGCCCCGGCTGTCAGTGAGCCAGAGCTGCAGGCTGAGCTC

CCCAAGGAGGAGCCTGAGCCACGGTTGGAGGGACCTCAAGCACAGAGTGAAGAATCAGTGGAGCCCGAGG
```

-continued

```
CAGATGTGAAGCCCCTCTTCCTTTCCCGAGCTGCGCTGACAGGACTGGCGGATGCAGTGTGGACACAGGA

GCATGATGCCATTCTGGAACACTTTGCCCAGGACCCTACAGAATCCATCCTCACCATCTTCATTGACCCT

TGTTTTGGGCTGAAGCTAGAGCTGGGCATGCCTGTACAGACCCAGAACCAGCTTGTCTACTTCATTCGCC

AAGCACCAGTTCCCATCACCTGGGAGAACTTCGAGGCAACTGTGCAGTTTGGGACGGTGCGGGGCCCCTA

TATCCCGGCCCTGCTTCGGCTGCTCGGTGGAGTCTTTGCCCCTCAGATCTTTGCAAACACAGGCTGGCCT

GAGAGCATTAGAAATCATTTTGCTTCTCATCTGCACAAGTTCTTGGCCTGCCTGACAGACACTCGGTACA

AACTGGAGGGGCACACGGTCCTCTACATCCCTGCAGAGGCCATGAACATGAAGCCTGAGATGGTGATAAA

GGACAAAGAGCTGGTGCAACGGCTAGAGACCTCCATGATCCACTGGACCCGGCAGATAAAGGAGATGCTC

AGTGCCCAGGAGACTGTGGAGACAGGAGAAAATTTAGGTCCTCTGGAGGAGATTGAGTTCTGGCGCAACC

GATGCATGGACCTGTCTGGCATCAGTAAGCAGCTGGTGAAGAAGGGAGTGAAGCACGTTGAATCCATCCT

GCACCTTGCCAAGTCGTCCTACTTGGCGCCCTTTATGAAACTGGCACAGCAGATCCAGGATGGCTCTCGT

CAAGCACAGTCAAACCTGACCTTTTTGTCAATCCTGAAGGAACCTTACCAGGAGTTGGCTTTCATGAAGC

CCAAGGACATCTCTAGCAAGCTCCCTAAGCTGATCAGTCTCATCCGCATCATCTGGGTCAACTCTCCCCA

CTACAACACTCGGGAGAGACTGACCTCGCTCTTCCGAAAGGTATGTGACTGTCAGTATCACTTCGCCCGC

TGGGAAGATGGCAAGCAGGGTCCCCTTCCTTGCTTCTTTGGTGCCCAGGGGCCACAGATAACACGGAACT

TGCTGGAGATTGAGGACATCTTTCATAAAAATCTGCACACGCTGCGAGCCGTTCGCGGGGGTATCCTGGA

TGTCAAGAACACCTGTTGGCATGAAGACTACAATAAGTTCCGTGCCGGAATCAAGGACCTGGAGGTGATG

ACCCAGAACCTGATCACCTCAGCCTTCGAGTTGGTGCGGGACGTGCCGCACGGCGTGCTTCTGCTGGACA

CCTTCCACAGGCTTGCCTCCCGCGAGGCTATCAAGCGGACTTATGACAAGAAGGCGGTGGATCTCTACAT

GCTGTTCAATAGCGAGCTGGCCCTGGTGAACCGTGAACGGAACAAGAAATGGCCAGACCTGGAGCCCTAC

GTGGCCCAGTATTCCGGAAAGGCGCGCTGGGTGCACATCCTCCGGCGTCGCATCGACAGAGTCATGACCT

GCCTTGCTGGTGCTCATTTCCTGCCCCGTATTGGGACTGGAAAGGAGAGTGTGCACACCTATCAGCAGAT

GGTCCAGGCCATTGATGAGCTGGTTCGAAAAACCTTCCAAGAGTGGACATCAAGTCTGGACAAGGATTGC

ATTCGGCGGTTGGATACCCCATTGCTGCGAATCAGCCAGGAGAAGGCGGGCATGCTGGATGTCAACTTTG

ACAAGTCCCTTCTGATTCTCTTTGCGGAAATTGACTACTGGGAGCGGCTGCTGTTTGAGACGCCCCATTA

CGTGGTGAACGTAGCTGAGCGAGCCGAGGACCTGCGCATTCTGCGTGAAAATCTGCTACTCGTTGCTAGA

GACTACAATAGGATTATTGCCATGCTGTCCCCAGATGAGCAGGCCCTATTCAAAGAGCGTATTCGGCTCC

TGGATAAGAAGATCCACCCGGGACTCAAGAAACTGCACTGGGCCTTGAAGGGGGCCAGTGCCTTCTTCAT

CACGGAGTGCCGTATACATGCCAGCAAGGTGCAGATGATTGTGAATGAGTTCAAGGCATCCACTCTGACC

ATTGGCTGGCGAGCCCAAGAGATGTCAGAGAAGCTGCTGGTACGCATTAGTGGCAAACGGGTATACAGGG

ACCTGGAATTTGAAGAGGACCAAAGAGAGCATCGGGCAGCTGTACAGCAGAAATTGATGAACCTGCACCA

GGATGTGGTGACCATCATGACCAACTCCTATGAGGTCTTCAAGAATGATGGTCCTGAGATTCAGCAGCAG

TGGATGCTGTACATGATTCGGCTGGACCGCATGATGGAGGATGCCCTGCGCCTGAATGTGAAGTGGTCAC

TGCTAGAACTATCCAAGGCTATCAACGGGGATGGAAAGACCAGCCCAAACCCACTCTTCCAAGTCCTTGT

CATTTTGAAGAATGATCTGCAAGGAAGTGTGGCACAGGTGGAATTCTCACCCACTCTGCAGACTTTGGCA

GGTGTGGTCAATGACATTGGCAACCACCTCTTTTCCACCATCTCTGTCTTCTGCCACCTCCCTGACATTC

TCACCAAGCGCAAGTTACATCGTGAACCCATCCAAACAGTTGTGGAGCAAGATGAGGACATCAAGAAGAT

CCAGACCCAAATCAGCAGCGGCATGACTAACAACGCAAGCCTGCTGCAGAACTACCTCAAGACCTGGGAC

ATGTACCGGGAGATCTGGGAGATCAACAAGGACTCCTTCATTCATCGCTACCAGCGCCTCAACCCTCCTG

TCTCTTCTTTTTGTTGCCGACATTGCCCGCTACACGGAAGTTGCTAATAACGTGCAGAAGGAGGAGACAGT

CACCAACATCCAGTTTGTGCTGCTGGACTGTTCGCACCTCAAGTTCTCCCTGGTGCAGCACTGCAATGAA
```

-continued

```
TGGCAGAACAAGTTCGCGACTCTGCTCAGGGAGATGGCTGCTGGGCGCCTCCTGGAGCTGCACACCTACC

TGAAGGAGAACGCAGAGAAAATCAGCCGCCCTCCGCAGACACTGGAGGAACTGGGGGTCAGCTTGCAGCT

CGTGGATGCCCTGAAGCACGACTTGGCCAACGTGGAGACTCAGATCCCTCCCATACACGAGCAATTTGCC

ATTCTTGAAAAGTACGAGGTGCCAGTCGAGGACAGTGTCCTGGAGATGCTGGACAGTCTCAACGGGGAGT

GGGTTGTCTTCCAACAAACTCTGCTGGACAGTAAGCAAATGCTGAAGAAACACAAGGAGAAATTCAAGAC

AGGCCTGATCCACTCGGCAGATGACTTCAAGAAGAAAGCACATACACTTCTGGAAGATTTCGAATTCAAA

GGCCATTTCACCAGCAACGTGGGATACATGTCTGCCTTAGACCAGATTACACAAGTGCGGGCCATGCTGA

TGGCCATGCGGGAAGAGGAAAATAGTCTCCGAGCCAACCTGGGCATCTTCAAGATCGAGCAGCCACCCTC

CAAGGACCTTCAGAACCTGGAGAAGGAGCTCGATGCCCTCCAGCAAATCTGGGAGATCGCACGAGACTGG

GAGGAGAACTGGAATGAGTGGAAGACTGGCCGGTTCCTGATCCTGCAGACGGAAACCATGGAGACCACGG

CCCACGGGCTGTTTCGTCGCCTCACAAAATTAGCCAAAGAGTATAAGGACCGAAACTGGGAAATTATTGA

AACCACTCGCTCAAAAATAGAGCAGTTCAAGAGGACCATGCCTCTCATCTCAGACCTGCGGAACCCTGCC

CTTAGAGAGAGGCACTGGGACCAGGTCCGGGATGAGATCCAGCGGGAGTTTGATCAGGAATCTGAAAGCT

TCACCTTGGAGCAGATTGTGGAGCTTGGGATGGATCAGCATGTGGAGAAAATTGGGGAGATCTCTGCTTC

AGCAACTAAAGAGCTGGCTATAGAAGTGGCTTTACAAACATTGCCAAGACCTGGGATGTGACTCAGCTC

GACATAGTACCCTACAAGGATAAGGGCCATCATCGGCTCAGAGGTACAGAAGAAGTATTCCAGGCACTGG

AAGATAACCAGGTAGCTCTGTCTACCATGAAGGCATCACGCTTTGTCAAGGCCTTTGAGAAGGATGTGGA

CCACTGGGAACGCTGCCTCTCCCTCATTTTGGAGGTTATTGAGATGATTCTCACAGTGCAGCGTCAGTGG

ATGTACTTAGAGAATATCTTCCTAGGAGAAGACATCCGCAAGCAGCTGCCCAATGAATCGACCTTATTTG

ACCAGGTCAACAGCAACTGGAAAGCCATCATGGACAGGATGAACAAGGACAACAATGCTCTCCGGAGCAC

CCATCACCCAGGCCTCCTGGACACATTGATAGAAATGAATACAATCCTGGAAGATATTCAGAAATCTCTG

GATATGTATTTAGAGACCAAGCGACATATTTTCCCCCGCTTCTACTTCTTGTCCAATGATGACCTGCTGG

AGATTCTGGGCCAGTCCCGAAACCCAGAGGCTGTGCAGCCACACCTCAAAAAATGCTTTGACAACATCAA

GTTGCTGAGAATCCAGAAGGTTGGAGGGCCCAGCAGCAAATGGGAAGCTGTGGGGATGTTCTCGGGCGAC

GGCGAGTACATTGACTTCCTCCACTCAGTATTTTTAGAAGGCCCTGTGGAGTCCTGGCTTGGCGATGTGG

AACAGACCATGAGGGTGACCCTGCGGGACCTTCTCCGGAACTGCCACCTGGCCCTCAGGAAGTTCCTCAA

CAAGAGGGACAAATGGGTGAAGGAGTGGGCTGGCCAGGTGGTGATCACTGCCAGTCAGATCCAGTGGACG

GCTGATGTCACCAAGTGCCTGCTGACAGCGAAGGAGCGGGCAGACAAGAAAATCCTCAAGGTCATGAAGA

AGAACCAGGTGTCAATCCTGAATAAGTATTCAGAAGCCATCAGGGGGAACTTGACCAAGATCATGCGGCT

TAAAATTGTGGCTCTGGTGACGATAGAAATTCATGCCCGGGATGTGTTGGAGAAGCTTTACAAGAGTGGC

CTCATGGATGTCAATTCCTTTGACTGGCTCAGCCAACTTCGGTTCTACTGGGAGAAGGATCTTGATGACT

GTGTCATCCGCCAGACCAACACGCAATTTCAGTATAATTATGAGTACTTGGGTAACTCGGGCCGGCTCGT

CATCACCCCCCTGACGGACAGGTGTTACATGACACTGACCACGGCATTGCACCTGCACCGAGGGGGCTCC

CCCAAAGGCCCTGCAGGCACAGGCAAGACCGAGACCGTCAAGGACCTGGGCAAGGCCCTGGGCATATATG

TCATTGTGGTCAACTGCTCTGAGGGCCTGGACTACAAGTCCATGGGCCGAATGTACTCAGGTCTGGCCCA

GACTGGAGCTTGGGGCTGCTTTGATGAGTTTAACCGCATCAACATCGAGGTGCTGTCAGTGGTGGCCCAC

CAGATCCTGTGCATCCTGTCTGCCCTGGCTGCCGGCCTCACCCATTTCCATTTTGATGGCTTTGAAATAA

ATCTGGTGTGGTCCTGTGGGATCTTCATTACCATGAATCCTGGCTATGCTGGCCGCACAGAGCTTCCCGA

AAATCTTAAATCCATGTTCCGCCCAATTGCCATGGTGGTGCCTGACTCCACCCTCATTGCAGAAATCATT

CTCTTTGGAGAGGGCTTTGGCAACTGCAAGATTCTGGCCAAGAAGGTGTACACACTCTACTCACTGGCTG
```

-continued

```
TGCAGCAGCTGTCCAGACAGGACCACTATGACTTTGGCCTGCGTGCCCTCACCTCCCTTCTGCGCTATGC

TGGCAAGAAGCGCCGCCTACAGCCGGATCTGACTGATGAAGAGGTTCTGCTGCTCTCAATGAGAGATATG

AACATCGCCAAGCTCACTTCAGTTGATGCACCCCTGTTCAATGCCATCGTGCAAGATCTGTTTCCCAACA

TTGAGCTGCCTGTCATTGACTATGGCAAGCTGCGGGAGACCGTTGAGCAGGAGATTCGAGACATGGGCCT

GCAAAGCACGCCGTTCACCCTCACCAAGGTTTTCCAGTTGTATGAAACCAAGAACTCCCGCCACTCCACC

ATGATCGTGGGCTGCACGGGCAGCGGCAAGACTGCCTCATGGCGCATTCTACAGGCCTCCCTGTCCTCTC

TGTGCCGCGCCGGAGACCCTAACTTCAACATTGTTAGAGAGTTCCCTTTGAACCCCAAGGCATTGTCCCT

AGGGGAACTGTATGGGGAATATGACCTCAGCACCAATGAATGGACAGATGGCATCTTGTCCAGTGTCATG

CGGACGGCATGTGCAGATGAGAAACCCGACGAGAAGTGGATCCTGTTCGATGGCCCCGTGGACACACTGT

GGATCGAGAACATGAACTCCGTCATGGACGATAACAAGGTGTTGACCCTCATCAACGGCGAGCGCATCGC

GATGCCCGAGCAGGTGTCTCTCCTGTTTGAAGTGGAGGACCTGGCAATGGCCTCTCCGGCCACTGTATCC

CGCTGCGGGATGGTCTACACTGACTACGCTGACCTGGGCTGGAAGCCCTATGTTCAGTCATGGCTGGAGA

AGAGGCCAAAGGCTGAGGTGGAGCCCCTTCAACGCATGTTCGAAAAGCTCATCAACAAGATGCTGGCCTT

TAAGAAGGACAACTGCAAGGAGCTGGTGCCCCTGCCCGAGTACAGCGGTATCACCTCCCTCTGCAAGCTG

TACTCTGCCCTGGCCACGCCAGAGAATGGGGTGAACCCAGCTGACGGCGAGAACTATGTCACCATGGTAG

AGATGACATTTGTGTTCAGCATGATCTGGTCTGTGTGTGCCTCTGTGGATGAGGAGGGCCGGAAGAGGAT

CGACAGCTACCTCCGAGAGATCGAGGGCTCCTTTCCCAATAAGGACACGGTATATGAGTATTTTGTGGAC

CCCAAAATACGGAGTTGGACATCATTTGAGGACAAGCTCCCTAAGAGTTGGCGCTACCCTCCAAACGCCC

CCTTCTATAAGATCATGGTGCCCACCGTCGACACTGTTCGCTACAACTACCTGGTGAGCAGCTTGGTGGC

CAACCAGAATCCCATTCTGCTGGTGGGTCCCGTGGGGACTGGGAAGACCTCCATCGCCCAGAGCGTTCTG

CAGTCCCTGCCCTCCAGCCAGTGGTCGGTGCTCGTTGTCAACATGTCCGCACAGACCACATCCAATAACG

TGCAGAGCATCATTGAGAGCAGGGTTGAGAAGCGAACCAAGGGTGTCTACGTGCCATTCGGGGGCAAAAG

CATGATCACCTTTATGGATGACCTAAATATGCCCGCTAAGGACATGTTTGGGTCCCAGCCACCCCTGGAG

CTGATCCGCCTCTGGATTGACTATGGCTTCTGGTATGACCGTACGAAGCAGACCATCAAGTACATTCGAG

AAATGTTCCTGATGGCTGCCATGGGCCCCCCTGGGGGTGGACGGACTGTCATCTCCCCAAGGCTACGGAG

TCGCTTCAACATTATCAACATGACCTTCCCCACAAAGTCCCAGATCATCCGCATATTCGGCACCATGATC

AATCAGAAGCTTCAGGACTTTGAGGAAGAGGTGAAGCCCATTGGGAACGTGGTGACAGAGGCCACCCTGG

ACATGTACAACACCGTGGTACAGCGCTTCCTGCCCACGCCCACCAAGATGCATTACCTCTTCAACCTTCG

AGACATCTCCAAGGTGTTCCAGGGCATGCTTAGAGCCAACAAGGACTTCCATGATACCAAGTCCAGCATC

ACACGGCTCTGGATCCATGAATGTTTCAGAGTCTTCTCTGACCGGCTGGTTGATGCGGCAGACACAGAAG

CCTTCATGGGCATCATAAGCGACAAGCTCGGCTCCTTCTTTGACCTCACATTTCATCATCTCTGTCCCAG

CAAGCGTCCTCCTATCTTTGGGGATTTCCTGAAGGAGCCCAAGGTGTATGAAGACCTCACGGATCTGACA

GTGCTGAAGACAGTCATGGAGACAGCTCTAAATGAGTATAACCTGTCACCCTCTGTCGTGCCCATGCAGC

TAGTGCTCTTCCGAGAGGCTATTGAACACATCACACGGATCGTGCGGGTCATTGGACAGCCTCGGGGCAA

CATGCTCCTGGTGGGTATCGGGGGCAGCGGACGCCAGAGTCTGGCCCGCCTGGCTTCATCCATCTGCGAC

TACACCACCTTCCAGATCGAGGTCACCAAACATTATCGGAAGCAGGAGTTCCGAGATGATATCAAGCGTC

TGTATCGCCAGGCTGGGGTGGAGCTCAAGACCACGTCCTTCATTTTTGTGGACACCCAAATAGCTGATGA

GTCCTTCCTAGAGGACATCAACAACATCCTCAGCTCAGGCGAGGTGCCCAATCTCTACAAGCCTGATGAA

TTTGAAGAGATCCAGTCGCATATCATAGACCAGGCCCGGGTGGAGCAGGTGCCTGAGTCATCGGACAGCC

TCTTCGCCTACCTCATTGAACGCGTGCAGAACAACCTGCACATCGTGCTCTGCCTCAGCCCCATGGGGGA

TCCCTTCAGGAACTGGATCCGCCAGTACCCAGCCTTGGTGAACTGCACAACCATCAACTGGTTCTCAGAG
```

-continued

```
TGGCCCCAAGAGGCCCTGCTCGAGGTGGCTGAGAAGTGCCTCATAGGAGTAGACCTGGGAACTCAGGAGA

ATATCCACAGGAAGGTGGCCCAGATCTTTGTCACTATGCACTGGTCAGTAGCTCAGTATTCCCAGAAGAT

GCTGTTGGAACTGCGGAGACACAACTATGTCACACCCACCAAATACCTGGAACTCCTGTCTGGATATAAG

AAGTTGCTGGGAGAAAAACGGCAGGAGCTGCTGGCCCAAGCCAATAAACTGCGGACAGGCTTGTTCAAGA

TCGACGAAACTAGGGAAAAGGTGCAAGTGATGTCGTTGGAGCTGGAGGATGCCAAGAAGAAGGTGGCTGA

GTTCCAGAAGCAGTGTGAGGAGTACCTGGTCATCATTGTGCAGCAGAAGCGGGAGGCAGATGAGCAGCAG

AAGGCCGTAACAGCCAACAGTGAAAAGATTGCAGTTGAGGAAATCAAGTGTCAGGCACTGGCTGACAATG

CCCAGAAAGATCTAGAAGAGGCACTGCCCGCCCTGGAAGAGGCCATGCGGGCCCTGGAGTCTCTGAACAA

GAAGGATATAGGAGAGATCAAGTCTTATGGACGGCCCCCAGCCCAAGTGGAGATAGTGATGCAGGCAGTT

ATGATTCTTCGAGGCAACGAGCCCACATGGGCAGAGGCCAAGAGGCAGCTAGGGGAACAGAACTTCATCA

AGTCACTGATCAACTTTGATAAAGACAATATCTCAGATAAGGTTCTGAAGAAGATTGGGGCCTACTGCGC

CCAGCCTGACTTCCAGCCTGATATCATCGGCCGCGTCTCCCTGGCTGCCAAGTCCCTCTGCATGTGGGTG

CGGGCCATGGAGCTGTATGGGCGGCTATATCGGGTGGTGGAGCCCAAGCGAATCCGAATGAACGCTGCCT

TGGCTCAGCTTCGGGAGAAGCAAGCCGCGCTCGCTGAGGCCCAGGAGAAGCTGCGGGAGGTAGCTGAGAA

ACTGGAGATGCTAAAGAAACAGTATGATGAGAAGCTGGCACAGAAGGAGGAGCTTCGCAAGAAGTCTGAA

GAGATGGAGCTGAAGCTGGAGCGAGCTGGGATGCTCGTGTCGGGGTTGGCTGGCGAGAAGGCCAGATGGG

AGGAGACAGTCCAGGGCCTGGAGGAGGACCTGGGCTACCTGGTGGGGGACTGTCTCCTGGCAGCTGCCTT

CCTGTCCTACATGGGACCCTTCCTGACCAACTACCGGGATGAGATTGTCAACCAAATCTGGATCGGGAAG

ATCTGGGAGCTTCAGGTTCCTTGCTCCCCTTCTTTCGCCATCGATAACTTCCTGTGCAATCCTACCAAAG

TCCGGGACTGGAACATCCAAGGGGTTGCCCTCAGACGCCTTCTCCACTGAGAATGGCATCATCGTCACCCG

AGGCAACAGGTGGGCACTGATGATCGACCCTCAGGCCCAGGCCCTGAAATGGATTAAGAACATGGAAGGA

GGCCAGGGCCTGAAGATCATCGACCTGCAGATGAGCGATTACCTGCGAATCCTAGAACACGCCATTCACT

TTGGATACCCGGTGCTACTTCAGAACGTGCAGGAATATCTGGACCCCACACTGAACCCCATGCTCAACAA

ATCTGTAGCCCGAATCGGTGGTCGGCTGTTGATGCGCATTGGCGATAAGGAGGTGGAATATAATACCAAT

TTCCGTTTCTACATCACCACCAAGCTCTCCAACCCCCCACTACAGCCCAGAGACCTCAGCCAAGACCACCA

TCGTCAACTTTGCTGTTAAAGAACAGGGCCTGGAGGCCCAGCTGCTGGGCATTGTGGTGCGGAAGGAGCG

GCCTGAGCTGGAGGAGCAGAAGGACTCACTGGTCATCAACATCGCGGCTGGTAAAAGGAAGCTCAAGGAG

CTGGAGGATGAGATCCTGCGGCTGCTGAATGAGGCCACCGGCTCCCTGCTGGATGATGTGCAGCTGGTGA

ACACGCTGCATACCTCCAAGATCACAGCCACAGAGGTGACTGAGCAGCTGGAGACCAGTGAGACCACAGA

GATCAACACTGACTTGGCGCGGGAGGCTTACCGCCCCATGCGCCCAGCGGGCATCAATCCTGTTCTTCGTG

CTCAATGATATGGGCTGCATCGACCCCATGTACCAGTTCTCACTGGATGCCTACATCAGCCTCTTTATTC

TCAGCATTGACAAAAGCCACCGCAGCAATAAGCTGGAGGACCGCATTGACTACCTGAATGACTACCACAC

CTACGCTGTCTACAGGTACACCTGCCGTACCCTTTTCGAACGCCACAAACTACTATTCAGTTTTCATATG

TGTGCCAAAATCTTGGAGACTTCTGGCAAGCTCAACATGGATGAATACAACTTCTTTCTACGTGGGGGTG

TGGTCTTGGATCGGGAGGGCCAAATGGACAATCCATGTAGTAGCTGGCTTGCAGATGCCTACTGGGATAA

CATCACAGAGCTAGACAAACTGACCAACTTCCACGGACTCATGAACTCCTTTGAGCAGTACCCTCGTGAC

TGGCACCTGTGGTATACCAATGCTGCCCCGGAGAAGGCGATGCTGCCAGGTGAGTGGGAAAATGCCTGCA

ATGAAATGCAACGGATGCTGATCGTTCGCTCCCTGCGCCAGGACCGCGTGGCCTTCTGCGTGACCTCCTT

CATCATCACCAACCTTGGCTCCCGCTTCATCGAGCCGCCTGTGCTGAATATGAAGTCGGTGCTGGAGGAT

TCAACCCCACGATCCCCACTCGTGTTCATCCTGTCCCCTGGTGTGGACCCCACCAGTGCCCTGCTGCAGC
```

-continued

```
TGGCAGAGCACATGGGCATGGCCCAGCGCTTCCACGCCCTGTCCCTGGGCCAGGGCCAGGCCCCCATCGC

TGCTCGGCTCCTCCGAGAGGGTGTGACTCAGGGACACTGGGTGTTCCTGGCAAACTGCCACCTGTCACTG

TCTTGGATGCCTAATCTGGACAAGCTGGTGGAGCAGCTGCAGGTGGAGGATCCTCATCCATCCTTCCGCC

TCTGGCTCAGCTCCATCCCCCACCCAGACTTCCCTATCTCAATCTTGCAGGTCAGCATCAAGATGACCAC

AGAGCCACCAAAGGGCCTAAAGGCCAACATGACACGTCTTTACCAACTGATGTCAGAACCACAGTTTTCC

CGCTGCTCCAAACCTGCCAAATATAAGAAGCTGCTGTTTTCACTCTGTTTCTTCCACTCTGTGTTACTTG

AACGCAAAAAGTTCCTGCAGCTTGGCTGGAACATCATCTATGGCTTCAATGACTCCGACTTTGAGGTGTC

AGAAAACTTGCTGAGCCTCTATCTCGATGAGTACGAGGAGACACCTTGGGACGCACTTAAGTACCTCATT

GCCGGCATCAACTATGGTGGACATGTCACAGATGACTGGGACCGGCGCCTGCTGACCACCTACATCAATG

ATTATTTCTGTGACCAGTCTCTATCAACTCCCTTCCACCGGTTGTCAGCACTGGAGACTTATTTCATCCC

CAAGGATGGCAGCCTCGCTTCTTACAAGGAATACATCAGCTTATTGCCTGGCATGGACCCCCCTGAGGCC

TTTGGCCAGCACCCCAATGCTGATGTGGCCTCTCAGATCACTGAGGCACAAACCCTCTTTGATACTTTGC

TTTCCTTGCAACCTCAGATTACACCCACCAGGGCTGGAGGCCAGACCCGGGAAGAGAAGGTCCTTGAGTT

GGCCGCTGATGTGAAGCAGAAGATCCCTGAAATGATCGACTATGAGGGGACTCAAAAACTGCTAGCTCTC

GACCCCTCCCCCCTCAATGTGGTCCTTCTGCAGGAGATCCAGAGATACAACACACTGATGCAGACCATCC

TGTTCTCACTGACAGACCTAGAGAAAGGCATCCAGGGTCTCATCGTCATGTCTACAAGCCTGGAAGAGAT

TTTCAATTGCATCTTTGATGCCCATGTTCCTCCGCTCTGGGGAAAGGCATACCCCTCACAAAAGCCATTG

GCTGCCTGGACCCGGGACTTGGCCATGCGTGTGGAGCAGTTTGAGCTGTGGGCCAGCCGGGCCCGGCCTC

CTGTGATCTTCTGGTTGTCTGGTTTCACCTTTCCCACTGGCTTCCTCACTGCTGTGCTGCAGTCTTCAGC

TCGCCAAAACAACGTTTCAGTGGACAGCCTCTCCTGGGAGTTTATCGTTTCCACTGTGGATGACAGCAAC

CTAGTGTATCCCCCCAAGGATGGTGTCTGGGTCCGGGGCCTGTACCTGGAAGGTGCTGGCTGGGACCGGA

AGAACTCCTGCTTGGTGGAGGCAGAGCCCATGCAGCTTGTCTGCCTCATGCCCACGATCCACTTCCGGCC

TGCAGAGAGCCGCAAGAAGAGCGCCAAGGGCATGTACTCCTGCCCCTGCTATTACTATCCCAACCGGGCA

GGCAGCTCAGACCGAGCCTCCTTTGTCATCGGCATTGACCTGCGGTCTGGGGCCATGACACCTGATCATT

GGATCAAGAGGGGCACTGCTCTACTCATGAGCCTGGACAGCTGAGACCTCCTCCTCTTCTCCGCTTGAGA

GAGAGGGTCAGGGACTCCAGGAGCTAAGACAGATGTTGCACCTAGGACTGAGGCCGGACCTCACTCAGAC

TTTGACCTTGGCCGAATTTGTGTGATGTGGCCCTGGAGATACCTAGTTGTGTTAGCCATAAAAGTGAAAG

AGTTGTATTGGAGCTCAGTGCTGTAAAACACCCGCGACAACAAGC
```

>NM_000719.6*Homo sapiens* calcium voltage-gated channel subunit alpha1 C
(CACNA1C), transcript variant 18, mRNA (SEQ ID NO: 8)

```
TTATTTTTTCAAATGGTGTAGCCGCCGGAGGTGCGGTGCTCAGTTCTTGGAAGGGGCCCGGATGTACTGA

GGATGCGTTACAGTTTCACTCGAGGAGGCAGTAGTGGAAAGGAGCAGTTTTTGGGGTTTGATGCCATAAT

GGGAATCAGGTAATCGTCGGCGGGGAAGAAGAAACGCTGCAGACCACGGCTTCCTCGAATCTTGCGCGAA

AGCCGCCGGCCTCGGAGGAGGGATTAATCCAGACCCGCCGGGGGGTGTTTTCACATTTCTTCCTCTTCGT

GGCTGCTCCTCCTATTAAAACCATTTTTGGTCCATGGTCAATGAGAATACGAGGATGTACATTCCAGAGG

AAAACCACCAAGGTTCCAACTATGGGAGCCCACGCCCGCCCATGCCAACATGAATGCCAATGCGGCAGC

GGGGCTGGCCCCTGAGCACATCCCCACCCCGGGGGCTGCCCTGTCGTGGCAGGCGGCCATCGACGCAGCC

CGGCAGGCTAAGCTGATGGGCAGCGCTGGCAATGCGACCATCTCCACAGTCAGCTCCACGCAGCGGAAGC

GGCAGCAATATGGGAAACCCAAGAAGCAGGGCAGCACCACGGCCACACGCCCGCCCCGAGCCCTGCTCTG

CCTGACCCTGAAGAACCCCATCCGGAGGGCCTGCATCAGCATTGTCGAATGGAAACCATTTGAAATAATT

ATTTTACTGACTATTTTTGCCAATTGTGTGGCCTTAGCGATCTATATTCCCTTTCCAGAAGATGATTCCA
```

-continued

```
ACGCCACCAATTCCAACCTGGAACGAGTGGAATATCTCTTTCTCATAATTTTTACGGTGGAAGCGTTTTT

AAAAGTAATCGCCTATGGACTCCTCTTTCACCCCAATGCCTACCTCCGCAACGGCTGGAACCTACTAGAT

TTTATAATTGTGGTTGTGGGGCTTTTTAGTGCAATTTTAGAACAAGCAACCAAAGCAGATGGGGCAAACG

CTCTCGGAGGGAAAGGGGCCGGATTTGATGTGAAGGCGCTGAGGGCCTTCCGCGTGCTGCGCCCCCTGCG

GCTGGTGTCCGGAGTCCCAAGTCTCCAGGTGGTCCTGAATTCCATCATCAAGGCCATGGTCCCCCTGCTG

CACATCGCCCTGCTTGTGCTGTTTGTCATCATCATCTACGCCATCATCGGCTTGGAGCTCTTCATGGGGA

AGATGCACAAGACCTGCTACAACCAGGAGGGCATAGCAGATGTTCCAGCAGAAGATGACCCTTCCCCTTG

TGCGCTGGAAACGGGCCACGGGCGGCAGTGCCAGAACGGCACGGTGTGCAAGCCCGGCTGGGATGGTCCC

AAGCACGGCATCACCAACTTTGACAACTTTGCCTTCGCCATGCTCACGGTGTTCCAGTGCATCACCATGG

AGGGCTGGACGGACGTGCTGTACTGGGTCAATGATGCCGTAGGAAGGGACTGGCCCTGGATCTATTTTGT

TACACTAATCATCATAGGGTCATTTTTTGTACTTAACTTGGTTCTCGGTGTGCTTAGCGGAGAGTTTTCC

AAAGAGAGGGAGAAGGCCAAGGCCCGGGGAGATTTCCAGAAGCTGCGGGAGAAGCAGCAGCTAGAAGAGG

ATCTCAAAGGCTACCTGGATTGGATCACTCAGGCCGAAGACATCGATCCTGAGAATGAGGACGAAGGCAT

GGATGAGGAGAAGCCCCGAAACATGAGCATGCCCACCAGTGAGACCGAGTCCGTCAACACCGAAAACGTG

GCTGGAGGTGACATCGAGGGAGAAAACTGCGGGGCCAGGCTGGCCCACCGGATCTCCAAGTCAAAGTTCA

GCCGCTACTGGCGCCGGTGGAATCGGTTCTGCAGAAGGAAGTGCCGCGCCGCAGTCAAGTCTAATGTCTT

CTACTGGCTGGTGATTTTCCTGGTGTTCCTCAACACGCTCACCATTGCCTCTGAGCACTACAACCAGCCC

AACTGGCTCACAGAAGTCCAAGACACGGCAAACAAGGCCCTGCTGGCCCTGTTCACGGCAGAGATGCTCC

TGAAGATGTACAGCCTGGGCCTGCAGGCCTACTTCGTGTCCCTCTTCAACCGCTTTGACTGCTTCGTCGT

GTGTGGCGGCATCCTGGAGACCATCCTGGTGGAGACCAAGATCATGTCCCCACTGGGCATCTCCGTGCTC

AGATGCGTCCGGCTGCTGAGGATTTTCAAGATCACGAGGTACTGGAACTCCTTGAGCAACCTGGTGGCAT

CCTTGCTGAACTCTGTGCGCTCCATCGCCTCCCTGCTCCTTCTCCTCTTCCTCTTCATCATCATCTTCTC

CCTCCTGGGGATGCAGCTCTTTGGAGGAAAGTTCAACTTTGATGAGATGCAGACCCGGAGGAGCACATTC

GATAACTTCCCCCAGTCCCTCCTCACTGTGTTTCAGATCCTGACCGGGGAGGACTGGAATTCGGTGATGT

ATGATGGGATCATGGCTTATGGCGGCCCCTCTTTTCCAGGGATGTTAGTCTGTATTTACTTCATCATCCT

CTTCATCTGTGGAAACTATATCCTACTGAATGTGTTCTTGGCCATTGCTGTGGACAACCTGGCTGATGCT

GAGAGCCTCACATCTGCCCAAAAGGAGGAGGAAGAGGAGAAGGAGAGAAAGAAGCTGGCCAGGACTGCCA

GCCCAGAGAAGAAACAAGAGTTGGTGGAGAAGCCGGCAGTGGGGGAATCCAAGGAGGAGAAGATTGAGCT

GAAATCCATCACGGCTGACGGAGAGTCTCCACCCGCCACCAAGATCAACATGGATGACCTCCAGCCCAAT

GAAAATGAGGATAAGAGCCCCTAGCCCAACCCAGAAACTACAGGAGAAGAGGATGAGGAGGAGCCAGAGA

TGCCTGTCGGCCCTCGCCCACGACCACTCTCTGAGCTTCACCTTAAGGAAAAGGCAGTGCCCATGCCAGA

AGCCAGCGCGTTTTTCATCTTCAGCTCTAACAACAGGTTTCGCCTCCAGTGCCACCGCATTGTCAATGAC

ACGATCTTCACCAACCTGATCCTCTTCTTCATTCTGCTCAGCAGCATTTCCCTGGCTGCTGAGGACCCGG

TCCAGCACACCTCCTTCAGGAACCATATTCTGTTTTATTTTGATATTGTTTTTACCACCATTTTCACCAT

TGAAATTGCTCTGAAGATGACTGCTTATGGGGCTTTCTTGCACAAGGGTTCTTTCTGCCGGAACTACTTC

AACATCCTGGACCTGCTGGTGGTCAGCGTGTCCCTCATCTCCTTTGGCATCCAGTCCAGTGCAATCAATG

TCGTGAAGATCTTGCGAGTCCTGCGAGTACTCAGGCCCCTGAGGGCCATCAACAGGGCCAAGGGGCTAAA

GCATGTGGTTCAGTGTGTGTTTGTCGCCATCCGGACCATCGGGAACATCGTGATTGTCACCACCCTGCTG

CAGTTCATGTTTGCCTGCATCGGGGTCCAGCTCTTCAAGGGAAAGCTGTACACCTGTTCAGACAGTTCCA

AGCAGACAGAGGCGGAATGCAAGGGCAACTACATCACGTACAAAGACGGGGAGGTTGACCACCCCATCAT

CCAACCCCGCAGCTGGGAGAACAGCAAGTTTGACTTTGACAATGTTCTGGCAGCCATGATGGCCCTCTTC
```

-continued

```
ACCGTCTCCACCTTCGAAGGGTGGCCAGAGCTGCTGTACCGCTCCATCGACTCCCACACGGAAGACAAGG

GCCCCATCTACAACTACCGTGTGGAGATCTCCATCTTCTTCATCATCTACATCATCATCATCGCCTTCTT

CATGATGAACATCTTCGTGGGCTTCGTCATCGTCACCTTTCAGGAGCAGGGGGAGCAGGAGTACAAGAAC

TGTGAGCTGGACAAGAACCAGCGACAGTGCGTGGAATACGCCCTCAAGGCCCGGCCCCTGCGGAGGTACA

TCCCCAAGAACCAGCACCAGTACAAAGTGTGGTACGTGGTCAACTCCACCTACTTCGAGTACCTGATGTT

CGTCCTCATCCTGCTCAACACCATCTGCCTGGCCATGCAGCACTACGGCCAGAGCTGCCTGTTCAAAATC

GCCATGAACATCCTCAACATGCTCTTCACTGGCCTCTTCACCGTGGAGATGATCCTGAAGCTCATTGCCT

TCAAACCCAAGCACTATTTCTGTGATGCATGGAATACATTTGACGCCTTGATTGTTGTGGGTAGCATTGT

TGATATAGCAATCACCGAGGTAAACCCAGCTGAACATACCCAATGCTCTCCCTCTATGAACGCAGAGGAA

AACTCCCGCATCTCCATCACCTTCTTCCGCCTGTTCCGGGTCATGCGTCTGGTGAAGCTGCTGAGCCGTG

GGGAGGGCATCCGGACGCTGCTGTGGACCTTCATCAAGTCCTTCCAGGCCCTGCCCTATGTGGCCCTCCT

GATCGTGATGCTGTTCTTCATCTACGCGGTGATCGGGATGCAGGTGTTTGGGAAAATTGCCCTGAATGAT

ACCACAGAGATCAACCGGAACAACAACTTTCAGACCTTCCCCCAGGCCGTGCTGCTCCTCTTCAGGTGTG

CCACCGGGGAGGCCTGGCAGGACATCATGCTGGCCTGCATGCCAGGCAAGAAGTGTGCCCCAGAGTCCGA

GCCCAGCAACAGCACGGAGGGTGAAACACCCTGTGGTAGCAGCTTTGCTGTCTTCTACTTCATCAGCTTC

TACATGCTCTGTGCCTTCCTGATCATCAACCTCTTTGTAGCTGTCATCATGGACAACTTTGACTACCTGA

CAAGGGACTGGTCCATCCTTGGTCCCCACCACCTGGATGAGTTTAAAAGAATCTGGGCAGAGTATGACCC

TGAAGCCAAGGGTCGTATCAAACACCTGGATGTGGTGACCCTCCTCCGGCGGATTCAGCCGCCACTAGGT

TTTGGGAAGCTGTGCCCTCACCGCGTGGCTTGCAAACGCCTGGTCTCCATGAACATGCCTCTGAACAGCG

ACGGGACAGTCATGTTCAATGCCACCCTGTTTGCCCTGGTCAGGACGGCCCTGAGGATCAAAACAGAAGG

GAACCTAGAACAAGCCAATGAGGAGCTGCGGGCGATCATCAAGAAGATCTGGAAGCGGACCAGCATGAAG

CTGCTGGACCAGGTGGTGCCCCCTGCAGGTGATGATGAGGTCACCGTTGGCAAGTTCTACGCCACGTTCC

TGATCCAGGAGTACTTCCGGAAGTTCAAGAAGCGCAAAGAGCAGGGCCTTGTGGGCAAGCCCTCCCAGAG

GAACGCGCTGTCTCTGCAGGCTGGCTTGCGCACACTGCATGACATCGGGCCTGAGATCCGACGGGCCATC

TCTGGAGATCTCACCGCTGAGGAGGAGCTGGACAAGGCCATGAAGGAGGCTGTGTCCGCTGCTTCTGAAG

ATGACATCTTCAGGAGGGCCGGTGGCCTGTTCGGCAACCACGTCAGCTACTACCAAAGCGACGGCCGGAG

CGCCTTCCCCCAGACCTTCACCACTCAGCGCCCGCTGCACATCAACAAGGCGGGCAGCAGCCAGGGCGAC

ACTGAGTCGCCATCCCACGAGAAGCTGGTGGACTCCACCTTCACCCCGAGCAGCTACTCGTCCACCGGCT

CCAACGCCAACATCAACAACGCCAACAACACCGCCCTGGGTCGCCTCCCTCGCCCCGCCGGCTACCCCAG

CACGGTCAGCACTGTGGAGGGCCACGGGCCCCCCTTGTCCCCTGCCATCCGGGTGCAGGAGGTGGCGTGG

AAGCTCAGCTCCAACAGGTGCCACTCCCGGGAGAGCCAGGCAGCCATGGCGGGTCAGGAGGAGACGTCTC

AGGATGAGACCTATGAAGTGAAGATGAACCATGACACGGAGGCCTGCAGTGAGCCCAGCCTGCTCTCCAC

AGAGATGCTCTCCTACCAGGATGACGAAAATCGGCAACTGACGCTCCCAGAGGAGGACAAGAGGGACATC

CGGCAATCTCCGAAGAGGGGTTTCCTCCGCTCTGCCTCACTAGGTCGAAGGGCCTCCTTCCACCTGGAAT

GTCTGAAGCGACAGAAGGACCGAGGGGGAGACATCTCTCAGAAGACAGTCCTGCCCTTGCATCTGGTTCA

TCATCAGGCATTGGCAGTGGCAGGCCTGAGCCCCCTCCTCCAGAGAAGCCATTCCCCTGCCTCATTCCCT

AGGCCTTTTGCCACCCCACCAGCCACACCTGGCAGCCGAGGCTGGCCCCCACAGCCCGTCCCCACCCTGC

GGCTTGAGGGGGTCGAGTCCAGTGAGAAACTCAACAGCAGCTTCCCATCCATCCACTGCGGCTCCTGGGC

TGAGACCACCCCCGGTGGCGGGGGCAGCAGCGCCGCCCGGAGAGTCCGGCCCGTCTCCCTCATGGTGCCC

AGCCAGGCTGGGGCCCCAGGGAGGCAGTTCCACGGCAGTGCCAGCAGCCTGGTGGAAGCGGTCTTGATTT
```

-continued

```
CAGAAGGACTGGGGCAGTTTGCTCAAGATCCCAAGTTCATCGAGGTCACCACCCAGGAGCTGGCCGACGC

CTGCGACATGACCATAGAGGAGATGGAGAGCGCGGCCGACAACATCCTCAGCGGGGGCGCCCCACAGAGC

CCCAATGGCGCCCTCTTACCCTTTGTGAACTGCAGGGACGCGGGGCAGGACCGAGCCGGGGGCGAAGAGG

ACGCGGGCTGTGTGCGCGCGCGGGGTCGACCGAGTGAGGAGGAGCTCCAGGACAGCAGGGTCTACGTCAG

CAGCCTGTAGTGGGCGCTGCCAGATGCGGGCTTTTTTTTATTTGTTTCAATGTTCCTAATGGGTTCGTTT

CAGAAGTGCCTCACTGTTCTCGTGACCTGGAGTTAACCGGAACAGCGTCTTCATTCATTTCTGTTGGGAC

CAGACGCGGAGCCTGGGTGCGCGAGCCGCCCTCCGGGAGGAAGGCGCCCGGCTGCGTCTGCAGAGGCGGG

GAGAGGAGGCGGCGAGGGTCCCGGGGCGCGAGGAAGGCGCCTGCCCTCTCCCAGCTCGCAGGCCCCGGGC

CCGGCCGCGCCTCCGCGGGGAGAGCACCCCGGCTTCCCGCGCGCCCTCACCAAAAGGACCCTACAGCAAA

CGGGTGTCTTTCGACTCTGCTTGTAGAAACCATTTGCACATATTCTGTACGAGCCTCGCTGTCTCCCTAG

AGCCAGGGCCCTGCGGATTTGGAGAAGGGAGCGGGGCAGGACTTCCAGGAGGACCCCAACCCGGCCCGGA

GAGGGAGGAGGAGGCCTCCAGGGGCGCGGAGCTCTGGGGATGGGCGTCGGGCCGGCAGTGGTGCGGCTCA

CTCCGTCCCTGCCCACCTGCGACGGGATCCCCCGACCGGCACGGGCCACGCCGAGCTCCCGGCCAGCCGC

CGGCCCGCAGGCAGCGCGAGGGAGGAGCTGCGCCGCCGGCTCCGCCCAACCAGGTGGTGCTGAGCTTCCG

CTGAGCGCTCTTTTGTTTTGTGGTTTGACACTTTTCTTGACAGCATGTTGCAGTTTCTTTTCGGTTTTGG

TTTTTTTTAAATGTTTTATTTTGCTTTCCCAGCGGGAGGGGAGGAAGAAGAGTGTTTACAAAGTCCTGTA

GCCCCCTCACCTTTCTGTTTTCACTTTTGCCAATGTACATCGGGTTTGGTTTTCTTGTATTATTTAAACG

GTTGTGGTTTCCTTTTTCCACGGAGGTTCAATAGAAGCCGCTGCAGGAGAGTTTTACCAACCATTGTGTA

TGCCCAATAATTTGTTATCATTTCCTTAGGTAGTAACCTATTTTTGTTCTGGTTTGGTTCGGTTATCTAA

TGGAAAGGTAACTGGCAATGCACTTGATGTGGTCTTGCACATGTGGGTGATAGAGTTGGGTTCCTTTTTA

TGCTGGGTGTACAGGTGGGTTTGGGAGAGAGGAGCATGCGCGAGAGAGTCTCCGAGTGTGTGCGACGCGT

GTGTGTGTGGTGGGTTGTCTGTGTGCATATGTCCTGCCCGTGTATATGCACCCACACCATGTGCCCGTGC

ACACCAGTGACTACGCAGTCCCCCCTTTCTGGTTTAGCTGTGGGAAGATCTGAATCTGGGGCCGTTTGAA

AGCAAAAACAAACCACTGTCTCTGCTTCTGAAACGGGAATCAGTAACTCTTTGCATTTTCTGTCCCACAA

GATATGCAAAAACAATGCAATAATATTCATTTAAAAATACAATTGTGAGTTGTGTTGGCATTAAAACTGT

ATTTTAAAAAAAGACAGAAATTTAAGGGAAAAACACAAGAAGGCATTTTGCTTCAATATATTCCGTGTAA

TGTTTTATTGCATTGATAATGTTTCTGTTGAAGAAACCGTTATACTTGAATTCAGGTCAGTTTCAGTATT

TTTCAAATATTTTTTTAAAACTGAATTGCAATTGTGCCAAGCGAATATAATGAATTGAATTAAGTTGGTT

TTCGGATTCACTTCTTGTATATTTTGCTGCATGTAAAGTAAATCATTTTGTATTTGGAGTGTGACAAGCT

TTACCTTTGAACTCAAGTGCTTTTCTATATGTGGTTGGGGGAAAGGGAACAAGTTTTCTTTAGTTTGCAC

AATGAGCAAAGGTATCACCAGTGTAGTCATTATTCTGCTCTCCACAAACAGGTTTGGACATTACTGTTTT

GCATATCTTGTGTTTGCTTACATTTCCCTCAATTTTTCCAAAATCGTTTGCTGGGTATGTTTGTACCGCC

TCTTGCTGTGAGAGACCAGGACCTATTTTATTCCAGTCTTCACTCTGTCCACTCTGCTCTGGTCATCTGA

TTTGGTACTTCTCCAAGAACAGCCCTTCACTGTGAGGTGCAGGGAGGCGTTCTGATGAGCCCTCAGTCAC

TGGGCCGTCATCCGCATCCCCCATGGAAGAGGTAGCTGGCTTTCCCTTCCCTTCCACCACACGGAATTTT

CTCTTTGGCTTCCTTAGGAAAGTGTACACTAACCGGGAGGATAAAATTAAAGTCAGGCTGCTTGGAGGGA

GGGGCATCCTCACTTCCGGATTCTTGTTGCTCTACCCAACAAGGACAGCAGGGGCTCGAGAAAGGAACTG

GTGAAACCCTGATCCATCTGAAAGTCAACTCTGCGTGCTCCTTTCTCCATCCCTTCCTCACTCTGGAGCA

GCCTTTCCTTCAGGCTTGCCCTAATGTTTGGGCTGCCGGGGAGGGGGCCAGGACAAGGGAAGAGGCATCC

GGAGCTCACAGTGGGGGTGGGAACAGATTTTTGTGGGGGCATCTCTAATGCTCACTTATATCTCCCTAGA

ACATCACTCTTTTGGTGCTGTGTCCTTCAAATGTATGTCAACAGTGGTGGCTGAAAAGGGACTGCTTTGG
```

-continued

```
GGAAAACAGGACCCAACCATTCACCCAGAATTGACCCATTAAATCTCTTCCAGTCCTAGTGTTCCCTGAG

CCCCTCTTGGCACATATATAAGTAAGCTAGAAATTACAATAAGGGACAGTCCATTCCTCTATGACAGCTT

GCTGGACTGATTCATGACAAAGTGGAGAAATGTACTCAATACTCCCCGGTTAACACAGTCTAGAAACAGA

GTTTCTTTATGGATATCCACACCCAAGTCATCCAAACTTTCTTGATTCCTTTTCACTGCCATCAAGGTCC

TCTAGAAATTGAGTTTAGGTATCATCCTTTGAAAAGTTCCCAAGATTTCTACCAGGAGGTACACACAGGC

GTTCCCTGTCTAGGGCAGGAGGACTATCCTAGCTTGACCTTCTGATCCACTAGAATAAGACTGGCGTATG

ATGCCTGTCATCAGAACAGACTGGCACAAGTAGTGACATCAATGAACCACAGCACAATCTTCCAAGTGAT

GTCTACTCTCCACCTAAAATGGAATTTTCCCCATGACCTTGTAAAACATAATTGTCACATCTTCCATACC

CCTCCTGACAGCCCCCAAGTGTCAGGAGAAACAGTCAGGGGCTAAGGGCCCAAGGGACTTGAAGAAACA

ACAGTTTAAGGTCTGCAGTTTGGTCAACTTAATTCTTGTCCTCCGACCAGCCCTGCCTCTTTCATTTCCA

GACCTTGGAGAATTTTTCCCAGCTTTGATTCAGAAGGTACTAGTTATAACCCCTTTCCTTCTTCTTAATC

CAATAGGCCTCACTCTCACTGGGAAATCCACTCAAAGGAACAAGGCAATGTCTCTCATTCTATTTCCCAG

TTCCAAATTCCAGGTGCTTGTCTGGAGTGAAGCTACCCGTTACTTTCTCCCAGCTTTTCTCCACCCAGCA

TGTCTCCTGCCCATGCAGCTGAAGACAGTGGGGCAACCTCAGGAGAAGCAGACCTTTCCATGCCCAAGTT

CATCTCCTGAGCAACAGTGACACCTAGAAAATGAGGACTTTGGAAGTCACCCAAAAGATGGTGGCTACTT

TATGGAGTCCTGAAGATACACAGCCACCACTCCTAAAGGCAAAGAAAGAAAACACGAATGTAGGTCAGGG

ATAGAGTGGAACCCTGGTCATCGGGGTTTTTAGCCTCATCGTGGGAAAGGTGGTAAAGGAGGATGATGGC

ATCTCCATCCCTAGAGGCCAAGAATTGAAATATCATTGTCAAGGATTAGAAACAATTCAGCAAAGAGGCC

ACAAAAAGGGCCTGCTGACTCCCAGAAGACCTCTTTAAACCCCAGGGGAGGCAAATACTTGCTGATGGAG

TCTGGGCCGTTTCCATATTTTAAAGAAGACCTGCCTCTGGGGCAAATGTCAGCACAGAGAGGACTGGGAG

GAGAATGGAGGCAAGAAAAGGGCATATTTTGACTCCCTCTGTGCCTCTTCCCAGTTCATGGAAGGATGTG

TTCAGCTTACCCACCCACAGTGACCAGTGTGGTGGAGCCGCTGACATCTCAAGGATCTATTTGGGAAGGT

GAGAAGAGTACTCATTCCATCTGGGGGTGTTGTTCCAGCCACATCAGCCTACCTGGTGGGATGTGGGGGT

GTCTGCCACCCTGTCCCCCCTCTGCTGATGTCCCTCCCCTCAGGCTGTCCAGGTGCCACCTGACACAGGC

TGCTGTGCAAAGACAGGCGGGGAAGCCCAAACCTCACTCCCAGGGAGGCCCTCAGCCGCCAGAGTCCAGG

TTCTCCAGAGGCTACGATTTGAGGAGGTTGAGGGGGAAGACAGGAGGGAAAGAAAAGTCCTACAACTGTC

AGGAATGGGGCACCTTTCCCTGTCCCTAAGCAAAGCTCCCTCTTCCCACTGCCCTCCCCAGCCCCAGCTC

CCTGTCCTCCCCAACACCTAGTGAGAAAGACGGTGCGTGGAAGGGAGTCCCATGGGCAGATGCTTACACG

ACCTCTTTGTGAAGCCTCTTCTGGGTTTAACTTCATTCATCAATTTATTCTTATGTCAAAGCAATGAAAC

TTTTCTTTCTGGAGCCAGATACCAATACAACAGGTGAACGGGTTTCTGCCACATCTCTACATTGACGGGG

GATGCTTGAACAACCCCCCTCACTACACAGACACACACCGTTAAGGCACAAGGGCTGGGGTTGAGCTCTA

GATGAGGGACTTTCCTGCTCCTGCAAGGGTGAGCACTGTATACACAGACAAGGAGGGTGCAGTAGAGTGA

CTCCCTTGGATGGAAGTAGTACCATCAGAACCTACTATTATTATGACATAAATTCTATTTACATACATTG

AGAGAATACTACAATCAACACTTTTTCCTGGGATGACTTTAAGAGGTTTGAGCCACAGCACCTGAAGTGG

CAAAGATCCATGGTCTTTGTAGGGTATTAGAGAACTCTTCCAGTCACCTCTGAAAGCACTCTAGATCTTG

CAGCTGAGTGGATGAAGTGTAACAAATCTGTTGCACGCTGAGAGGAGTCAGAATTAGCATTTTTCATGAA

AGTTCCCCACGTCTCTACTAAGAATGAGGAAGAAAAGACTAAGACTAGGTAATTACACAGAGGCTTGAAA

TGTTACATCACCAGAGCCAAGTCCTCTCCCTTCAGATCAGTTACTGGCTGCTACACAGGGACACCCCCAC

CTTTTCAGGGCATCCCATGCACTCCACTTCTCAGGATCTAAGGAATTTGACTTTGTAGGGATCCCAGAAA

GGGCACTGTGCCACTTCCCCTGGTGTGAATCAGACATACATTGTACATTCATTTCTAAAATTCACTCATG
```

-continued

```
CACCTCAAACCAAGGTCATTATCCAAAAAAAAAAAAAAAAAGCTCTGGGTGGAAGAGTTTGTAAGTTTTA

AGAGAGGGTCATTTCTATGTGAGGAAATGCAGAAATGGACAGAATGATTCTTATTCACTGTTTGGGTCTG

GAGAATTCCCATTGTGGAAATCTTAGAGATCTCAAGTTTATTACCAAGGGAATAAGGAAAAAAAGGTGAG

CAGGCACCAGGCCAAGCAGTGGCTCCCTTGCCAAGGAACCTGAGGCTGCAGGTTTCAGGGACCCCCTTGA

AGAAACCTCTCCTGGCCATTGGCCAGGAGAAAAGAGAAGTCTCTCCTGTAGAGTCACAAGAGAAGCAAAA

GAGGGTGGGTCACTGGGTCCTGGACATAGCCCCCAACCCCAAGACTTCCCAATATGGAGAAACTACACCA

ATGTTTAAAAGGGGAAAAGGAAAGAACTTGTACATCAAGGGAAGATGATTTGTAAACACACAGTCCTGTG

CAGAAAGATCCCCTTCAGGAGGTGTCTCCAGCATCCCAAAGCTGTGCGCACCTTCTCTTTTCCTGCCTCA

GGCCACCTATGCATCCAGCTGCAGCCCATACCCACACCTGAAATCCATCTCTTGAATCCCAGCCAGGTTA

TATACCACCCCATTGCCATGTCCTGTCCTGGCCAGAATGCATGCTGTTCCCCCAAGCCTCGTGGGAGTGA

GGCCATGGGAAACAGAGATGAGCATGTCTGGACAAGTCTGTGATGGTAGTGGATGAGAATAACCCATGGC

AAAACACGCACATTCATTAAGAAATAGGGCGACAGATTCCCCGTTGGTGAAGCACTGAAAGGTCTATTAC

TCTCATAATATTGCTGTTTTATTTTAATCCACCAGAGCTACCATGCAAAACTTTCCTCCTGTGAAACGCT

CCAGATAAAGCTCCTCTAATCTCCCCTTCCCTCATGTCCTCCAGCTCAAACCCACCTTCATCCCCCAAAC

CAATCTGTATCATGCCTGTTATCAGAGAGGCACAGAAAGATGGGCAGTGCCTCCGTTGTCACCATTCCCC

ACACCCCTACACACCCCCACACCCTCCCCTCCAGGCTCCACGACTTCACAGTCTTACTGTTGTAAATATC

ATTGTACAGTTTGTAATCCTCAAATAATCCCATTGTCAGAGGCCTCGCCTGATGGGCCTTCTCACCCTCG

AGAAAGGCCAGGGAATCTAGAAGGGGCAACCCTTCAAGGAGAGCTTCAGGGTCATCTCTGTGTGAGACAC

TATTGTATATTCCTGTAAGATTGCATTTTTATCTAAGGAATGATGTTATTTAAAAAACAAACAAAAAACA

CAAAAAATAAGAATTGCAAATAAATTTCTTAACAATGTCT
```

>NM_014316.3 *Homo sapiens* calcium regulated heat stable protein 1
(CARHSP1), transcript variant 1, mRNA (SEQ ID NO: 9)

```
GCTCTCAGTCGGAGCGAAGCGGCTGGCGGAGCAGAACGGATTGCAGGGTCAGCCATGTCATCTGAGCCTC

CCCCACCACCACAGCCCCCCACCCATCAAGCTTCAGTCGGGCTGCTGGACACCCCTCGGAGCCGTGAGCG

CTCACCATCCCCTCTGCGGGGCAACGTGGTCCCAAGCCCACTGCCCACTCGCCGGACGAGGACCTTCTCG

GCGACGGTGCGGGCTTCACAGGGCCCCGTCTACAAAGGAGTCTGCAAATGCTTCTGCCGGTCCAAGGGCC

ATGGCTTCATTACCCCAGCTGATGGCGGCCCCGACATCTTCCTGCACATCTCTGATGTGGAAGGGGAGTA

TGTCCCAGTGGAAGGCGACGAGGTCACCTATAAAATGTGCTCCATCCCACCCAAGAATGAGAAGCTGCAG

GCCGTGGAGGTCGTCATCACTCACCTGGCACCAGGCACCAAGCATGAGACCTGGTCTGGACATGTCATCA

GCTCCTAGGAGATGGTGGAAGCACCCCTTGTCCTGTGCTTGTGGGAGACTTTGCAGGGAGGAGGCAGCAG

ACACTGGAGATGACATTCTTCCACACGAGACGGGGCTTCAGCCGGGCATGGTCCCTCTCAAGTATCTCCT

GGAGGAAGGGGTATGGGGGGCAGGTGTGGGGTGTGGGGTGTTCCCGGCCATCAGCACAGCCTATGACCAT

TGCAACAACCTCTCACCATCTGAAGAGCATTAAAAGCATTTAAAAAGGAGAGGTGCCCACTGGTGGCTGA

GTGGAGGTTCCAACCCCATCCCAGGGAGTGGATCAAGGGTGGTATTTCTCCAGCTGCTCAGACACATGGG

CTCAACCCACAGAATCCCTCTTCCTCCTGGAGCTGGAGGCCCCAGATTCCCAGATCTGGCCCCCTGGCAG

CCTGACAGGGACCTTGCGTGACTTCTCCAAGGCAAATTTCCACCTAAGTGCCCCTTGCGCCTCTCCTGGG

GCCTGGGCAAAGCAGTTTTCTAATTCTTGGCTTGGTTGGTTCTAGGGGAGCTGGCTTGAAGTGGGTGGGG

AAAGGCGGGGGTGGCGGTCTTTGGATTGGACGGATGTTGCCTTTTGGTGCCTTTGCAGTGGGAGGCGGCA

TAGCTGCCTGTCTGGGGAAGACAGTTCTCCCAGCACTCCCACCCCTGGGCACAGCAGGCTGGTACTGGGA

GGCTGAACCCCTCTTAGAGCCTGACCTTTTCATCTGCCTTCTGGTTGTGTGACCATCACTCAACAGCCAT

TTCACAGCCCCTGTAATTATGGCGGCGGGGGGCTGGGGTGGTGGTGGTGGGAAGGGCTTGTGGAGAGGAC
```

-continued

```
ACAGTCTTTGTTTAAAAACTTTGTCCCGATCCATCCAGAAAAGAGTAGGTAGCTTGCATCCTGACAGCCT

GGCAAAGTCAAGAAAGTTGAAGGAGAAACATACCTTTGGAGAGGGGGTTTTCTTTAAAACTAGTGTTAAG

AAATGCTTAGGGATTTTTTTTTTCTTATTTTTCATAACTAAAGCTTTCACCCAGAGCCGGCTCTGTTTGC

ACTTTGCTGCCGACATTGCAAACTTTTTGGCAGGGTGGGAGACTGAGTCTCATTCTGTCACCCAGGCTGG

AGTGCAGTGGCCCGATCTCAGCTTACTGCAACCTCTGCCCTCCAGGGTTCTGGCAATTCCGCCTCAGTCT

CCTGAGTAGCTGGGATTACAGGCATGCGCCACCACACCCGGTTAATTTTTGTATTTTTAGTAGAGACCAG

GTTTCATCATGTTGGGCAGGATGGTCTTGAACCCCTGACCTCAGATGATCTGCCCATCTCGGCCTCTCAA

AGTGCTGGGATTACAAGTGTGAGCCATCGCGCCCGGCCTGCAAACTTTTTTGTAGGTATTTCTGGTAAAC

AAATCCTTAGGTTATCTTTGCTGTGGTTGTGGTTTGGCTTTAGTCATGATTTCAAAGTAGAAATAGCTAG

GCATTATTTTTTGAAATATATGACCTATATGTAGTCAAGAATCCACTGAACAGAGGCAAGCAAACCTTTT

GGAAACTGGCTTTTGGGCAGACAGTAAACGTCCAGTTTGATGCTGGAAGCATGAACAGCTTCATCAGGTA

GGTACTCCTCAACTCTGATGAGTTTGTCCTTTCAGCCTAAGGGGGTGGAAGGGAGTTGTTTGAGAATAGC

AAATACGCATGTTGATTGCGAGTGTGTGGAGACAAAGGCAGTTCCCACCACAGTTAGGTCCTGGCCATTG

TTTCCTCGCCTGCGATGCTCCTTGTACATCCTCACCCTCCTCTCCCGCCTCTGCCTTCTGCTGGGTCAAA

GGTGGCCTTTTCTCTCCAGCCTTGAATTGTTCCCTGTTGGCTTCCCAAGGGCCCATCTGCTGGTACAGTC

CACACTTCCACAGCCAAGACCCGAGAGGGCTTTCACTGCCCCAAGCCTCTCTCCTGTGACCCTGGGATTC

TGTCTTGGCAGAATCCTTTGTCAGCGGCTCTTACTCTGTCCTTCCTGTTTGGCCACAGCTCTTTCAATCA

ATGGGTATTCTAGAACCGCAGGATGTCAGAGCTGGAAGGGACGCGATACCGGTTTACACAAGGGGAAACT

CCTCGAGGCTCTGGGAGGGACGGAGGGTTTTGGTGACAGAGCGAGAGCTAAAATTGAGGATTCCTGAATC

CAGATCTTGCCTCCCATCAGCCATCTTTCTCCCAATAAATTTTTGTTTTGTGCAAGGCTAAAAAAAAAAA

AAAAAAA
```

>NM_006037.3 *Homo sapiens* histone deacetylase 4 (HDAC4), mRNA (SEQ ID NO: 10)

```
GGAGGTTGTGGGGCCGCCGCCGCGGAGCACCGTCCCCGCCGCCGCCCGAGCCCGAGCCCGAGCCCGCGCA

CCCGCCCGCGCCGCCGCCGCCGCCGCCCGAACAGCCTCCCAGCCTGGGCCCCCGGCGGCGCCGTGGCCGC

GTCCCGGCTGTCGCCGCCCGAGCCCGAGCCCGCGCGCCGGCGGGTGGCGGCGCAGGCTGAGGAGATGCGG

CGCGGAGCGCCGGAGCAGGGCTAGAGCCGGCCGCCGCCGCCCGCCGCGGTAAGCGCAGCCCCGGCCCGGC

GCCCGCGGGCCATTGTCCGCCGCCCGCCCCGCGCCCCGCGCAGCCTGCAGGCCTTGGAGCCCGCGGCAGG

TGGACGCCGCCGGTCCACACCCGCCCCGCGCGCGGCCGTGGGAGGCGGGGGCCAGCGCTGGCCGCGCGCC

GTGGGACCCGCCGGTCCCCAGGGCCGCCCGGCCCCTTCTGGACCTTTCCACCCGCGCCGCGAGGCGGCTT

CGCCCGCCGGGGCGGGGGCGCGGGGGTGGGCACGGCAGGCAGCGGCGCCGTCTCCCGGTGCGGGGCCCGC

GCCCCCCGAGCAGGTTCATCTGCAGAAGCCAGCGGACGCCTCTGTTCAACTTGTGGGTTACCTGGCTCAT

GAGACCTTGCCGGCGAGGCTCGGCGCTTGAACGTCTGTGACCCAGCCCTCACCGTCCCGGTACTTGTATG

TGTTGGTGGGAGTTTGGAGCTCGTTGGAGCTATCGTTTCCGTGGAAATTTTGAGCCATTTCGAATCACTT

AAAGGAGTGGACATTGCTAGCAATGAGCTCCCAAAGCCATCCAGATGGACTTTCTGGCCGAGACCAGCCA

GTGGAGCTGCTGAATCCTGCCCGCGTGAACCACATGCCCAGCACGGTGGATGTGGCCACGGCGCTGCCTC

TGCAAGTGGCCCCCTCGGCAGTGCCCATGGACCTGCGCCTGGACCACCAGTTCTCACTGCCTGTGGCAGA

GCCGGCCCTGCGGGAGCAGCAGCTGCAGCAGGAGCTCCTGGCGCTCAAGCAGAAGCAGCAGATCCAGAGG

CAGATCCTCATCGCTGAGTTCCAGAGGCAGCACGAGCAGCTCTCCCGGCAGCACGAGGCGCAGCTCCACG

AGCACATCAAGCAACAACAGGAGATGCTGGCCATGAAGCACCAGCAGGAGCTGCTGGAACACCAGCGGAA

GCTGGAGAGGCACCGCCAGGAGCAGGAGCTGGAGAAGCAGCACCGGGAGCAGAAGCTGCAGCAGCTCAAG

AACAAGGAGAAGGGCAAAGAGAGTGCCGTGGCCAGCACAGAAGTGAAGATGAAGTTACAAGAATTTGTCC
```

-continued

```
TCAATAAAAAGAAGGCGCTGGCCCACCGGAATCTGAACCACTGCATTTCCAGCGACCCTCGCTACTGGTA

CGGGAAAACGCAGCACAGTTCCCTTGACCAGAGTTCTCCACCCCAGAGCGGAGTGTCGACCTCCTATAAC

CACCCGGTCCTGGGAATGTACGACGCCAAAGATGACTTCCCTCTTAGGAAAACAGCTTCTGAACCGAATC

TGAAATTACGGTCCAGGCTAAAGCAGAAAGTGGCCGAAAGACGGAGCAGCCCCCTGTTACGCAGGAAAGA

CGGGCCAGTGGTCACTGCTCTAAAAAAGCGTCCGTTGGATGTCACAGACTCCGCGTGCAGCAGCGCCCCA

GGCTCCGGACCCAGCTCACCCAACAACAGCTCCGGGAGCGTCAGCGCGGAGAACGGTATCGCGCCCGCCG

TCCCCAGCATCCCGGCGGAGACGAGTTTGGCGCACAGACTTGTGGCACGAGAAGGCTCGGCCGCTCCACT

TCCCCTCTACACATCGCCATCCTTGCCCAACATCACGCTGGGCCTGCCTGCCACCGGCCCCTCTGCGGGC

ACGGCGGGCCAGCAGGACGCCGAGAGACTCACCCTTCCCGCCCTCCAGCAGAGGCTCTCCCTTTTCCCCG

GCACCCACCTCACTCCCTACCTGAGCACCTCGCCCCTTGGAGCGGGACGGAGGGGCAGCGCACAGCCCTCT

TCTGCAGCACATGGTCTTACTGGAGCAGCCGCCGGCACAAGCACCCCTCGTCACAGGCCTGGGAGCACTG

CCCCTCCACGCACAGTCCTTGGTTGGTGCAGACCGGGTGTCCCCCTCCATCCACAAGCTGCGGCAGCACC

GCCCACTGGGGCGGACCCAGTCGGCCCCGCTGCCCCAGAACGCCCAGGCTCTGCAGCACCTGGTCATCCA

GCAGCAGCATCAGCAGTTTCTGGAGAAACACAAGCAGCAGTTCCAGCAGCAGCAACTGCAGATGAACAAG

ATCATCCCCAAGCCAAGCGAGCCAGCCCGGCAGCCGGAGAGCCACCCGGAGGAGACGGAGGAGGAGCTCC

GTGAGCACCAGGCTCTGCTGGACGAGCCCTACCTGGACCGGCTGCCGGGGCAGAAGGAGGCGCACGCACA

GGCCGGCGTGCAGGTGAAGCAGGAGCCCATTGAGAGCGATGAGGAAGAGGCAGAGCCCCCACGGGAGGTG

GAGCCGGGCCAGCGCCAGCCCAGTGAGCAGGAGCTGCTCTTCAGACAGCAAGCCCTCCTGCTGGAGCAGC

AGCGGATCCACCAGCTGAGGAACTACCAGGCGTCCATGGAGGCCGCCGGCATCCCCGTGTCCTTCGGCGG

CCACAGGCCTCTGTCCCGGGCGCAGTCCTCACCCGCGTCTGCCACCTTCCCCGTGTCTGTGCAGGAGCCC

CCCACCAAGCCGAGGTTCACGACAGGCCTCGTGTATGACACGCTGATGCTGAAGCACCAGTGCACCTGCG

GGAGTAGCAGCAGCCACCCCGAGCACGCCGGGAGGATCCAGAGCATCTGGTCCCGCCTGCAGGAGACGGG

CCTCCGGGGCAAATGCGAGTGCATCCGCGGACGCAAGGCCACCCTGGAGGAGCTACAGACGGTGCACTCG

GAAGCCCACACCCTCCTGTATGGCACGAACCCCCTCAACCGGCAGAAACTGGACAGTAAGAAACTTCTAG

GCTCGCTCGCCTCCGTGTTCGTCCGGCTCCCTTGCGGTGGTGTTGGGGTGGACAGTGACACCATATGGAA

CGAGGTGCACTCGGCGGGGGCAGCCCGCCTGGCTGTGGGCTGCGTGGTAGAGCTGGTCTTCAAGGTGGCC

ACAGGGGAGCTGAAGAATGGCTTTGCTGTGGTCCGCCCCCCTGGACACCATGCGGAGGAGAGCACGCCCA

TGGGCTTTTGCTACTTCAACTCCGTGGCCGTGGCAGCCAAGCTTCTGCAGCAGAGGTTGAGCGTGAGCAA

GATCCTCATCGTGGACTGGGACGTGCACCATGGAAACGGGACCCAGCAGGCTTTCTACAGCGACCCCAGC

GTCCTGTACATGTCCCTCCACCGCTACGACGATGGGAACTTCTTCCCAGGCAGCGGGGCTCCTGATGAGG

TGGGCACAGGGCCCGGCGTGGGTTTCAACGTCAACATGGCTTTCACCGGCGGCCTGGACCCCCCCATGGG

AGACGCTGAGTACTTGGCGGCCTTCAGAACGGTGGTCATGCCGATCGCCAGCGAGTTTGCCCCGGATGTG

GTGCTGGTGTCATCAGGCTTCGATGCCGTGGAGGGCCACCCCACCCCTCTTGGGGGCTACAACCTCTCCG

CCAGATGCTTCGGGTACCTGACGAAGCAGCTGATGGGCCTGGCTGGCGGCCGGATTGTCCTGGCCCTCGA

GGGAGGCCACGACCTGACCGCCATTTGCGACGCCTCGGAAGCATGTGTTTCTGCCTTGCTGGGAAACGAG

CTTGATCCTCTCCCAGAAAAGGTTTTACAGCAAAGACCCAATGCAAACGCTGTCCGTTCCATGGAGAAAG

TCATGGAGATCCACAGCAAGTACTGGCGCTGCCTGCAGCGCACAACCTCCACAGCGGGGCGTTCTCTGAT

CGAGGCTCAGACTTGCGAGAACGAAGAAGCCGAGACGGTCACCGCCATGGCCTCGCTGTCCGTGGGCGTG

AAGCCCGCCGAAAAGAGACCAGATGAGGAGCCCATGGAAGAGGAGCCGCCCCTGTAGCACTCCCTCGAAG

CTGCTGTTCTCTTGTCTGTCTGTCTCTGTCTTGAAGCTCAGCCAAGAAACTTTCCCGTGTCACGCCTGCG
```

-continued

```
TCCCACCGTGGGGCTCTCTTGGAGCACCCAGGGACACCCAGCGTGCAACAGCCACGGGAAGCCTTTCTGC

CGCCCAGGCCCACAGGTCTCGAGACGCACATGCACGCCTGGGCGTGGCAGCCTCACAGGGAACACGGGAC

AGACGCCGGCGACGCGCAGACACACGGACACGCGGAAGCCAAGCACACTCTGGCGGGTCCCGCAAGGGAC

GCCGTGGAAGAAAGGAGCCTGTGGCAACAGGCGGCCGAGCTGCCGAATTCAGTTGACACGAGGCACAGAA

AACAAATATCAAAGATCTAATAATACAAAACAAACTTGATTAAAACTGGTGCTTAAAGTTTATTACCCAC

AACTCCACAGTCTCTGTGTAAACCACTCGACTCATCTTGTAGCTTATTTTTTTTTAAAGAGGACGTTTTC

TACGGCTGTGGCCCGCCTCTGTGAACCATAGCGGTGTGCGGCGGGGGGTCTGCACCCGGGTGGGGGACAG

AGGGACCTTTAAAGAAAACAAAACTGGACAGAAACAGGAATGTGAGCTGGGGGAGCTGGCTTGAGTTTCT

CAAAAGCCATCGGAAGATGCGAGTTTGTGCCTTTTTTTTTATTGCTCTGGTGGATTTTTGTGGCTGGGTT

TTCTGAAGTCTGAGGAACAATGCCTTAAGAAAAAACAAACAGCAGGAATCGGTGGGACAGTTTCCTGTGG

CCAGCCGAGCCTGGCAGTGCTGGCACCGCGAGCTGGCCTGACGCCTCAAGCACGGGCACCAGCCGTCATC

TCCGGGGCCAGGGGCTGCAGCCCGGCGGTCCCTGTTTTGCTTTATTGCTGTTTAAGAAAAATGGAGGTAG

TTCCAAAAAAGTGGCAAATCCCGTTGGAGGTTTTGAAGTCCAACAAATTTTAAACGAATCCAAAGTGTTC

TCACACGTCACATACGATTGAGCATCTCCATCTGGTCGTGAAGCATGTGGTAGGCACACTTGCAGTGTTA

CGATCGGAATGCTTTTTATTAAAAGCAAGTAGCATGAAGTATTGCTTAAATTTTAGGTATAAATAAATAT

ATATATGTATAATATATATTCCAATGTATTCCAAGCTAAGAAACTTACTTGATTCTTATGAAATCTTGAT

AAAATATTTATAATGCATTTATAGAAAAAGTATATATATATATATAAAATGAATGCAGATTGCGAAGGTC

CCTGCAAATGGATGGCTTGTGAATTTGCTCTCAAGGTGCTTATGGAAAGGGATCCTGATTGATTGAAATT

CATGTTTTCTCAAGCTCCAGATTGGCTAGATTTCAGATCGCCAACACATTCGCCACTGGGCAACTACCCT

ACAAGTTTGTACTTTCATTTTAATTATTTTCTAACAGAACCGCTCCCGTCTCCAAGCCTTCATGCACATA

TGTACCTAATGAGTTTTTATAGCAAAGAATATAAATTTGCTGTTGATTTTTGTATGAATTTTTTCACAAA

AAGATCCTGAATAAGCATTGTTTTATGAATTTTACATTTTTCCTCACCATTTAGCAATTTTCTGAATGGT

AATAATGTCTAAATCTTTTTCCTTTCTGAATTCTTGCTTGTACATTTTTTTTTACCTTTCAAAGGTTTTT

AATTATTTTTGTTTTTATTTTTGTACGATGAGTTTTCTGCAGCGTACAGAATTGTTGCTGTCAGATTCTA

TTTTCAGAAAGTGAGAGGAGGGACCGTAGGTCTTTTCGGAGTGACACCAACGATTGTGTCTTTCCTGGTC

TGTCCTAGGAGCTGTATAAAGAAGCCCAGGGGCTCTTTTTAACTTTCAACACTAGTAGTATTACGAGGGG

TGGTGTGTTTTTCCCCTCCGTGGCAAGGGCAGGGAGGGTTGCTTAGGATGCCCGGCCACCCTGGGAGGCT

TGCCAGATGCCGGGGGCAGTCAGCATTAATGAAACTCATGTTTAAACTTCTCTGACCACATCGTCAGGAT

AGAATTCTAACTTGAGTTTTCCAAAGACCTTTTGAGCATGTCAGCAATGCATGGGGCACACGTGGGGCTC

TTTACCCACTTGGGTTTTTCCACTGCAGCCACGTGGCCAGCCCTGGATTTTGGAGCCTGTGGCTGCAAGG

AACCCAGGGACCCTTGTTGCCTGGTGAACCTGCAGGGAGGGTATGATTGCCTGACCAGGACAGCCAGTCT

TTACTCTTTTTCTCTTCAACAGTAACTGACAGTCACGTTTTACTGGTAACTTATTTTCCAGCACATGAAG

CCACCAGTTTCATTCCAAAGTGTATATTGGGTTCAGACTTGGGGGCAGAAGTTCAGACACACCGTGCTCA

GGAGGGACCCAGAGCCGAGTTTCGGAGTTTGGTAAAGTTTACAGGGTAGCTTCTGAAATTAACTCAAACT

TTTGACCAAATGAGTGCAGATTCTTGGATTCACTTGGTCACTGGGCTGCTGATGGTCAGCTCTGAGACAG

TGGTTTGAGAGCAGGCAGAACGGTCTTGGGACTTGTTTGACTTTCCCCTCCCTGGTGGCCACTCTTTGCT

CTGAAGCCCAGATTGGCAAGAGGAGCTGGTCCATTCCCCATTCATGGCACAGAGCAGTGGCAGGGCCCAG

CTAGCAGGCTCTTCTGGCCTCCTTGGCCTCATTCTCTGCATAGCCCTCTGGGGATCCTGCCACCTGCCCT

CTTACCCCGCCGTGGCTTATGGGGAGGAATGCATCATCTCACTTTTTTTTTTTAAGCAGATGATGGGATA

ACATGGACTGCTCAGTGGCCAGGTTATCAGTGGGGGGACTTAATTCTAATCTCATTCAAATGGAGACGCC

CTCTGCAAAGGCCTGGCAGGGGGAGGCACGTTTCATCTGTCAGCTCACTCCAGCTTCACAAATGTGCTGA
```

-continued

GAGCATTACTGTGTAGCCTTTTCTTTGAAGACACACTCGGCTCTTCTCCACAGCAAGCGTCCAGGGCAGA

TGGCAGAGGATCTGCCTCGGCGTCTGCAGGCGGGACCACGTCAGGGAGGGTTCCTTCATGTGTTCTCCCT

GTGGGTCCTTGGACCTTTAGCCTTTTTCTTCCTTTGCAAAGGCCTTGGGGGCACTGGCTGGGAGTCAGCA

AGCGAGCACTTTATATCCCTTTGAGGGAAACCCTGATGACGCCACTGGGCCTCTTGGCGTCTGCCCTGCC

CTCGCGGCTTCCCGCCGTGCCGCAGCGTGCCCACGTGCCCACGCCCCACCAGCAGGCGGCTGTCCCGGAG

GCCGTGGCCCGCTGGGACTGGCCGCCCCTCCCCAGCGTCCCAGGGCTCTGGTTCTGGAGGGCCACTTTGT

CAAGGTGTTTCAGTTTTTCTTTACTTCTTTTGAAAATCTGTTTGCAAGGGGAAGGACCATTTCGTAATGG

TCTGACACAAAAGCAAGTTTGATTTTTGCAGCACTAGCAATGGACTTTGTTGTTTTTCTTTTTGATCAGA

ACATTCCTTCTTTACTGGTCACAGCCACGTGCTCATTCCATTCTTCTTTTTGTAGACTTTGGGCCCACGT

GTTTTATGGGCATTGATACATATATAAATATATAGATATAAATATATATGAATATATTTTTTTAAGTTTC

CTACACCTGGAGGTTGCATGGACTGTACGACCGGCATGACTTTATATTGTATACAGATTTTGCACGCCAA

ACTCGGCAGCTTTGGGGAAGAAGAAAAATGCCTTTCTGTTCCCCTCTCATGACATTTGCAGATACAAAAG

ATGGAAATTTTTCTGTAAAACAAAACCTTGAAGGAGAGGAGGGCGGGGAAGTTTGCGTCTTATTGAACTT

ATTCTTAAGAAATTGTACTTTTTATTGTAAGAAAAATAAAAAGGACTACTTAAACATTTGTCATATTAAG

AAAAAAGTTTATCTAGCACTTGTGACATACCAATAATAGAGTTTATTGTATTTATGTGGAAACAGTGTT

TTAGGGAAACTACTCAGAATTCACAGTGAACTGCCTGTCTCTCGAGTTGATTTGGAGGAATTTTGTTT

TGTTTTGTTTTGTTTGTTTCCTTTTATCTCCTTCCACGGGCCAGGCGAGCGCCGCCCGCCCTCACTGGCC

TTGTGACGGTTTATTCTGATTGAGAACTGGGCGGACTCGAAAGAGTCCCCTTTTCCGCACAGCTGTGTTG

ACTTTTTAATTACTTTTAGGTGATGTATGGCTAAGATTTCACTTTAAGCAGTCGTGAACTGTGCGAGCAC

TGTGGTTTACAATTATACTTTGCATCGAAAGGAAACCATTTCTTCATTGTAACGAAGCTGAGCGTGTTCT

TAGCTCGGCCTCACTTTGTCTCTGGCATTGATTAAAAGTCTGCTATTGAAAGAAAAAGAAAGCGAACAGT

TTTTGTTTGTTTTTTTTGCCGTGTGTGCTCCATAGTGGAGGCGCTATTTTCCAATTGATGAGAATGACAA

ACATATATAATCTATCTATCTATCTATCTATCTATCTATACAGGGGGCTTGAACCTTACTCACCCA

AGAGCTTCTTACGGAATGTGGTAGAAAACCAAGTTGTAACGACACTGTAACCTACCTGATGCCTGTTCGC

GCCCGCCGTGAGCTGCGCACTGGCCGTGGCCACCATTCACCTCTGTAATTTAATCCGTTTCTCTTGGATT

GTCTGGACGTGCCCGATGGTTCTTTCTTTTGCTCAGTGGAGTTGGAGGTTTTGTGTTTGGTTTTCTCATT

CTTGTCTTGTTTTGTGTGGGTGGATTTTCACCGACCAATGATATCCTCTTCTGACGGTCACCTTCTTTCC

ACTTCACTGGAGTCCAGTATTCTGTACCACATCACGCAACGTGTTATCTTGTGGTGTAAATAAAGACTGC

GTTACTTGCCCTCCCAAAAA

>NM_001200049.2 *Homo sapiens* cilia and flagella associated protein 46
(CFAP46), mRNA (SEQ ID NO: 11)

CAACCGTGGCCGGGTCCTCGCGGCTGGAGAACCCAACCGACAGTGGGCGGCAGGACGCACCGCGGACCCC

GGAGAGAGCGGACGAGCAGGGCGCCGGCGCCATGGACCTGGTCATCACGCAGGAGCTGGCCCGCGCCGAG

AGCCAGCAAGATGCTGCGTCCTTGAAGAAGGCCTACGAGTTGATCAAATCGGCCAACCTAGGGAAATCGG

AGTTTGACCCCTCAGAGAGCTTCAGCCCAGACCTGTTTGTTCTGTGTGCAGAGCAGGCCCTGAAGATGAG

GCAGCCAGAGGTGAGCGAGGACTGCATCCAAATGTACTTCAAGGTGAAGGCGCCCATCACCCAGTTTCTG

GGCCGAGCGCACCTGTGCAGGGCCCAGATGTGTGCCCCGAAGTCGGCAGAAAACCTGGAGGAATTTGAAA

ATTGCGTGACTGAGTACATGAAGGCCATAAACTTTGCCAAAGGAGAACCGAGGTACTACTTTTTGGTGTA

CAATGCATCAGTCCTCTACTGGCAGATGGTGAGGCCGTTCCTCAAGCCTGGATATCGTCACCATCTGATC

CCCAGCCTTTCCCAAATCATAAACGTGCTGAGTCAGACTGAGGAGGAAGACAAGGAGTGGCGTGCTGAGC

TGATGCTGGAACTTCTGGAGTGTTATCTGCAAGCCGGAAGAAAGGAGGAGGCTGCCAGGTTCTGCTCCAC

-continued

GGCAGCTCCGTTCATTAAGTCTCACGTGCCACAGAAATACCGGCAGATATTCTCTGTTATGGTTCGTCAT

GAATTAATGGACGAACTTCAGTTAAAGGAAGAAAAGAAAAATTCCATTAGCCTGTCAGTCACTTTCTATA

TTAATATGCTAAAGGCAAAAGCGGAGCAAAATGATTTACCAGGTGACATCAGTGTCATTCTGAGGAAGGC

CTACAGACACTTAGGTCATTACAACCACCAGCGCTTTCCCTCTATCAGTGAAGAAAAATGCTTTTGCTT

TTTGAATTGGCGCGTTTTTCCTTGACCTTGAAATGCATGGAGATCTCCTCTGCCTGCCTCTCAGACCTGA

AGAAGATGGAAAGCAAAGATCCTGGGAAGCTTATTGAAATGGAATGTCTGGAGTGTGAATCGGAAGCTTT

AAGACTTGAAAGTAAGATGAAAGTGTACAACCGAGCGGCTGTTGAGGCCCAGCTGGATATCATACAGAGG

CTAGACGTCGCGCTGCAGCGAGCCGTGCGCCTGGGCGACCCCCGGGTCATCCACGTGGTGTGCGCCACGC

AGTGGAACACCTGCCTGCCCCTGCTGCAGCACAACCTGCGGCACCACCTGCGGAAGCCCCTGGCTGGCGT

TGCGGACGTGCTGGAGAAGCTGGACAGCCTCATGACGCTTCTCCGCTGTCAAGTGCACATGGAGATGGCG

CAGATCGAGGAGGACGAGGACCGGCTGGAGCCCGCCACGGAGCACCTCCGGAAAGCCGCGCGCCTGGACA

GCCTGGGCCTCTACCGGGACAGGATCCAGATGGCCTCCACCCGGCTGCGTCTGTGCACCACGCTATACCA

GGCCCCTGAGCGCGCAGAGGACAAGGCCATCATGGCCGTTGAGCAGGCAAAAAAAGCTACACCAAAGGAC

AGCGTCAGGAAGAAGCGGGCCCTCCTGGTGAATGCAGGCCTGGCCTTAGCCCCTGACGCGTTTCAGATTG

TGCTGGACAGTGAGAATGAGGCCAAAGTCTCCACCGGGAAGAACAGGGGCCGGTTCACCTACCTCTGTGC

GAAGGCGTGGCACCACACCGTCAGCGTGGACAAAGCTGCCGGGCACCTGCGGCGCCTGGGCAACGAAAAC

GACAAGGAGAGGATACAGATTTGGGCAGAGCTGGCCAAAGTGGCCCGGAAACAAGGCGTGTGGGACGTCT

GTCGGACGGCGAGCCGCTTCTGCCTCCTGTATGACAACGTCAAGGTGAAGAAGTTGAGGCTGCGGCGAGG

GAAGAAGAAGCGAGGTAGGGACGGCTCGGTGCAGGACACCTGGAGCCAGCCTGAGGTCGTCCTGCAGAGG

CAGGTGTGCCCCGACCTGCTGCGGAAGTTCGCGGAGGTGGGGTTCATCCATGCTGAGGCCACGGTTCATT

TGCTGCGGTCAGAAGGTGTAGAGCTGAATGACCGGGCCATCCCCCCCGAAGACCTGAGCCAGCACCCAGC

TGGCTACGTGCCTGAGCCCCCGGAGGTGAATGCTGAGTGGATCACATACAGAACCTGGATCGAGAGTCTG

TCCCGGTGTGCCATGAATAACTGGCTGCGCTCCGCAGAGATCGGACAGGAGATCCAGGAGGCGTGGATTG

TGCAGAACGCCGTGGTCTACGTCCTGAACCACAACCACCACCTGATCCTGGCCGGGCGGCAGAAGGAGCT

GGTGGACGCCCTGTACCACCTCCTGAGCATCGTTAAGGCCACAGGCCACAGTGGGGACCCCGTGATGCTG

GTGACGCTCTGCAACACCTTGGCGCGAGGCCTGATCATCAGCTGGATTCCAGTCCAGGCTGCCGAGAAGT

CCAGGAAATTCATGCGACCAAACGCGTTTCACAGCCCACTGGACGCAGGAGCCACTTCCGAGATCAAAAC

AGCGGTGGAGGTCTGCGAGTTTGCCCTGAACCTGACCAATGGGAGTGCGCCCGAGGAGACGGTGCCCACC

GGCACCCGGCAGCAGCTTATCGCCACCTGGGTCAAGGCCAAGCAGCTGCTGCAGCAGCAGATTGGGCCAC

GGCTGGGCACCGAGGAGCAGGGCACCAATGAGGATGTCAGCTCGGTGACCAGAGTCCTCGTTGCCTTGGA

AATGTACTCATGCAACGGGCTGGGCCTCATGGACTTCACTGTCCCCTCCCTGGCCCAGTTGGTGAAAATG

GCTTCCGAGTGCAACTGGTCGGACCCCCTGGTGGAGCTGCAGACCCTGACGCGGCTGACCCACTTCGCCC

ATGCAGCGCGTGACCATGAGACCACCATGGCCTGTGCTCACAGGGCTCTGGAGATGGGCATCAAGTACCT

GAAGAAATTTGGGCCCGAGGAGTCCCGGCTGGTGGCAGAGATGCTGTGCACAGCCACGGCCATCCAGGGC

AGGAGCATCATGGAAAACCTGAAGGGCCGGAAGCAGCTGCGACTGGTGGCAGCCAAGGCCTTCACGGAGA

GCGCCAGGTTCGGAGGCATCGCGGGCAGCAGCGCCCTGGTGATGCTGGCCGCGCGGCATTACTGGAACGC

CTGGCTCCCACTGCTGTCCTCAGCCGTCTACAGGAAGAAGGCCAAGGGTGCCCTGAAGAGGCTCATCGGC

ATCATCAACAAGACAGAGGCCAGAAAGCAGGAGAAAGGAAAGACGCTGCTTCTGCACCAGTGGCCCACGG

CCGACTTCCAGGGTGGCGGGACGACCGAAGGATATTTTCTTCCAGGGGCTGAGGACGACCTGGCGCTCCG

TGCTGCGCTCTACGGCCTGCTCTTCCACAGCCATGCCGACCAGGACGACTGGGAGGGCGGCCTCAAGGTG

-continued

```
CTGGACGAGGCTGTGCAGGTGCTGCCAAGGACGGCCCACCGCCTCTTGATCTTCAAGCACATGGTCATCG

TGAAGGCCAAGCTCGGGCAGAATTTTTCGATGGAAATACAGAAATTCAAGGCCGAGAGTGAGGACTACTT

GGCGCGCATGTGGCACCGCCTGGCCCTGAACTCGCCGAGCGTGTCTGGAGAGCTGGCCTGCTACAACAAC

GCCATCCAGGCCTTGCAGAAGCCTGAGATGGAGTGGCAGAAGGTGGAGTACCTCATGGAGTTCGGCCAGT

GGCTCCATCACAGACACTTTCCTCTCGAGGACGTGGTCTTCCACCTCCGCTGGGCTGTCGAGATCCTGCT

GGCCATGAAGCCGCCCGGCGATGTCCCTGAGCCACAGCCCACGCCGGATGGGGAGTACGTGGCTGTGGAG

ATGCCCCCACGGAGCCCCGTGTCCGAGGCCGAGGAGGCGGTGTCCTTGGAGCAGCTGCGTAGCGTGCGGC

AGCTGGAGGCGCTGGCCCGCGTGCACATCCTGCTGGCCCTGGTGCTGTCGCCGGGCGCCGAGGGCTACGA

GGACTGCTGCCTTGCAGCCTACGCCTTCTTCAGGCACATCTGGCAGGTTTCTTTGATGACAGCAGGAAAA

TCAGTTCTGGAAAACAGACCCCTGGCAGCAACCAGCTCACATCTGTTATTGCCTAAAAAAGAGAAGGAGA

ATGAGAGGAGTAAAGAGAAGGAGAAGGAGAGGAGTAAAGAGAAGGAGAATGAGAGGAGTAAAGAGAAGGA

CAAGGAGAAGGGAAAGGAGGAGAAAGTCAAGGAGCCCAAGCAGTCTCAAAGCCCAGCTCCTATCAAACAA

CTGGAAGACTTACCCATGAGCATAGAAGAGTGGGCTTCCTACTCCTGCCCCGAGGAAGTGCTGTCTGTAC

TGAAACAGGACAGAAGTGACTCTACTGTGAACCCCTCAAGTATCCAGAAGCCGACATACAGTTTGTATTT

CCTGGACCACCTGGTCAAGGCCCTGCAGAAGATGTGCCTGCACGAACTCACGGTTCCCGTCCTGCAGTTG

GGGGTGCTGATTTCGGACTCCGTGGTGGGAAGCAAGGGCCTGTCGGATCTCTACCACCTTCGCCTCGCCC

ACGCGTGCTCCGAGCTGAAGCTGAGAGAAGCAGCCGCGCGCCATGAAGAGGCGGTCGGGCAGGTGTGCGT

CAGCGAGCTGGAGCAGGCCAGCTGCAGAAAAGAGATCGCGTTGAAAAAAGAGAAAAATAAGGAGCCTTTA

TTAGAAGAAAGCCTGCCAGCACTGAATGAGCAGACACTTCCTGTCCAGCCTGGGGAGATCAAACCACTGG

ACGCCAAGGACAAGATTTTGAAGATGAATGGGGAGACCGGGAGGGACCTGGATGGGACGTCCTTTCCCCA

CCTGTGGATGCTGAAGGCAGAAGTTCTGCTGGAGATGAACCTGTACCAGCCTGCACGGCTGCTCCTGTCG

GAGGCTTACCTGGCTTTCCAGGAGCTGGATGAGCCTTGTGCAGAGGCCCAGTGCCTGCTCCTCCTCGCAC

AGTTGGCCAACAAGGAGAAAAACTATGGACAAGCCAAGAAAATGATCGCACAGGCCCAGCACCTGGGCGG

AAGTGAGGAGTTCTGGTACAATTCCACTCTGACCCTGGCAGAGGCGCTCTTGTCCATGGAACACTCAGGA

AGGGAAGCTACGGTGTGTCACATATTTCAGAAGCTCATCAATGCCTTCAAGATCCTCAAGAAAGAAAGAC

CAAACCGATTGCCTTTACTGGAATTCATGATCACAGATCTAGAAGCCAGGTGCCTGAGCCTGCGGGTCAG

AGTTGCGCAGCACTCAGCGGTCACTGAACCCACAGAGTGCTCGTTGCTACTGAAAGAGATGGATGATGGC

CTGTTGGAAATTGAGAGAAAGTTTATCGACTGTGGCTGCAAAGAGAATTGTGTTGACGTAAAACTAGAGC

GTGCGAAGATCAAGAGGTTAGGTGCCCAGAACGAGAAAGATGAAGAACAAAAAACTGCGTATTACTTGGA

AGCGTATGGCCTGGCCCAGGGTGCCGTAGCTGAGGAAGAAGGGAGGCTTCACAGCATCCAGGGCTTATAT

GGCCTGGCCCAGGGCGCCATGGCTGAGGAAGAAGGGAGGCTTCACAGCGTCCAGGGCCTATTGTCACTTC

AAGACTTGCAGAACGTCAACACGCCCCTGATGAGGAAGCTGGCGCGCCTCAAGCTCGGCCTCGTGGAAAT

GGCTCTGGACATGCTCCAGTTCATCTGGGAGGAGGCCCACGGGCAGCAGAGTGAGCAGGGGTCCCTGGAG

AAGCTGCTGGCGGACTATCTGCAGAACACCAGTGACTACACTTCCGTCGGCCTGCAATGGTTCACGCTGA

AGCGGACTCTAGCACACGGGGCACTGGCACAGCTGGGGAGCCTGCAGCCGCTGAGCGTGGGCTGTGTGGA

GATCCGCGCCCGGCTCCTGGGCCTGGCCGGGAGGGCCCTGCACCTGCTGGCCATGCAAGCTGACCCTGTG

CACCCTACCTGCTACTGGGAGGCGGGCCCCTCGGTGGGCGCCAAGCTGAGCGGCCTCAAGTCTCTGGAGC

TGGAGGTAGAGGAAGAGGGTGCCACAAAGTCCAGCAGGGACCCGCCGGCCTCCAGGGCAGCCCCGGAGGA

GCACTGCAGGAGAGGCGAGGACCTGAAGAGGAGGATGGTTCTGGCCCAGCAGTACCTGGCTCAGGCGTCA

GAGGTGCTGCTGCAGTGCCTACAGGTGGCCCTTGGCAGTGGCCTCCTGGATGTCGCAGCAGCCGCCAGCC

TGGAGATGGTGGAGTGTGTCGGCACCCTGGACCCTGCAACTACCTGCCAGTTCCTGGCTCTGTCTCAGAG
```

-continued

CTGCTCGGCCTCAGAGACGATGAGGGATGTCCTGCTTGCAGCCACAGCCAACACCAGCAGCTCACAGCTG

GCGGCCCTGCTGCAGCTACAGCACCAGCTCCGGTGCCAAGACAGGACCACCACCAGCCTGGGCGCCCGTG

TGGAGCAGAGGCTGGCCGCCGTGTCCAAGGCTTGGCAAAATCTCTGCGTCACTGAGCAGCATTTTAACCT

CTTGAATGAGATGCCTCCGACCTTTTGGATCCTCTTTCTGCACCTCTCAGGGGACAGGTCCCGTCTGTAC

GGCGCTGCCTACGAGAAACCCAAGTTCATTACTGCAGCCAAAGGAAAGGTGCAGGCGGTGGGAGGCTCCT

GCAAGGTGATGCGTCTGGCCATAAGTCCCACTGCCTTCTCCCACCTGCTGGCCTGTGCCCAGCAGTTCCG

GAAGCAGACCCAGGCCCAGGTGTACAGTGAGGACATGGCCCTGAACATAGGCTCGGAACCAGAAGGCCTG

CAGGTGGAAGAGAAGGAGCGCCCTGTGCAGAGGCTCAGTAGCGTCCTGGGGCCCCTGGAGGAGCTTCTGC

AGCCGCTATTCCCCCTGCTCAGCCTCTCCAAGGCCAGAGTGCAGACACCTGCGGTTGTTGCCGATTCAGG

GAAGTCGAAGGGCAAAGACAAGGAGAGGAAAACGTCCACAGGACAACACAGCACAGTCCAGCCTGAGGTT

GCCGATAAGATAGTCCTGGTCGCAGACAGACATCTCCTGGAGCTGCCACTGGAAGGTCTCTCTGTGTTCG

ATGAAGGGACAATTTCCTCTGTGTCACGAGAATTTTCTCTTCAAATGCTGTGGAATCGCCTCCATAAAGA

AGAGACAGAAGGTGGCGTGAAAAAGGAGGGAAGAAGCAGAGACCCCAAAAAGAGAAGCCTAGCGAAGAAG

GGCAGGAAGGGCAGCATCCCCCGGACCATCCCCCCTGACTGCATCATAGTCGACTCAGACAACTTCAAGT

TCGTCGTGGACCCATACGAGGAGGCCCAGGGCCCAGAAATGCTAACTCCTGTCTCCATCACCCAAGACAT

TTTGGAAAGATTCCAAGACACATTCACGTCGCGATGGGCGGGACATCTGGGAAGCAAGCACTTTCCCAGC

CAGGCCCAGTGGGAGCAGGCCCTGGGCAGCTGCAGCGGTTTCTTCTTCTATGGAATGGAGAGCTTCCTGT

CCCATATATTAGTGGAGAGATTGGTCGCCATGAACTTGCAAGAGTGCCAGGTGGCAGTCCTGCTGGACCT

GGCGCGGTCCTACCAGAGCTTGAAGAGGCACATGGAGAGCGTGGAGCACAGGAGATCTGTTGGCCGTTGG

GAAGCCAATTGGAGAAACAGTGCGTCTCCTTCAGAAGATGAGTGGCGACGAGGCGGTGAACCAAGACGAG

GCTTCTCAGACCTTGAAGGACAAGCTGCTGCTGCTCCAAAGCTCCGAGCTCCTTCCCACCACGCTCAACT

TGGTCCTGTATGGGCTGCCGCACCAAGCCATCGGGTAGTGCAGGCCTGGACCTGCCTCCCATCAGCTGCT

GGGGCCCCAGCACTTGCCTCTGCCCTTGGCTCTGCCCCTCTGCCAACCCATCCCCACCTCCCGGCTCCCA

TCCCCAGCTCCCAGCTCGCTCTCCCCTTCCTGGGCCTCTCCCCAGCCCTTGGTGCAGCCTCAGCCAGGGA

CCCTCCCCCAGCGACTTCCCGCAAGGCAGCCGCCTGGACCTCGAGCTCTGCCTGCCTGTGTGCGCCATGG

GGTCTGCGTCGGGGCTGGAGCTGCGTCTCTTCCCGGGGCCAGGACAAGGGCGGCCTCCCCTTGGCGGCGC

TGGTGCTGAGTTGCTTAGACCAGAAGACTATTCAGACCGTGAGCCTGTTTTTGATTTGAGTGTTCCACTA

AACAAACAACAAAAGCCAAAAAAAAAAAAAAAA

>NM_198433.2 *Homo sapiens* aurora kinase A (AURKA), transcript variant 1, mRNA (SEQ ID NO: 12)

CTTAAACGCGACTCAAGGCGTCGGGTTTGTTGTCAACCAATCACAAGGCAGCCTCGCTCGAGCGCAGGCC

AATCGGCTTTCTAGCTAGAGGGTTTAACTCCTATTTAAAAAGAAGAACCTTTGAATTCTAACGGCTGAGC

TCTTGGAAGACTTGGGTCCTTGGGTCGCAGGTGGGAGCCGACGGGTGGGTAGACCGTGGGGGATATCTCA

GTGGCGGACGAGGACGGCGGGGACAAGGGGCGGCTGGTCGGAGTGGCGGAGCGTCAAGTCCCCTGTCGGT

TCCTCCGTCCCTGAGTGTCCTTGGCGCTGCCTTGTGCCCGCCCAGCGCCTTTGCATCCGCTCCTGGGCAC

CGAGGCGCCCTGTAGGATACTGCTTGTTACTTATTACAGCTAGAGGGTCTCACTCCATTGCCCAGGCCAG

AGTGCGGGGATATTTGATAAGAAACTTCAGTGAAGGCCGGGCGCGGTGGCTCATGCCCGTAATCCCAGCA

TTTTCGGAGGCCGAGGCTGGAGTGCAATGGTGTGATCTCAGCTCACTGCAACCTCTGCTTCCTGGGTTTA

AGTGATTCTCCTGCCTCAGCCTCCCGAGTAGCTGGGATTACAGGCATCATGGACCGATCTAAAGAAAACT

GCATTTCAGGACCTGTTAAGGCTACAGCTCCAGTTGGAGGTCCAAAACGTGTTCTCGTGACTCAGCAATT

TCCTTGTCAGAATCCATTACCTGTAAATAGTGGCCAGGCTCAGCGGGTCTTGTGTCCTTCAAATTCTTCC

CAGCGCATTCCTTTGCAAGCACAAAAGCTTGTCTCCAGTCACAAGCCGGTTCAGAATCAGAAGCAGAAGC

AATTGCAGGCAACCAGTGTACCTCATCCTGTCTCCAGGCCACTGAATAACACCCAAAAGAGCAAGCAGCC

CCTGCCATCGGCACCTGAAAATAATCCTGAGGAGGAACTGGCATCAAAACAGAAAAATGAAGAATCAAAA

AAGAGGCAGTGGGCTTTGGAAGACTTTGAAATTGGTCGCCCTCTGGGTAAAGGAAAGTTTGGTAATGTTT

ATTTGGCAAGAGAAAAGCAAAGCAAGTTTATTCTGGCTCTTAAAGTGTTATTTAAAGCTCAGCTGGAGAA

AGCCGGAGTGGAGCATCAGCTCAGAAGAGAAGTAGAAATACAGTCCCACCTTCGGCATCCTAATATTCTT

AGACTGTATGGTTATTTCCATGATGCTACCAGAGTCTACCTAATTCTGGAATATGCACCACTTGGAACAG

TTTATAGAGAACTTCAGAAACTTTCAAAGTTTGATGAGCAGAGAACTGCTACTTATATAACAGAATTGGC

AAATGCCCTGTCTTACTGTCATTCGAAGAGAGTTATTCATAGAGACATTAAGCCAGAGAACTTACTTCTT

GGATCAGCTGGAGAGCTTAAAATTGCAGATTTTGGGTGGTCAGTACATGCTCCATCTTCCAGGAGGACCA

CTCTCTGTGGCACCCTGGACTACCTGCCCCCTGAAATGATTGAAGGTCGGATGCATGATGAGAAGGTGGA

TCTCTGGAGCCTTGGAGTTCTTTGCTATGAATTTTTAGTTGGGAAGCCTCCTTTTGAGGCAAACACATAC

CAAGAGACCTACAAAAGAATATCACGGGTTGAATTCACATTCCCTGACTTTGTAACAGAGGGAGCCAGGG

ACCTCATTTCAAGACTGTTGAAGCATAATCCCAGCCAGAGGCCAATGCTCAGAGAAGTACTTGAACACCC

CTGGATCACAGCAAATTCATCAAAACCATCAAATTGCCAAAACAAAGAATCAGCTAGCAAACAGTCTTAG

GAATCGTGCAGGGGGAGAAATCCTTGAGCCAGGGCTGCCATATAACCTGACAGGAACATGCTACTGAAGT

TTATTTTACCATTGACTGCTGCCCTCAATCTAGAACGCTACACAAGAAATATTTGTTTTACTCAGCAGGT

GTGCCTTAACCTCCCTATTCAGAAAGCTCCACATCAATAAACATGACACTCTGAAGTGAAAGTAGCCACG

AGAATTGTGCTACTTATACTGGTTCATAATCTGGAGGCAAGGTTCGACTGCAGCCGCCCCGTCAGCCTGT

GCTAGGCATGGTGTCTTCACAGGAGGCAAATCCAGAGCCTGGCTGTGGGGAAAGTGACCACTCTGCCCTG

ACCCCGATCAGTTAAGGAGCTGTGCAATAACCTTCCTAGTACCTGAGTGAGTGTGTAACTTATTGGGTTG

GCGAAGCCTGGTAAAGCTGTTGGAATGAGTATGTGATTCTTTTTAAGTATGAAAATAAAGATATATGTAC

AGACTTGTATTTTTTCTCTGGTGGCATTCCTTTAGGAATGCTGTGTGTCTGTCCGGCACCCCGGTAGGCC

TGATTGGGTTTCTAGTCCTCCTTAACCACTTATCTCCCATATGAGAGTGTGAAAAATAGGAACACGTGCT

CTACCTCCATTTAGGGATTTGCTTGGGATACAGAAGAGGCCATGTGTCTCAGAGCTGTTAAGGGCTTATT

TTTTTAAAACATTGGAGTCATAGCATGTGTGTAAACTTTAAATATGCAAATAAATAAGTATCTATGTCTA

AAAAAAAAAAAAAA

>NM_004048.2 *Homo sapiens* beta-2-microglobulin (B2M), mRNA
                                                                        (SEQ ID NO: 13)
AATATAAGTGGAGGCGTCGCGCTGGCGGGCATTCCTGAAGCTGACAGCATTCGGGCCGAGATGTCTCGCT

CCGTGGCCTTAGCTGTGCTCGCGCTACTCTCTCTTTCTGGCCTGGAGGCTATCCAGCGTACTCCAAAGAT

TCAGGTTTACTCACGTCATCCAGCAGAGAATGGAAAGTCAAATTTCCTGAATTGCTATGTGTCTGGGTTT

CATCCATCCGACATTGAAGTTGACTTACTGAAGAATGGAGAGAGAATTGAAAAAGTGGAGCATTCAGACT

TGTCTTTCAGCAAGGACTGGTCTTTCTATCTCTTGTACTACACTGAATTCACCCCCACTGAAAAAGATGA

GTATGCCTGCCGTGTGAACCATGTGACTTTGTCACAGCCCAAGATAGTTAAGTGGGATCGAGACATGTAA

GCAGCATCATGGAGGTTTGAAGATGCCGCATTTGGATTGGATGAATTCCAAATTCTGCTTGCTTGCTTTT

TAATATTGATATGCTTATACACTTACACTTTATGCACAAAATGTAGGGTTATAATAATGTTAACATGGAC

ATGATCTTCTTTATAATTCTACTTTGAGTGCTGTCTCCATGTTTGATGTATCTGAGCAGGTTGCTCCACA

GGTAGCTCTAGGAGGGCTGGCAACTTAGAGGTGGGGAGCAGAGAATTCTCTTATCCAACATCAACATCTT

GGTCAGATTTGAACTCTTCAATCTCTTGCACTCAAAGCTTGTTAAGATAGTTAAGCGTGCATAAGTTAAC

TTCCAATTTACATACTCTGCTTAGAATTTGGGGGAAAATTTAGAAATATAATTGACAGGATTATTGGAAA

-continued

TTTGTTATAATGAATGAAACATTTTGTCATATAAGATTCATATTTACTTCTTATACATTTGATAAAGTAA

GGCATGGTTGTGGTTAATCTGGTTTATTTTTGTTCCACAAGTTAAATAAATCATAAAACTTGATGTGTTA

TCTCTTA

>NM_002761.2 *Homo sapiens* protamine 1 (PRM1) , mRNA (SEQ ID NO: 14)

GACTCACAGCCCACAGAGTTCCACCTGCTCACAGGTTGGCTGGCTCAGCCAAGGTGGTGCCCTGCTCTGA

GCATTCAGGCCAAGCCCATCCTGCACCATGGCCAGGTACAGATGCTGTCGCAGCCAGAGCCGGAGCAGAT

ATTACCGCCAGAGACAAAGAAGTCGCAGACGAAGGAGGCGGAGCTGCCAGACACGGAGGAGAGCCATGAG

GTGCTGCCGCCCCAGGTACAGACCGCGATGTAGAAGACACTAATTGCACAAAATAGCACATCCACCAAAC

TCCTGCCTGAGAATGTTACCAGACTTCAAGATCCTCTTGCCACATCTTGAAAATGCCACCATCCAATAAA

AATCAGGAGCCTGCTAAGGAACAATGCCGCCTGTCAATAAATGTTGAAAGTCATCCCAAAAAAAAAAA

AAAAAA

---

US 12,577,618 B2

149

The invention claimed is:

1. A method for selecting a spermatozoon, comprising the following steps:

a) extracting nucleic acids from spermatozoa contained in a first spermatozoa sample previously obtained from a human subject;

b) measuring the expression level of at least one marker gene selected from the group consisting of AURKA, CFAP46, CCDC60, CCDC88B, HDAC4, and CACNA1C, or a combination thereof, from the extracted nucleic acids;

c) determining the presence or absence of an expression differential of the at least one marker gene compared to a control; and d) selecting the spermatozoon from a second spermatozoa sample previously obtained from the human subject: if there is an expression differential, the selection of the spermatozoon is carried out by observation at a magnification greater than ×5000; if there is no expression differential, the selection of the spermatozoon is carried out by observation at a magnification lower than ×500 wherein the control in step c) is the expression level of said at least one marker gene, measured in a spermatozoa sample with unaltered morphology, wherein in step b), the measurement of the expression level (Cp) of each gene is performed by quantitative real-time PCR (qPCR); and in step c), for a marker gene, the expression differential is calculated according to the following steps:

i) normalizing the expression level (Cp) of the marker gene measured in step b) to an expression level of a reference gene according to $$\Delta Cp_{GM} = [Cp_{GM}] - [Cp_{GR}]$$

150 where GM represents the marker gene and GR represents the reference gene; and then ii) determining the expression differential $\Delta\Delta Cp_{GM}$ according to $$\Delta\Delta Cp_{GM} = [\Delta Cp_{GM}] - [\Delta CP_{GM}]_{control}.$$

2. The method according to claim 1, wherein in step b), for each gene, the expression level is an average expression level obtained from an average of at least two measurements of expression level (Cp).

3. The method according to claim 1, wherein in step b) the expression level of a reference gene is:

the average expression level of said reference gene, or an average expression level of the reference genes calculated according to $$GRs \text{ Average } Cp = \frac{1}{k}\sum_{i=1}^{k}(GRi \text{ Average } Cp)$$

when the expression level of k reference genes is measured, k being greater than or equal to 2.

4. The method according to claim 1, wherein the existence of an expression differential is established when an expression differential of at least 10% is determined between the expression level of the at least one gene extracted from the spermatozoa sample and the control.

5. The method according to claim 1, wherein in step b, the expression level of at least two genes is measured.

6. The method according to claim 1, wherein in step b, the expression level of at least five genes is measured.

7. The method according to claim 1, wherein in step b, the expression level of at least six genes is measured.

* * * * *

SEQUENCE LISTING

<160> NUMBER OF SEQ ID NOS: 14

<210> SEQ ID NO 1
<211> LENGTH: 4425
<212> TYPE: DNA
<213> ORGANISM: Homo sapiens

<400> SEQUENCE: 1

```
acccagggcg gggcggcgcg ggcgttgcca cgacgcgggc cgcgcgcgtc cctggcagcc      60
aacccgtcca cgtcaaggtt tgtttaataa tcgccagggt atctatggcc gggctcaggc     120
ggctgctggg gagccaggag accgcgcggg acggcggatg aggcgcggcg gctgcggccc     180
agggcacctc ccctctggct tcccgaaccc ggccaggtcc gacccgaggg ggaggatgga     240
aacacctgcc gcgctctgag cccccagaa gagaacaccc ttcccgccat atcaccccac      300
ggtcctgcgg aggccaccgc ctggtccccc caagtctcca tcgcgcagcg tggggccgag     360
aggaatagtg agcgatggcg gaaaacctga aaagactggt ctcaaacgaa actttacgaa     420
cgttgcagga aaagctagac ttctggctga aggagtacaa cacaaacacg tgtgatcaaa     480
atctaaacca ttgccttgaa ctcattgagc aagttgccaa ggtgcaggga caactctttg     540
ggatcctcac agcagcagcc caagaaggag gacgtaatga tggtgtggaa acaatcaagt     600
cacgcctttt gccttggctg gaggcttcct ttactgctgc ttccctggga aaatctgttg     660
acagcaaggt cccctctctg caggacacgt ttgataggga gagacataaa gatcccagtc     720
ctcgggatcg ggatatgcaa cagttagact ctaatttgaa ctcaacccgg agtcaatgca     780
accaggttca agacgatctg gttgaaactg aaaagaatct tgaagaaagc aagaacagat     840
cggccatatc ccttttggct gcagaggagg aaataaatca gctgaaaaag cagcttaaat     900
ctcttcaagc tcaggaggat gcccgccaca gaaacacaga tcagaggagc tcagagaata     960
ggcggtcaga gccttggagc ttggaggagc ggaagcgtga gcagtggaac tcactcaagc    1020
agaatgcaga ccagcaggac acagaagcca tgtccgatta taagaaacag ctccgaaacc    1080
tgaaggagga gatagctgtt ctgtctgctg agaaaagtgc actccaagga aggtcctcca    1140
ggagccggtc tcccagccct gccctcgca gccgtagctg cagccgcagc agatctgcca     1200
gcccctccac cgctgtcaag gtcaggagac cgtccccaaa ccgctccaag ctgtccaatg    1260
tggcgcgcaa ggctgccctc ttgtcccggt tcagcgattc ctattcccag gcccgcctgg    1320
```

-continued

```
acgcgcagtg cctgctgcgg cgctgcatcg acaaggctga gaccgttcag cggatcatct    1380
acatcgccac agtggaggca ttccatgtag caaaaatggc attcagacac ttcaagatcc    1440
atgtgagaaa atcgttgaca ccatcttatg tggggtcgaa tgactttgag aatgctgtct    1500
tggattatgt catttgtcat cttgatctat atgattctca aagcagtgtc aatgatgtga    1560
tccgagccat gaatgtcaat cccaagattt cattccctcc tgtcgttgac tttttgccttc    1620 tcagtgactt catccaggag atatgttgca ttgcctttgc aatgcaggcc ttagaaccac    1680
ccctagatat tgcatatgga gcagatggag aagtttttaa tgattgcaaa taccgccgca    1740
gctacgactc ggatttcact gctcccttag tcctctatca cgtgtggcct gctctcatgg    1800
agaatgactg tgtcattatg aagggagaag ctgtcaccag gagaggggct ttttggaatt    1860
cggtgcgatc tgtaagtcgt tgtcgaagca ggagtttaag tcccatttgc ccccgtagcc    1920
aaattggttt aaacacgatg tctcgaagtc ggagtccttc tccaataaga tgtggattgc    1980
caagatttta aaagcaccag acctgctcct ttgacccagt gcgtggaaac agctgctttc    2040
tccagtgccg ccatctgtct tctgtgtctg cctcagacct cacttaagat aatgtcaaaa    2100
ggcaattctg tgtatcaccc cacacagaga gttaaatgtt ttggcttggc gcatttgtaa    2160
ctttagatat attgcattct attttatttt atagatacta attccattaa tttcataaaa    2220
atgattgtat aggcatttag gatcatattc attcgaagca aagtccgtta caaaggttca    2280
agatttccat ctcaaaacac tacgctcttt tatgggaact gtgtgaactg aagtggaaag    2340
catctaccat gctgaggcta aaagaaaaga tgaatcattt tagtttgcag atggatcgta    2400
aatataattg ttggtatcag ctttagctca aaaccaatat taggtgtttt aatttccttt    2460
taaggtttgg aagacagccc taatctcagg ttggggagct catgttagta gcagtgactt    2520
aaggctaagt gtagaagata atttaagata cattttcttt atatattagc caacaaatta    2580
tatttattgg ttggcttgct tttccgttct gattttgaga gtgcccagtt tggtttagtt    2640
gaccaatgaa tgtcaaagct acttagttga gagaatttcc ttgttcataa atgtagagca    2700
gtgatttgat tagaagccag ctttgagata aatgttaatt acctcatgca tatctcctgg    2760
gaatatttca aactgtttta atgcatgtgt tatatataaa agtttcttgg gacatgctct    2820
tcacctgttc tacctagtta tttgcaaatt cagacctcct attgaactct gtctgaccaa    2880
aactacttaa actcaaggcc caaaactagg ggcaccattt actgatttta aattgagtat    2940
atatcccttg acttcttcac tgtcaaatac ttttgaaact tcacgttcaa gataagaatg    3000
gaatgttgct ttcttgcaat aagtaatgtt ctttctgcct ttttttcact tttaagtcag    3060
ccttaaacac atgcctcaca aacatctact ttctccacat acctttgaga gagacactga    3120
attggcctca gctcagtttt gcataagctt agtgccagaa ccagcacctg atgctttttca    3180 ggtgaaaata aaacaaacag cttctctaaa gcatcttacc cctgtgctgg aggtttgagg    3240
gacctcttca gtgcctgccc cttgagtcta atggtcacca cctcattctg aagtatgagt    3300
tgaatttttt gccctctttg catatttaca ttagtcatca ctttgaagca atgcagtgtg    3360
ctggaaggag cactatctgc ctaggtaact gctagtcatg acttggtcat cagcttgctt    3420
tgtggcactg agcaagttac ttcacttctc tgagccttgg ttttatcata gggtgaggag    3480
gttggataca attagtgccc ctcttaaccc tgcagactca atgttccctt ttataacaag    3540
tattttattc tgaatatgaa atgaaaatta aagttaatat aatcatctat gtgcatgtat    3600
aattttaagc agtgaacata gtaccctaac tataatataa agcagaaaaa aaggcaactt    3660
ttaataaaat aaaatgtatt tcaataaaaa agcttgggta taaccaccct agaagataaa    3720
```

-continued

```
attaagtcat tagatggctg aacctgcatg tagagccacc agctacaaat gaaaatcaat    3780
gtgtgtattg gcaacagaaa atcacggtgt tgtcattgga tgtgactttc tgaagtggtg    3840
ggcaattctt gttaatgttt taaacaaaaa aaaaaaaacc ttacagtctt gccctgattt    3900
acacagcagt cacattcctg gaaaattcaa gtgtttatta aaactatgca acagttactg    3960
tgtgttatac gttgaaaggt cttcactaat atctcactaa gtaatgagaa tgcctacata    4020
tcagaatttt tttttcagg agccaagcac atatactgat ttggaaaaag gcacaggtag     4080
ctcagtttat ttgctttcta ccctgcctgg ccacttgctg tttcttcagt ttctaatttg    4140
agctgtaact acacaaggaa agctaaatag tctggaaaat ttttggaaag aatccacaaa    4200
gccaaaggag actggcctat actcatttta tctggggatg taccttaccc ttagagactt    4260
tgaaaaatgt gaagctctta ttttgtaacc tgggtaaatg ttagtttcta gattttcggc    4320
ttaacatcta ataataacat ttaaaaagtg cttttgtaac tattagttat ttgcaataaa    4380
atgctttcct tctacagtcc caagttcaaa aaaaaaaaaa aaaaa                    4425
```

```
<210> SEQ ID NO 2
<211> LENGTH: 4329
<212> TYPE: DNA
<213> ORGANISM: Homo sapiens

<400> SEQUENCE: 2
```

```
acccagggcg gggcggcgcg ggcgttgcca cgacgcgggc cgcgcgcgtc cctggcagcc    60
aacccgtcca cgtcaaggtt tgtttaataa tcgccagggt atctatggcc gggctcaggc    120
ggctgctggg gagccaggag accgcgcggg acggcggatg aggcgcggcg gctgcggccc    180
agggcacctc ccctctggct tcccgaaccc ggccaggtcc gacccgaggg ggaggatgga    240
aacacctgcc gcgctctgag ccccccagaa gagaacaccc ttcccgccat atcaccccac    300
ggtcctgcgg aggccaccgc ctggtccccc caagtctcca tcgcgcagcg tggggccgag    360
aggaatagtg agcgatggcg gaaaacctga aaagactggt ctcaaacgaa actttacgaa    420
cgttgcagga aaagctagac ttctggctga aggagtacaa cacaaacacg tgtgatcaaa    480
atctaaacca ttgccttgaa ctcattgagc aagttgccaa ggtgcaggga caactctttg    540
ggatcctcac agcagcagcc caagaaggag gacgtaatga tggtgtggaa acaatcaagt    600
cacgcctttt gccttggctg gaggcttcct ttactgctgc ttccctggga aaatctgttg    660
acagcaaggt cccctctctg caggacacgt ttgatgggga gagacataaa gatcccagtc    720
ctcgggatcg ggatatgcaa cagttagact ctaatttgaa ctcaacccgg agtcaatgca    780
accaggttca agacgagctt aaatctcttc aagctcagga ggatgcccgc cacagaaaca    840
cagatcagag gagctcagag aataggcggt cagagccttg gagcttggag gagcggaagc    900
gtgagcagtg gaactcactc aagcagaatg cagaccagca ggacacagaa gccatgtccg    960
attataagaa acagctccga aacctgaagg aggagatagc tgttctgtct gctgagaaaa    1020
gtgcactcca aggaaggtcc tccaggagcc ggtctcccag ccctgcccct cgcagccgta    1080
gctgcagccg cagcagatct gccagcccct ccaccgctgt caaggtcagg agaccgtccc    1140
caaaccgctc caagctgtcc aatgtggcgc gcaaggctgc cctcttgtcc cggttcagcg    1200
attcctattc ccaggcccgc ctggacgcgc agtgcctgct gcggcgctgc atcgacaagg    1260
ctgagaccgt tcacgggatc atctacatcg ccacagtgga ggcattccat gtagcaaaaa    1320
tggcattcag acacttcaag atccatgtga gaaaatcgtt gacaccatct tatgtggggt    1380
```

```
cgaatgactt tgagaatgct gtcttggatt atgtcatttg tcatcttgat ctatatgatt      1440
ctcaaagcag tgtcaatgat gtgatccgag ccatgaatgt caatcccaag atttcattcc      1500
ctcctgtcgt tgacttttgc cttctcagtg acttcatcca ggagatatgt tgcattgcct      1560
ttgcaatgca ggccttagaa ccacccctag atattgcata tggagcagat ggagaagttt      1620
ttaatgattg caaataccgc cgcagctacg actcggattt cactgctccc ttagtcctct      1680
atcacgtgtg gcctgctctc atggagaatg actgtgtcat tatgaaggga gaagctgtca      1740
ccaggagagg ggcttttttgg aattcggtgc gatctgtaag tcgttgtcga agcaggagtt      1800
taagtcccat ttgcccccgt agccaaattg gtttaaacac gatgtctcga agtcggagtc      1860
cttctccaat aagatgtgga ttgccaagat tttaaaagca ccagacctgc tcctttgacc      1920
cagtgcgtgg aaacagctgc tttctccagt gccgccatct gtcttctgtg tctgcctcag      1980
acctcactta agataatgtc aaaaggcaat tctgtgtatc accccacaca gagagttaaa      2040
tgttttggct tggcgcattt gtaactttag atatattgca ttctatttta ttttatagat      2100
actaattcca ttaatttcat aaaaatgatt gtataggcat ttaggatcat attcattcga      2160
agcaaagtcc gttacaaagg ttcaagattt ccatctcaaa acactacgct cttttatggg      2220
aactgtgtga actgaagtgg aaagcatcta ccatgctgag gctaaaagaa aagatgaatc      2280
attttagttt gcagatggat cgtaaatata attgttggta tcagctttag ctcaaaacca      2340
atattaggtg ttttaatttc cttttaaggt ttggaagaca gccctaatct caggttgggg      2400
agctcatgtt agtagcagtg acttaaggct aagtgtagaa gataatttaa gatacatttt      2460
ctttatatat tagccaacaa attatattta ttggttggct tgcttttccg ttctgatttt      2520
gagagtgccc agtttggttt agttgaccaa tgaatgtcaa agctacttag ttgagagaat      2580
ttccttgttc ataaatgtag agcagtgatt tgattagaag ccagctttga gataaatgtt      2640
aattacctca tgcatatctc ctgggaatat ttcaaactgt tttaatgcat gtgttatata      2700
taaaagtttc ttgggacatg ctcttcacct gttctaccta gttatttgca aattcagacc      2760
tcctattgaa ctctgtctga ccaaaactac ttaaactcaa ggcccaaaac tagggggcacc      2820 atttactgat tttaaattga gtatatatcc cttgacttct tcactgtcaa atactttttga      2880 aacttcacgt tcaagataag aatggaatgt tgctttcttg caataagtaa tgttctttct      2940
gccttttttt cactttttaag tcagccttaa acacatgcct cacaaacatc tactttctcc      3000
acataccttt gagagagaca ctgaattggc ctcagctcag ttttgcataa gcttagtgcc      3060
agaaccagca cctgatgctt ttcaggtgaa aataaaacaa acagcttctc taaagcatct      3120 taccccctgtg ctggaggttt gagggacctc ttcagtgcct gcccccttgag tctaatggtc      3180 accacctcat tctgaagtat gagttgaatt ttttgccctc tttgcatatt tacattagtc      3240
atcactttga agcaatgcag tgtgctggaa ggagcactat ctgcctaggt aactgctagt      3300
catgacttgg tcatcagctt gctttgtggc actgagcaag ttacttcact tctctgagcc      3360 ttggtttttat cataggggtga ggaggttgga tacaattagt gcccctctta accctgcaga      3420
ctcaatgttc ccttttataa caagtatttt attctgaata tgaaatgaaa attaaagtta      3480
atataatcat ctatgtgcat gtataatttt aagcagtgaa catagtaccc taactataat      3540
ataaagcaga aaaaaaggca acttttaata aaataaaatg tatttcaata aaaaagcttg      3600
ggtataacca ccctagaaga taaaattaag tcattagatg gctgaacctg catgtagagc      3660
caccagctac aaatgaaaat caatgtgtgt attggcaaca gaaaatcacg gtgttgtcat      3720
tggatgtgac tttctgaagt ggtgggcaat tcttgttaat gtttttaaaca aaaaaaaaaa      3780
```

-continued

```
aaccttacag tcttgccctg atttacacag cagtcacatt cctggaaaat tcaagtgttt      3840
attaaaacta tgcaacagtt actgtgtgtt atacgttgaa aggtcttcac taatatctca      3900
ctaagtaatg agaatgccta catatcagaa tttttttttt caggagccaa gcacatatac      3960
tgatttggaa aaaggcacag gtagctcagt ttatttgctt tctaccctgc ctggccactt      4020
gctgtttctt cagtttctaa tttgagctgt aactacacaa ggaaagctaa atagtctgga      4080
aaatttttgg aaagaatcca caaagccaaa ggagactggc ctatactcat tttatctggg      4140
gatgtacctt acccttagag actttgaaaa atgtgaagct cttattttgt aacctgggta      4200
aatgttagtt tctagatttt cggcttaaca tctaataata acatttaaaa agtgcttttg      4260
taactattag ttatttgcaa taaaatgctt tccttctaca gtcccaagtt caaaaaaaaa      4320
aaaaaaaaa                                                              4329
```

<210> SEQ ID NO 3
<211> LENGTH: 2455
<212> TYPE: DNA
<213> ORGANISM: Homo sapiens

<400> SEQUENCE: 3

```
agttgcctac tttccccgca gtgcgataaa cccctcgttg gggccgcctt agttctcggc        60
cgctctcgga ggatggcgat ctgggagccc ctccatggga cccctctcac actttgtcac       120
tggaatttta tttatttttt agttcatatt ttattttgct tatagaagag aaagatatcc       180
cttccgaaga ggaggaagct tacagaagtt tataaccttt caaaaagtaa ataagtccag       240
gcttgcctga ttctgcccta cccggacttc cttatcccgt ctgtgggaga cccaggtgct       300
ttctcattac tcttcagaag gaaaccgctt tggagttcgt gtaattggga cttggggatc       360
agggagaagt tgccgaaact tctcatacca gtaactactg aagtagaaga ttctggaaaa       420
atccttgtct tgggggcaca ggctaaaacc tgaaggattt ttaagatgac caaggttcca       480
gccaccaaga agcttcagag ttcccccaac tcggggggctg tccggccctt ttatgcctcg       540
gagaacctaa ggcaggtccc agacaagcca atgaagagca tcaagtatat ggacaaggaa       600
ataataaacc tcaaaaagga ccttatacga agccgctttt tgatccagtc tgtgaagata       660
ggccgtggat attttgctat tctgagggaa gagactgcaa agaaaaagaa gcaacaacaa       720
cttcagaaac tgaaagagga ggaaagaaat aaattccagc cagccgaaaa gatctcagaa       780
atccactatg gggacacctt attgagcaca tatgatgatg agaagttgaa gacactggga       840
gctagagtca cacgtcgccc attcactccc atccacagct gcatcatttc tccctcgcta       900
accgaggctc acgtcgagcc cctcttccgc cagctctgtg ctctccactg gcttctggag       960
gccctgacta ttgaccacac ccaccacacc atgaagcctg tgatcacctg ctggaacccca     1020 aaggacccgg gtggaagcaa gagcaccatt aaaaaaatca ataaggacaa gtccatggga     1080
cagaaatggg agcatttcat cacagcgcca aagaccaaga aattcaaaat tcccacaatg     1140
cgagtcacca accgcaaacc aagccggcga ggctccacac tcagtctgag tcgggccagt     1200 gggggtcct ctccccagag cagcatgatc tctgtgaacc ctggctcgga tgagccccca     1260
agtgtgaaca cccaggtgac cagcagcaag gacattgagg acaatgagtc atcttcaacc     1320
aagccagatg aagaacctct gtatatgaat ctgcagaagc tcctggagat ggttcgggaa     1380
gatgcccgga ggacagtcac aatagaaaat gggatgcaaa gaaaagcacc cagcatcttg     1440
tcagtgctga aacaaaacaa gagtaattct gcttataagg aaatgcagac cactctcaaa     1500
```

-continued

```
tcaagtgaga gatccagcag tacaagtgca gaaagccaca tccaaccagt ccagaagaag    1560
tctaaaaacc gcactaattg tgacatcaac atccactaca agagtggggt gtgtaacacc    1620
atgagggcca agttttacag cgtagcccag gaggctggct tctgcctgca ggacaagatg    1680
gaaatcctca tgaagcgcca agaagagaga ggtatccaga agttccgtgc ttttgtcctt    1740
gtctcaaatt ttcaaaagga catagcaaaa atgagacatc acatatctgt agtaaaagga    1800
gatgcagaag aaattgcaga ccactggtac tttgatctgt tgtccaaact gccagaggat    1860
ctaaagaact tccgccccgc caaaaagatc ctggtgaaac tgcagaagtt tggagaaaac    1920
ctggacttgc ggattcgacc ccatgtcctc ctgaaggtgc tgcaggatct gaggatttgg    1980
gaactgtgct cccctgacat cgctgtggct attgagtttg tgcgagaaca catcatccat    2040
atgcctcaag aggattacat cagctggctg cagagccgga tcaacatacc cattgggccc    2100
tacagcgccc tgaggtaggc tgggcctggg ttgaccagct gtctcagtgg aggagtgttt    2160
gcctatatca tgttcctgta tcctgcctgt gttcctgcct cctgactacc ctcatggatg    2220
ctctttatgg atgacccttt acagtagggt catctggaga ctgacttcca gcaacatttt    2280 tagagggggga tggccccggt ggccctcccc tcaattccac accccagacc caacctacca    2340
gtctctgttc ttcaatgatc cagcctgact ctacctactt cctcttcaga ttccttcacc    2400
ctatttacct tcctcaagta ctggagaata aaattgaact gaatgtttga aaaaa         2455
```

<210> SEQ ID NO 4
<211> LENGTH: 8079
<212> TYPE: DNA
<213> ORGANISM: Homo sapiens

<400> SEQUENCE: 4

```
cgaggccgcc gccgtcgcct ccgccgggcg agccggagcc ggagtcgagc cgcggccggg      60
agccgggcgg gctggggacg cgggccgggg gcggaggcgc tgggggccgg ggccggggcc     120
gggggcggag gcgctggggg ccggggccgg ggccgggcgc cgagcggggt ccgcggtgac     180
cgcgccgccc gggcgatgcc cgcggggacg ccgccggcca gcagagcgag gtgctgccgg     240
ccgccaccat gaccgagggc gcacgggccg ccgacgaggt ccgggtgccc ctgggcgcgc     300 cgcccctgg ccctgcggcg ttggtggggg cgtccccgga gagccccggg gcgccgggac      360
gcgaggcgga gcgggggtcc gagctcggcg tgtcaccctc cgagagcccg gcggccgagc     420
gcggcgcgga gctgggtgcc gacgaggagc agcgcgtccc gtacccggcc ttggcggcca     480
cggtcttctt ctgcctcggt cagaccacgc ggccgcgcag ctggtgcctc cggctggtct     540
gcaacccatg gttcgagcac gtgagcatgc tggtaatcat gctcaactgc gtgaccctgg     600
gcatgttccg gccctgtgag gacgttgagt gcggctccga gcgctgcaac atcctggagg     660
cctttgacgc cttcattttc gccttttttg cggtggagat ggtcatcaag atggtggcct     720
tggggctgtt cggggcagaag tgttacctgg gtgacacgtg gaacaggctg gatttcttca     780
tcgtcgtggc gggcatgatg gagtactcgt tggacggaca caacgtgagc ctctcggcta     840
tcaggaccgt gcgggtgctg cggcccctcc gcgccatcaa ccgcgtgcct agcatgcgga     900
tcctggtcac tctgctgctg gatacgctgc ccatgctcgg gaacgtcctt ctgctgtgct     960
tcttcgtctt cttcattttc ggcatcgttg gcgtccagct ctgggctggc ctcctgcgga    1020
accgctgctt cctggacagt gcctttgtca ggaacaacaa cctgaccttc ctgcggccgt    1080
actaccagac ggaggagggc gaggagaacc cgttcatctg ctcctcacgc cgagacaacg    1140
gcatgcagaa gtgctcgcac atccccggcc gccgcgagct gcgcatgccc tgcaccctgg    1200
```

-continued

```
gctgggaggc ctacacgcag ccgcaggccg agggggtggg cgctgcacgc aacgcctgca      1260
tcaactggaa ccagtactac aacgtgtgcc gctcgggtga ctccaacccc cacaacggtg      1320
ccatcaactt cgacaacatc ggctacgcct ggattgccat cttccaggtg atcacgctgg      1380
aaggctgggt ggacatcatg tactacgtca tggacgccca ctcattctac aacttcatct      1440
atttcatcct gctcatcatc gtgggctcct tcttcatgat caacctgtgc ctggtggtga      1500
ttgccacgca gttctcggag acgaagcagc gggagagtca gctgatgcgg gagcagcggg      1560
cacgccacct gtccaacgac agcacgctgg ccagcttctc cgagcctggc agctgctacg      1620
aagagctgct gaagtacgtg ggccacatat tccgcaaggt caagcggcgc agcttgcgcc      1680
tctacgcccg ctggcagagc cgctggcgca agaaggtgga ccccagtgct gtgcaaggcc      1740
agggtcccgg gcaccgccag cgccgggcag gcaggcacac agcctcggtg caccacctgg      1800
tctaccacca ccatcaccac caccaccacc actaccattt cagccatggc agcccccgca      1860
ggcccggccc cgagccaggc gcctgcgaca ccaggctggt ccgagctggc gcgcccccct      1920
cgccaccttc cccaggccgc ggacccccg acgcagagtc tgtgcacagc atctaccatg      1980
ccgactgcca catagagggg ccgcaggaga gggcccgggt ggcacatgcc gcagccactg      2040
ccgctgccag cctcagactg gccacagggc tgggcaccat gaactacccc acgatcctgc      2100
cctcaggggt gggcagcggc aaaggcagca ccagccccgg acccaagggg aagtgggccg      2160
gtggaccgcc aggcaccggg gggcacggcc cgttgagctt gaacagccct gatccctacg      2220
agaagatccc gcatgtggtc ggggagcatg gactgggcca ggccctggc catctgtcgg       2280 gcctcagtgt gccctgcccc ctgcccagcc ccccagcggg cacactgacc tgtgagctga      2340
agagctgccc gtactgcacc cgtgccctgg aggacccgga gggtgagctc agcggctcgg      2400
aaagtggaga ctcagatggc cgtggcgtct atgaattcac gcaggacgtc cggcacggtg      2460
accgctggga ccccacgcga ccaccccgtg cgacggacac accaggccca ggcccaggca      2520
gcccccagcg gcgggcacag cagagggcag ccccgggcga gccaggctgg atgggccgcc      2580
tctgggttac cttcagcggc aagctgcgcc gcatcgtgga cagcaagtac ttcagccgtg      2640
gcatcatgat ggccatcctt gtcaacacgc tgagcatggg cgtggagtac catgagcagc      2700
ccgaggagct gactaatgct ctggagatca gcaacatcgt gttcaccagc atgtttgccc      2760
tggagatgct gctgaagctg ctggcctgcg gccctctggg ctacatccgg aacccgtaca      2820
acatcttcga cggcatcatc gtggtcatca gcgtctggga gatcgtgggg caggcggacg      2880
gtggcttgtc tgtgctgcgc accttccggc tgctgcgtgt gctgaagctg gtgcgctttc      2940
tgccagccct gcggcgccag ctcgtggtgc tggtgaagac catggacaac gtggctacct      3000
tctgcacgct gctcatgctc ttcattttca tcttcagcat cctgggcatg cacctttttcg     3060 gctgcaagtt cagcctgaag acagacaccg agacaccgt gcctgacagg aagaacttcg       3120
actccctgct gtgggccatc gtcaccgtgt tccagatcct gacccaggag gactggaacg      3180
tggtcctgta caacggcatg gcctccacct cctcctgggc cgccctctac ttcgtggccc      3240
tcatgacctt cggcaactat gtgctcttca acctgctggt ggccatcctc gtggagggct      3300
tccaggcgga gggcgatgcc aacagatccg acacggacgg ggacaagacg tcggtccact      3360
tcgaggagga cttccacaag ctcagagaac tccagaccac agagctgaag atgtgttccc      3420
tggccgtgac ccccaacggg cacctggagg acgaggcag cctgtcccct ccctcatca       3480 tgtgcacagc tgccacgccc atgcctaccc ccaagagctc accattcctg gatgcagccc      3540
```

-continued

```
ccagcctccc agactctcgg cgtggcagca gcagctccgg ggacccgcca ctgggagacc      3600
agaagcctcc ggccagcctc cgaagttctc cctgtgcccc ctggggcccc agtggcgcct      3660
ggagcagccg gcgctccagc tggagcagcc tgggccgtgc ccccagcctc aagcgccgcg      3720
gccagtgtgg ggaacgtgag tccctgctgt ctggcgaggg caagggcagc accgacgacg      3780
aagctgagga cggcagggcc gcgcccgggc cccgtgccac cccactgcgg cgggccgagt      3840
ccctggaccc acggcccctg cggccggccg ccctcccgcc taccaagtgc cgcgatcgcg      3900
acgggcaggt ggtggccctg cccagcgact tcttcctgcg catcgacagc caccgtgagg      3960
atgcagccga gcttgacgac gactcggagg acagctgctg cctccgcctg cataaagtgc      4020
tggagcccta caagccccag tggtgccgga gccgcgaggc ctgggccctc tacctcttct      4080
ccccacagaa ccggttccgc gtctcctgcc agaaggtcat cacacacaag atgtttgatc      4140
acgtggtcct cgtcttcatc ttcctcaact gcgtcaccat cgccctggag aggcctgaca      4200
ttgatcccgg cagcaccgag cgggtcttcc tcagcgtctc caattacatc ttcacggcca      4260
tcttcgtggc ggagatgatg gtgaaggtgg tggccctggg gctgctgtcc ggcgagcacg      4320
cctacctgca gagcagctgg aacctgctgg atgggctgct ggtgctggtg tccctggtgg      4380
acattgtcgt ggccatggcc tcggctggtg cgccaagat cctgggtgtt ctgcgcgtgc      4440
tgcgtctgct gcggacccctg cggcctctga gggtcatcag ccgggcccccg ggcctcaagc      4500 tggtggtgga gacgctgata tcatcactca ggcccattgg gaacatcgtc ctcatctgct      4560
gcgccttctt catcattttt ggcattttgg gtgtgcagct cttcaaaggg aagttctact      4620
actgcgaggg ccccgacacc aggaacatct ccaccaaggc acagtgccgg gccgcccact      4680
accgctgggt gcgacgcaag tacaacttcg acaacctggg ccaggccctg atgtcgctgt      4740
tcgtgctgtc atccaaggat ggatgggtga acatcatgta cgacgggctg gatgccgtgg      4800
gtgtcgacca gcagcctgtg cagaaccaca accctggat gctgctgtac ttcatctcct      4860
tcctgctcat cgtcagcttc ttcgtgctca acatgttcgt gggcgtcgtg gtcgagaact      4920
tccacaagtg ccggcagcac caggaggcgg aggaggcgcg gcggcgagag gagaagcggc      4980
tgcggcgcct agagaggagg cgcaggaagg cccagcgccg gcctactat gccgactact      5040 cgcccacgcg ccgctccatt cactcgctgt gcaccagcca ctatctcgac ctcttcatca      5100
ccttcatcat ctgtgtcaac gtcatcacca tgtccatgga gcactataac caacccaagt      5160
cgctggacga ggccctcaag tactgcaact acgtcttcac catcgtgttt gtcttcgagg      5220
ctgcactgaa gctggtagca tttgggttcc gtcggttctt caaggacagg tggaaccagc      5280
tggacctggc catcgtgctg ctgtcactca tgggcatcac gctggaggag atagagatga      5340
gcgccgcgct gcccatcaac cccaccatca tccgcatcat gcgcgtgctt cgcattgccc      5400
gtgtgctgaa gctgctgaag atggctacgg gcatgcgcgc cctgctggac actgtggtgc      5460
aagctctccc ccaggtgggg aacctgggcc ttctttttcat gctcctgttt tttatctatg      5520
ctgcgctggg agtggagctg ttcggaggc tggagtgcag tgaagacaac ccctgcgagg      5580
gcctgagcag gcacgccacc ttcagcaact tcggcatggc cttcctcacg ctgttccgcg      5640
tgtccacggg ggacaactgg aacgggatca tgaaggacac gctgcgcgag tgctcccgtg      5700
aggacaagca ctgcctgagc tacctgccgg ccctgtcgcc cgtctacttc gtgaccttcg      5760
tgctggtggc ccagttcgtg ctggtgaacg tggtggtggc cgtgctcatg aagcacctgg      5820
aggagagcaa caaggaggca cgggaggatg cggagctgga cgccgagatc gagctggaga      5880
tggcgcaggg ccccgggagt gcacgccggg tggacgcgga caggcctccc ttgcccagg      5940
```

-continued

```
agagtccggg cgccagggac gccccaaacc tggttgcacg caaggtgtcc gtgtccagga    6000
tgctctcgct gcccaacgac agctacatgt tcaggcccgt ggtgcctgcc tcggcgcccc    6060 accccgccc gctgcaggag gtggagatgg agacctatgg ggccggcacc cccttgggct     6120
ccgttgcctc tgtgcactct ccgcccgcag agtcctgtgc ctccctccag atcccattgg     6180
ctgtgtcgtc cccagccagg agcggcgagc ccctccacgc cctgtccct cggggcacag      6240 cccgctcccc cagtctcagc cggctgctct gcagacagga ggctgtgcac accgattcct     6300
tggaagggaa gattgacagc cctagggaca ccctggatcc tgcagagcct ggtgagaaaa     6360
ccccggtgag gccggtgacc caggggggct ccctgcagtc cccaccacgc tccccacggc     6420
ccgccagcgt ccgcactcgt aagcatacct tcggacagcg ctgcgtctcc agccggccgg     6480
cggccccagg cggagaggag gccgaggcct cggacccagc cgacgaggag gtcagccaca     6540
tcaccagctc cgcctgcccc tggcagccca cagccgagcc ccatggcccc gaagcctctc     6600
cggtggccgg cggcgagcgg gacctgcgca ggctctacag cgtggatgct cagggcttcc     6660
tggacaagcc gggccgggca gacgagcagt ggcggccctc ggcggagctg ggcagcgggg    6720
agcctgggga ggcgaaggcc tggggccctg aggccgagcc cgctctgggt gcgcgcagaa     6780
agaagaagat gagcccccc tgcatctcgg tggaacccc tgcggaggac gagggctctg       6840
cgcggccctc cgcggcagag ggcggcagca ccacactgag gcgcaggacc ccgtcctgtg     6900
aggccacgcc tcacagggac tccctggagc ccacagaggg ctcaggcgcc gggggggacc     6960
ctgcagccaa ggggggagcgc tggggccagg cctcctgccg ggctgagcac ctgaccgtcc    7020
ccagctttgc ctttgagccg ctggacctcg gggtccccag tggagaccct ttcttggacg     7080
gtagccacag tgtgaccca gaatccagag cttcctcttc aggggccata gtgcccctgg      7140
aacccccaga atcagagcct cccatgcccg tcggtgaccc cccagagaag aggcgggggc     7200
tgtacctcac agtcccccag tgtcctctgg agaaaccagg gtccccctca gccacccctg     7260 ccccagggggg tggtgcagat gacccgtgt agctcggggc ttggtgccgc ccacggcttt     7320
ggccctgggg tctggggggcc ccgctggggt ggaggcccag gcagaaccct gcatggaccc    7380
tgacttgggt cccgtcgtga gcagaaaggc ccggggagga tgacggccca ggccctggtt    7440
ctctgcccag cgaagcagga gtagctgccg ggcccacga gcctccgtcc gttctggttc     7500
gggtttctcc gagttttgct accagccgag gctgtgcggg caactgggtc agcctcccgt     7560
caggagagaa gccgcgtctg tgggacgaag accgggcacc cgccagagag gggaaggtac     7620
caggttgcgt cctttcaggc cccgcgttgt tacaggacac tcgctggggg ccctgtgccc     7680
ttgccggcgg caggttgcag ccaccgcggc ccaatgtcac cttcactcac agtctgagtt    7740
cttgtccgcc tgtcacgccc tcaccaccct ccccttccag ccaccaccct ttccgttccg     7800
ctcgggcctt cccagaagcg tcctgtgact ctgggagagg tgacacctca ctaaggggcc     7860
gaccccatgg agtaacgcgc ccggccccga tgcgaatcag gcctcccta catctggggg     7920 cgttggccgc gagattccca ttgacacctt tgtttcgtgt gcttttaaat tcaggttaaa     7980
tgttgcaata atctgatgca gaagactcag cttctcaagg gagagggagg gggcggagcg    8040
gaataaatag taacttattt aagaaatgca aaaaaaaaa                            8079
```

<210> SEQ ID NO 5
<211> LENGTH: 8097
<212> TYPE: DNA
<213> ORGANISM: Homo sapiens

```
<400> SEQUENCE: 5
cgaggccgcc gccgtcgcct ccgccgggcg agccggagcc ggagtcgagc cgcggccggg      60
agccgggcgg gctggggacg cgggccgggg gcggaggcgc tggggggccgg ggccgggggcc     120 gggggcggag gcgctggggg ccggggccgg ggccgggcgc cgagcggggt ccgcggtgac     180
cgcgccgccc gggcgatgcc cgcggggacg ccgccggcca gcagagcgag gtgctgccgg     240
ccgccaccat gaccgagggc gcacgggccg ccgacgaggt ccgggtgccc ctgggcgcgc     300 cgcccctgg ccctgcggcg ttggtggggg cgtccccgga gagcgggg gcgccgggac     360 gcgaggcgga gcgggggtcc gagctcggcg tgtcaccctc cgagagcccg gcggccgagc     420
gcggcgcgga gctgggtgcc gacgaggagc agcgcgtccc gtacccggcc ttggcggcca     480
cggtcttctt ctgcctcggt cagaccacgc ggccgcgcag ctggtgcctc cggctggtct     540
gcaacccatg gttcgagcac gtgagcatgc tggtaatcat gctcaactgc gtgaccctgg     600
gcatgttccg gccctgtgag gacgttgagt gcggctccga gcgctgcaac atcctggagg     660
cctttgacgc cttcattttc gcttttttg cggtggagat ggtcatcaag atggtggcct     720
tggggctgtt cgggcagaag tgttacctgg gtgacacgtg gaacaggctg gatttcttca     780
tcgtcgtggc gggcatgatg gagtactcgt tggacggaca caacgtgagc ctctcggcta     840
tcaggaccgt gcgggtgctg cggcccctcc gcgccatcaa ccgcgtgcct agcatgcgga     900
tcctggtcac tctgctgctg gatacgctgc ccatgctcgg gaacgtcctt ctgctgtgct     960
tcttcgtctt cttcatttc ggcatcgttg gcgtccagct ctgggctggc ctcctgcgga    1020
accgctgctt cctggacagt gcctttgtca ggaacaacaa cctgaccttc ctgcggccgt    1080
actaccagac ggaggagggc gaggagaacc cgttcatctg ctcctcacgc cgagacaacg    1140
gcatgcagaa gtgctcgcac atccccggcc gccgcgagct gcgcatgccc tgcaccctgg    1200
gctgggaggc ctacacgcag ccgcaggccg agggggtggg cgctgcacgc aacgcctgca    1260
tcaactggaa ccagtactac aacgtgtgcc gctcgggtga ctccaacccc cacaacggtg    1320
ccatcaactt cgacaacatc ggctacgcct ggattgccat cttccaggtg atcacgctgg    1380
aaggctgggt ggacatcatg tactacgtca tggacgccca ctcattctac aacttcatct    1440
atttcatcct gctcatcatc gtgggctcct tcttcatgat caacctgtgc ctggtggtga    1500
ttgccacgca gttctcggag acgaagcagc gggagagtca gctgatgcgg gagcagcggg    1560
cacgccacct gtccaacgac agcacgctgg ccagcttctc cgagcctggc agctgctacg    1620
aagagctgct gaagtacgtg ggccacatat tccgcaaggt caagcggcgc agcttgcgcc    1680
tctacgcccg ctggcagagc cgctggcgca agaaggtgga ccccagtgct gtgcaaggcc    1740
agggtcccgg gcaccgccag cgccgggcag gcaggcacac agcctcggtg caccacctgg    1800
tctaccacca ccatcaccac caccaccacc actaccattt cagccatggc agcccccgca    1860 ggccggccc cgagccaggc gcctgcgaca ccaggctggt ccgagctggc gcgcccccct    1920
cgccaccttc cccaggccgc ggacccccg acgcagagtc tgtgcacagc atctaccatg    1980
ccgactgcca catagagggg ccgcaggaga gggcccgggt ggcacatgcc gcagccactg    2040
ccgctgccag cctcagactg gccacagggc tgggcaccat gaactacccc acgatcctgc    2100 cctcagggt gggcagcggc aaaggcagca ccagccccgg acccaagggg aagtgggccg    2160
gtggaccgcc aggcaccggg gggcacggcc cgttgagctt gaacagccct gatccctacg    2220
agaagatccc gcatgtggtc ggggagcatg gactgggcca ggcccctggc catctgtcgg    2280
gcctcagtgt gccctgcccc ctgcccagcc ccccagcggg cacactgacc tgtgagctga    2340
```

-continued

```
agagctgccc gtactgcacc cgtgccctgg aggacccgga gggtgagctc agcggctcgg     2400
aaagtggaga ctcagatggc cgtggcgtct atgaattcac gcaggacgtc cggcacggtg     2460
accgctggga ccccacgcga ccaccccgtg cgacggacac accaggccca ggcccaggca     2520
gcccccagcg gcgggcacag cagagggcag ccccgggcga gccaggctgg atgggccgcc     2580
tctgggttac cttcagcggc aagctgcgcc gcatcgtgga cagcaagtac ttcagccgtg     2640
gcatcatgat ggccatcctt gtcaacacgc tgagcatggg cgtggagtac catgagcagc     2700
ccgaggagct gactaatgct ctggagatca gcaacatcgt gttcaccagc atgtttgccc     2760
tggagatgct gctgaagctg ctggcctgcg gccctctggg ctacatccgg aacccgtaca     2820
acatcttcga cggcatcatc gtggtcatca gcgtctggga gatcgtgggg caggcggacg     2880
gtggcttgtc tgtgctgcgc accttccggc tgctgcgtgt gctgaagctg gtgcgctttc     2940
tgccagccct gcggcgccag ctcgtggtgc tggtgaagac catggacaac gtggctacct     3000
tctgcacgct gctcatgctc ttcattttca tcttcagcat cctgggcatg cacctttttcg     3060 gctgcaagtt cagcctgaag acagacaccg agacaccgt gcctgacagg aagaacttcg      3120
actccctgct gtgggccatc gtcaccgtgt tccagatcct gacccaggag gactggaacg     3180
tggtcctgta caacggcatg gcctccacct cctcctgggc cgccctctac ttcgtggccc     3240
tcatgacctt cggcaactat gtgctcttca acctgctggt ggccatcctc gtggagggct     3300
tccaggcgga gggcgatgcc aacagatccg acacggacga ggacaagacg tcggtccact     3360
tcgaggagga cttccacaag ctcagagaac tccagaccac agagctgaag atgtgttccc     3420
tggccgtgac ccccaacggg cacctggagg acgaggcag cctgtcccct ccctcatca      3480 tgtgcacagc tgccacgccc atgcctaccc ccaagagctc accattcctg gatgcagccc     3540
ccagcctccc agactctcgg cgtggcagca gcagctccgg ggacccgcca ctgggagacc     3600
agaagcctcc ggccagcctc cgaagttctc cctgtgcccc ctggggcccc agtggcgcct     3660
ggagcagccg gcgctccagc tggagcagcc tgggccgtgc ccccagcctc aagcgccgcg     3720
gccagtgtgg ggaacgtgag tccctgctgt ctggcgaggg caaggggcagc accgacgacg    3780 aagctgagga cggcagggcc gcgcccgggc cccgtgccac cccactgcgg cgggccgagt     3840
ccctggaccc acggcccctg cggccggccg ccctcccgcc taccaagtgc cgcgatcgcg     3900
acgggcaggt ggtggccctg cccagcgact cttcctgcg catcgacagc caccgtgagg      3960
atgcagccga gcttgacgac gactcggagg acagctgctg cctccgcctg cataaagtgc     4020
tggagcccta caagccccag tggtgccgga gccgcgaggc ctgggccctc tacctcttct     4080
ccccacagaa ccggttccgc gtctcctgcc agaaggtcat cacacacaag atgtttgatc     4140
acgtggtcct cgtcttcatc ttcctcaact gcgtcaccat cgccctggag aggcctgaca     4200
ttgatcccgg cagcaccgag cgggtcttcc tcagcgtctc caattacatc ttcacggcca     4260
tcttcgtggc ggagatgatg gtgaaggtgg tggccctggg gctgctgtcc ggcgagcacg     4320
cctacctgca gagcagctgg aacctgctgg atgggctgct ggtgctggtg tccctggtgg     4380
acattgtcgt ggccatggcc tcggctggtg gcgccaagat cctgggtgtt ctgcgcgtgc     4440
tgcgtctgct gcggaccctg cggcctctga gggtcatcag ccgggccccg ggcctcaagc     4500
tggtggtgga gacgctgata tcatcactca ggcccattgg gaacatcgtc ctcatctgct     4560
gcgccttctt catcatttttt ggcatttttgg gtgtgcagct cttcaaaggg aagttctact     4620
actgcgaggg ccccgacacc aggaacatct ccaccaaggc acagtgccgg gccgcccact     4680
```

-continued

```
accgctgggt gcgacgcaag tacaacttcg acaacctggg ccaggccctg atgtcgctgt   4740
tcgtgctgtc atccaaggat ggatgggtga acatcatgta cgacgggctg gatgccgtgg   4800
gtgtcgacca gcagcctgtg cagaaccaca acccctggat gctgctgtac ttcatctcct   4860
tcctgctcat cgtcagcttc ttcgtgctca acatgttcgt gggcgtcgtg gtcgagaact   4920
tccacaagtg ccggcagcac caggaggcgg aggaggcgcg gcggcgagag gagaagcggc   4980
tgcggcgcct agagaggagg cgcaggagca ctttccccag cccagaggcc cagcgccggc   5040
cctactatgc cgactactcg cccacgcgcc gctccattca ctcgctgtgc accagccact   5100
atctcgacct cttcatcacc ttcatcatct gtgtcaacgt catcaccatg tccatggagc   5160
actataacca acccaagtcg ctggacgagg ccctcaagta ctgcaactac gtcttcacca   5220
tcgtgtttgt cttcgaggct gcactgaagc tggtagcatt tgggttccgt cggttcttca   5280
aggacaggtg gaaccagctg gacctggcca tcgtgctgct gtcactcatg ggcatcacgc   5340
tggaggagat agagatgagc gccgcgctgc ccatcaaccc caccatcatc cgcatcatgc   5400
gcgtgcttcg cattgcccgt gtgctgaagc tgctgaagat ggctacgggc atgcgcgccc   5460
tgctggacac tgtggtgcaa gctctccccc aggtggggaa cctgggcctt cttttcatgc   5520
tcctgttttt tatctatgct gcgctgggag tggagctgtt cgggaggctg gagtgcagtg   5580
aagacaaccc ctgcgagggc ctgagcaggc acgccacctt cagcaacttc ggcatggcct   5640
tcctcacgct gttccgcgtg tccacggggg acaactggaa cgggatcatg aaggacacgc   5700
tgcgcgagtg ctccccgtgag gacaagcact gcctgagcta cctgccggcc ctgtcgcccg   5760
tctacttcgt gaccttcgtg ctggtggccc agttcgtgct ggtgaacgtg gtggtggccg   5820
tgctcatgaa gcacctggag gagagcaaca aggaggcacg ggaggatgcg gagctggacg   5880
ccgagatcga gctggagatg gcgcaggccc ccgggagtgc acgccgggtg gacgcgggaca   5940 ggcctccctt gccccaggag agtccgggcg ccagggacgc cccaaacctg gttgcacgca   6000
aggtgtccgt gtccaggatg ctctcgctgc ccaacgacag ctacatgttc aggcccgtgg   6060
tgcctgcctc ggcgccccac ccccgcccgc tgcaggaggt ggagatggag acctatgggg   6120
ccggcacccc cttgggctcc gttgcctctg tgcactctcc gcccgcagag tcctgtgcct   6180
ccctccagat cccattggct gtgtcgtccc cagccaggag cggcgagccc ctccacgccc   6240
tgtcccctcg gggcacagcc cgctccccca gtctcagccg gctgctctgc agacaggagg   6300
ctgtgcacac cgattccttg gaagggaaga ttgacagccc tagggacacc ctggatcctg   6360
cagagcctgg tgagaaaacc ccggtgaggc cggtgaccca gggggggctcc ctgcagtccc   6420 caccacgctc cccacggccc gccagcgtcc gcactcgtaa gcataccttc ggacagcgct   6480
gcgtctccag ccggccggcg gccccaggcg gagaggaggc cgaggcctcg gacccagccg   6540
acgaggaggt cagccacatc accagctccg cctgcccctg gcagcccaca gccgagcccc   6600
atggccccga agcctctccg gtggccggcg gcgagcggga cctgcgcagg ctctacagcg   6660
tggatgctca gggcttcctg gacaagccgg gccgggcaga cgagcagtgg cggccctcgg   6720
cggagctggg cagcggggag cctggggagg cgaaggcctg gggccctgag gccgagcccg   6780
ctctgggtgc gcgcagaaag aagaagatga gccccccctg catctcggtg gaaccccctg   6840
cggaggacga gggctctgcg cggccctccg cggcagaggg cggcagcacc acactgaggc   6900
gcaggacccc gtcctgtgag gccacgcctc acagggactc cctggagccc acagagggct   6960
caggcgccgg gggggacccct gcagccaagg gggagcgctg gggccaggcc tcctgccggg   7020
ctgagcacct gaccgtcccc agctttgcct ttgagccgct ggacctcggg gtccccagtg   7080
```

-continued

```
gagacccttt cttggacggt agccacagtg tgaccccaga atccagagct tcctcttcag    7140
gggccatagt gcccctggaa cccccagaat cagagcctcc catgcccgtc ggtgacccc     7200 cagagaagag gcgggggctg tacctcacag tcccccagtg tcctctggag aaaccagggt    7260 cccctcagc caccctgcc ccaggggtg gtgcagatga ccccgtgtag ctcggggctt       7320
ggtgccgccc acggctttgg ccctggggtc tgggggcccc gctggggtgg aggcccaggc    7380
agaaccctgc atggaccctg acttgggtcc cgtcgtgagc agaaaggccc ggggaggatg    7440
acggcccagg ccctggttct ctgcccagcg aagcaggagt agctgccggg ccccacgagc    7500
ctccgtccgt tctggttcgg gtttctccga gttttgctac cagccgaggc tgtgcgggca    7560
actgggtcag cctcccgtca ggagagaagc cgcgtctgtg ggacgaagac cgggcacccg    7620
ccagagaggg gaaggtacca ggttgcgtcc tttcaggccc cgcgttgtta caggacactc    7680 gctggggggcc ctgtgcccctt gccggcggca ggttgcagcc accgcggccc aatgtcacct    7740
tcactcacag tctgagttct tgtccgcctg tcacgccctc accacctcc ccttccagcc      7800 accacccttt ccgttccgct cgggccttcc cagaagcgtc ctgtgactct gggagaggtg    7860
acacctcact aaggggccga ccccatggag taacgcgccc ggccccgatg cgaatcaggc    7920
ctcccctaca tctgggggcg ttggccgcga gattcccatt gacacctttg tttcgtgtgc    7980
ttttaaattc aggttaaatg ttgcaataat ctgatgcaga agactcagct tctcaaggga    8040
gagggagggg gcggagcgga ataaatagta acttatttaa gaaatgcaaa aaaaaaa      8097
```

```
<210> SEQ ID NO 6
<211> LENGTH: 4932
<212> TYPE: DNA
<213> ORGANISM: Homo sapiens

<400> SEQUENCE: 6
ctcagggcag gtgcagctgc cacagtgaga cgggcacccc gacccgggca tggaggggggg      60 caagggcccc aggctcagag acttcctgag tgggagtctg gctacctggg cgctgggact      120
ggccgggctg gtcggggagg cggaggactc ggaggggggaa gaagaggaag aggaggaaga     180
gccgcccctt tggttggaga agagattcct gcgcctcagc gatggggccc tgctcctccg      240
ggtgctgggc atcattgccc ccagctcccg agggggacct cggatgctca gaggccttga      300
cggacctgct gcctggcgag tgtggaacct gaaccacctg tggggccgac tgaggggactt     360 ctaccaggag gagctgcagc tgctgatcct gtcgccaccc ccagacctcc agacattggg     420
atttgaccct ctctcagaag aagcggtgga gcagctggaa ggcgttcttc ggctactgtt     480
gggagcgtca gtacagtgtg agcaccggga actcttcatc cgccacatcc agggcctcag     540
tctcgaggtc cagagcgagc tggccgctgc catccaggag gtgacccagc cggggggccgg     600 cgtggtgctg gcactgtctg gccagatcc tggggagctg gcacctgccg agctggagat      660
gctgtcccgg agcctgatgg ggacactgtc gaagctggca cgggagcgtg acctgggggc     720
ccagcggctg gctgaactgc tgctggagcg agaacccctc tgcttgaggc ctgaggctcc     780
ctctagggct cccgccgagg gccctcgca ccatctggcc ctgcagctgg ccaacgccaa       840
ggctcagctg cggcgtctgc ggcaggagct ggaggagaag gccgagctgc tgctagactc     900
ccaggccgag gtgcagggtt tggaggccga aataagaagg ctccgccagg aggcccaggc     960
gctgtcggga caggccaagc gggccgagct gtaccgcgag gaggcagagg cgctgcggga    1020
gcgggccggc cgcctgcccc gcctgcagga ggagctgagg cgctgccgcg agcggctgca    1080
```

-continued

```
ggcggctgag gcctacaaga gtcagctgga ggaggagcgg gtgctctcgg gggtgctgga    1140
ggcgtccaag gcgctgctgg aagagcagct ggaggctgcc cgagagcgct gcgcccggct    1200
gcacgagacc cagcgcgaga acctgctgct gcgaacccgg ctgggcgagg cccatgcgga    1260
gctggactct ctgcggcatc aggtggacca gctggctgag gagaatgtgg agctggagct    1320
ggagcttcag cggagcttgg agccacctcc aggatcccct ggggaggcac ccctagcagg    1380
agcggccccc tcgctgcaag atgaggtgag ggaggcagag gctgggcggc ttcggaccct    1440
tgagagggag aaccgggagc ttcgggggct gcttcaggtg cttcaggggc agccaggggg    1500
ccagcacccc ctgctggagg caccgagaga ggaccctgtt cttccagtgc tggaggaggc    1560
tccccagact cctgtggcct tcgaccacag ccctcagggc ttggttcaga aggcaaggga    1620
tggaggcccc caggccttgg acttggctcc cccggcatta gactcagtgc tcgaggcatc    1680
agctgagtgt ccccaggcac ctgattcaga cccacaggag gcagagagtc cccttcaggc    1740
agctgccatg gaccccccagg cctcagactg gtccccgcaa gagtcaggct ctcctgtgga    1800
gacacaggag tccccggaga aggctggccg tagatcctct ctccagagcc ctgcctctgt    1860
ggccccacct cagggtccag ggaccaaaat tcaggccccg cagttgctgg gaggagagac    1920
agagggaaga gaggctcccc aaggcgagtt ggtgcctgag gcctgggggt tgagacagga    1980
gggccctgag cacaagccag ggccttcgga gcccagctct gtgcagctgg aggagcagga    2040
gggcccaaac cagggcctgg acctggccac gggacaagca gaggccagag agcatgacca    2100
gaggctggaa gggacggtca gggacccagc ctggcaaaaa ccacagcaga agtcagaagg    2160
ggctcttgag gtccaggtct gggaaggccc aatcccaggg gagagcctgg ccagtggtgt    2220
cgcagagcag gaggccctca gggaggaggt ggcacagttg aggagaaagg ctgaggccct    2280
tggagatgag ctggaagccc aggcccgcaa gctggaggcc caaaacacgg aggctgcccg    2340
cctctccaag gagctggccc aagcgcgaag ggcagaggcc gaggcccacc gggaggcaga    2400
ggcccaggcc tgggagcaag cccggctgcg ggaggcagtg gaggctgctg gccaggagct    2460
ggagtctgcg tcccaggaac gggaggcgct ggtggaggcg ctggcagcag cgggccggga    2520
gcggaggcag tgggagcgtg aggggtccag gctgcgggcc cagtcggagg ccgccgagga    2580
acggatgcag gtgctggaga gcgagggccg ccagcacttg gaggaggctg agagggagcg    2640
ccgggagaag gaggccctcc aggcggagct ggagaaagct gtggtgcggg gcaaggagtt    2700
gggggaccgg ctggagcatt tgcagcgtga gctggagcag gcggctctcg agcgccagga    2760
atttctgcga gaaaaggaaa gccagcacca gaggtaccag ggcttggagc agcggctgga    2820
agctgagctg caggcggcgg cgaccagcaa ggaggaggcg ctgatggagc tcaagaccag    2880
ggccctgcag ctggaagagg agctgttcca gctgcgccag ggccccgcgg ggctggggcc    2940
caaaaagcgt gcggagcctc agctggtgga gacccagaat gtgcggctta ttgaggtgga    3000
gcgcagtaat gcgatgctgg tggcagagaa ggcagctttg caggggcagc tgcagcacct    3060
ggaggggcag ctggggagcc tgcagggccg tgcccaggag ctgctgctgc agagccagcg    3120
ggcgcaggag cacagcagcc gcctgcaggc cgagaagtct gtgctggaga ttcagggcca    3180
ggagctgcac cggaagctgg aggtgctgga ggaggaggtg cggcggcac ggcagtccca    3240 ggaggagacc cgcgggcagc agcaggccct gcttcgggac cacaaggccc tggcacagct    3300
gcagcggcgg caggaggccg agctagaggg actgctggtg cggcaccgag acctcaaggc    3360
caacatgcgg gcactggagc tggcccaccg ggagctgcag ggccggcacg agcagctgca    3420
ggcccagcgg gccagcgtgg aggcacagga ggtggccctg ctggcagagc gtgaacgcct    3480
```

```
gatgcaagat gggcatcggc agcggggcct ggaggaggag ctgcggaggc ttcagagcga      3540
gcacgacagg gctcagatgc tgctggcaga gttgtctcgg gagcggggtg agctgcaggg      3600
tgaacgcggg gagctacggg gccggctggc gcggctggag ctggagcggg cacagctgga      3660
gatgcagagc cagcagctgc gcgagtccaa ccagcagctg gacctgagcg cctgccggct      3720
gaccacgcag tgtgagctat tgacacagct gcgaagtgcc caggaagagg agaaccggca      3780
gctgctggct gaagttcagg ccctgagccg ggagaacagg gagctcctgg agcgcagcct      3840
ggagagtcgg gaccacctgc accgcgaaca gcgggagtac ctggaccagc ttaatgccct      3900
gcgccgcgag aagcagaagc tcgtggagaa gatcatggac caataccgcg tgctggagcc      3960
tgtgcccctg ccccggacca agaagggcag ctggctggca gacaaggtga agaggctgat      4020 gcggcccgg cgggaggggg gccccctgg ggggctgcgc ctggggggccg atggggctgg       4080 cagcaccgag agcctggggg gcccccggga gacggagctt cctgagggca gggaggcaga      4140
tgggacaggg tccccttccc cggcacccat gcgccgggcc cagagctccc tctgcctgcg      4200
ggatgagacc ttggcaggcg ggcagcggcg gaaactcagc tcaaggttcc cggtggggcg      4260
aagctctgag tcattcagcc ctggggacac ccctaggcaa cgattccgac agcgccatcc      4320 aggcccctg ggggcgcccg tctcccacag caaaggacct ggtgtgggat gggagaactc       4380
cgctgagacc ctgcaggaac acgaaacaga tgccaaccga gagggccctg aggtacagga      4440
accggagaaa cgtcccctca ccccatccct cagccagtga caccgtggga acagcaggct      4500
tgggagtgca gccttctcgg cactggagtg tcagcggagg ccccaggcag cccaagagct      4560 caggagcca gggaccccaa ggggagtcct ggacaagga ggcctgggcc ctgagatcct        4620
ccacggtcag cgccgggcc cggagatgga gctgggacga gtgtgtggac aggggggatg       4680
gctggccccc acgagcagct ccaggctgga gttctggttc ttccaggtgg ctcccgctga      4740
ggcagcggtc tctgggggat cccccagctg aaggaggctg gcaggagttg gcaagagaac      4800
cccctgccct gtccaggtgg gaagctgagt cccagtgctg ggggactgtg gcctgggctg      4860
atcttgagcc ttaactggac atgaggggca tgagaataaa gctgaactgc agcctcctga      4920
aaaaaaaaaa aa                                                          4932
```

<210> SEQ ID NO 7
<211> LENGTH: 14955
<212> TYPE: DNA
<213> ORGANISM: Homo sapiens

<400> SEQUENCE: 7

```
cttctacatc gcgaatatcc ctcgccggcc tggcgcccgg cgccatctgc tggacccgtt        60
ccggctgggg cgcacagacc tgggcgcggg gtcgggcgat tgggttctcc ctgccttttc       120
aatgtcctgc ggggcggtgg ctcactgtct ctcgccccag cccttccagc tgggtcctga       180
caccaggccc cccgcaccct tcggctcgcc agatgtggct actttccttt agtcccggag       240
ccttcaagcc ctgggtccct gaggggtaga cctgggcggg gtggggccgc gaagcaggga       300 tccaggcgc ctgcgcggag gaggcgggct ccgaggggcc gcacaccggc cactcgcccc        360
tccctgcccg gggttgccat ggggacgcgt gcagacgccg gcccgagagg ctgcgaggg        420 gcaacttctt agagtggccc atcggtcggt ctagggaggg gagggtcagc gtggcaaggt       480
gtgtgtcggg ggcagaggga aggagggaag gagtgctggg gagaagggc agtagtgtcg        540 gggtaggaag ggacagttgt tggggagaag aggcagttgt ggagggagag ggagcaagga      600
```

-continued

```
atatttgtgt gggggagggg gaggagaagg ggcagttgtg acagctgggg gggaagagcc      660
attctgaggg gaaatttgcc tgctggtaac cagtttaagg ataccagctg ctggtataaa      720
tactgctgga taaatactgc tggatttata ctgcaggata aatactgctg gccctgcgg       780 tatttcctag tactagagtg agccccgact tagcagagca gttcctcctg gggcctgcgg      840
tgtgggatcg cgtggtgaac cccacggtgc atgcgcctca ggctctagtt tgaggcagga      900
aagcgcagct tgatgcttct ctggagactg atggaggaag cctccttgct gtagttggtt      960
ttattgattt gctggcctaa cagaacgttt ttccttggag caaagtacaa atccttcaag     1020
tttgaaattc ataacctgag atcaatgcct gtggcagcct gtggggatga ggaaggagag     1080
ccacaggtgc cgttaggctg cagcctaatg aaaagagagt gcccagcgcc tcagactttg     1140
cgcctgggat tctgagcacc tgtccgagat ccccgcttcc tgccatccta cctttctgag     1200
agaggcacca ctgtgacctt cctcgtgccc caattgcttt ttcctcatga cacaatttga     1260
aatttatgat tggatgactt ttgtccttct ttcttccaat ctgttctcag ggcattttga     1320
gtcaaataaa tgatcctgac tgatcttaac cattagcaca gagttcctca gccaactctg     1380
ctaagagacc tcagtacaca caaaacagtg ttcctgcccc tcaggacttc aaagcgatag     1440
acccaggttt tgcctgcacg atgtccagca aagctgagaa gaagcagcga ttgagtggcc     1500
gaggaagctc ccaggcaagc tggtcagggc gggccactcg ggctgctgtg gccacacagg     1560
agcaggggaa tgccccggct gtcagtgagc cagagctgca ggctgagctc cccaaggagg     1620
agcctgagcc acggttggag ggacctcaag cacagagtga agaatcagtg gagcccgagg     1680
cagatgtgaa gcccctcttc ctttcccgag ctgcgctgac aggactggcg gatgcagtgt     1740
ggacacagga gcatgatgcc attctggaac actttgccca ggaccctaca gaatccatcc     1800
tcaccatctt cattgaccct tgttttgggc tgaagctaga gctgggcatg cctgtacaga     1860
cccagaacca gcttgtctac ttcattcgcc aagcaccagt tcccatcacc tgggagaact     1920
tcgaggcaac tgtgcagttt gggacggtgc ggggcccta tatcccggcc ctgcttcggc      1980
tgctcggtgg agtctttgcc cctcagatct ttgcaaacac aggctggcct gagagcatta     2040
gaaatcattt tgcttctcat ctgcacaagt tcttggcctg cctgacagac actcggtaca     2100
aactggaggg gcacacggtc ctctacatcc ctgcagaggc catgaacatg aagcctgaga     2160
tggtgataaa ggacaaagag ctggtgcaac ggctagagac ctccatgatc cactggaccc     2220
ggcagataaa ggagatgctc agtgcccagg agactgtgga gacaggagaa aatttaggtc     2280
ctctggagga gattgagttc tggcgcaacc gatgcatgga cctgtctggc atcagtaagc     2340
agctggtgaa gaagggagtg aagcacgttg aatccatcct gcaccttgcc aagtcgtcct     2400
acttggcgcc ctttatgaaa ctggcacagc agatccagga tggctctcgt caagcacagt     2460
caaacctgac cttttttgtca atcctgaagg aaccttacca ggagttggct ttcatgaagc     2520
ccaaggacat ctctagcaag ctccctaagc tgatcagtct catccgcatc atctgggtca     2580
actctcccca ctacaacact cgggagagac tgacctcgct cttccgaaag gtatgtgact     2640
gtcagtatca cttcgcccgc tgggaagatg gcaagcaggg tcccctcct tgcttcttg      2700 gtgcccaggg gccacagata acacggaact tgctggagat tgaggacatc tttcataaaa     2760
atctgcacac gctgcgagcc gttcgcgggg gtatcctgga tgtcaagaac acctgttggc     2820
atgaagacta caataagttc cgtgccggaa tcaaggacct ggaggtgatg acccagaacc     2880 tgatcaccctc agccttcgag ttggtgcggg acgtgccgca cggcgtgctt ctgctggaca     2940
ccttccacag gcttgcctcc cgcgaggcta tcaagcggac ttatgacaag aaggcggtgg     3000
```

```
atctctacat gctgttcaat agcgagctgg ccctggtgaa ccgtgaacgg aacaagaaat    3060
ggccagacct ggagccctac gtggcccagt attccggaaa ggcgcgctgg gtgcacatcc    3120
tccggcgtcg catcgacaga gtcatgacct gccttgctgg tgctcatttc ctgccccgta    3180
ttgggactgg aaaggagagt gtgcacacct atcagcagat ggtccaggcc attgatgagc    3240
tggttcgaaa aaccttccaa gagtggacat caagtctgga caaggattgc attcggcggt    3300
tggatacccc attgctgcga atcagccagg agaaggcggg catgctggat gtcaactttg    3360
acaagtccct tctgattctc tttgcggaaa ttgactactg ggagcggctg ctgtttgaga    3420
cgccccatta cgtggtgaac gtagctgagc gagccgagga cctgcgcatt ctgcgtgaaa    3480
atctgctact cgttgctaga gactacaata ggattattgc catgctgtcc ccagatgagc    3540
aggccctatt caaagagcgt attcggctcc tggataagaa gatccacccg ggactcaaga    3600
aactgcactg ggccttgaag ggggccagtg ccttcttcat cacggagtgc cgtatacatg    3660
ccagcaaggt gcagatgatt gtgaatgagt tcaaggcatc cactctgacc attggctggc    3720
gagcccaaga gatgtcagag aagctgctgg tacgcattag tggcaaacgg gtatacaggg    3780
acctggaatt tgaagaggac caaagagagc atcgggcagc tgtacagcag aaattgatga    3840
acctgcacca ggatgtggtg accatcatga ccaactccta tgaggtcttc aagaatgatg    3900
gtcctgagat tcagcagcag tggatgctgt acatgattcg gctggaccgc atgatggagg    3960
atgccctgcg cctgaatgtg aagtggtcac tgctagaact atccaaggct atcaacgggg    4020
atggaaagac cagcccaaac ccactcttcc aagtccttgt cattttgaag aatgatctgc    4080
aaggaagtgt ggcacaggtg gaattctcac ccactctgca gactttggca ggtgtggtca    4140
atgacattgg caaccacctc ttttccacca tctctgtctt ctgccacctc cctgacattc    4200
tcaccaagcg caagttacat cgtgaaccca tccaaacagt tgtggagcaa gatgaggaca    4260
tcaagaagat ccagacccaa atcagcagcg gcatgactaa caacgcaagc ctgctgcaga    4320
actacctcaa gacctgggac atgtaccggg agatctggga gatcaacaag gactccttca    4380
ttcatcgcta ccagcgcctc aaccctcctg tctcttcttt tgttgccgac attgcccgct    4440
acacggaagt tgctaataac gtgcagaagg aggagacagt caccaacatc cagtttgtgc    4500
tgctggactg ttcgcacctc aagttctccc tggtgcagca ctgcaatgaa tggcagaaca    4560
agttcgcgac tctgctcagg gagatggctg ctgggcgcct cctggagctg cacacctacc    4620
tgaaggagaa cgcagagaaa atcagccgcc ctccgcagac actggaggaa ctgggggtca    4680
gcttgcagct cgtggatgcc ctgaagcacg acttggccaa cgtggagact cagatccctc    4740
ccatacacga gcaatttgcc attcttgaaa gtacgaggt gccagtcgag gacagtgtcc     4800
tggagatgct ggacagtctc aacggggagt gggttgtctt ccaacaaact ctgctggaca    4860
gtaagcaaat gctgaagaaa cacaaggaga aattcaagac aggcctgatc cactcggcag    4920
atgacttcaa gaagaaagca catacacttc tggaagattt cgaattcaaa ggccatttca    4980
ccagcaacgt gggatacatg tctgccttag accagattac acaagtgcgg gccatgctga    5040
tggccatgcg ggaagaggaa aatagtctcc gagccaacct gggcatcttc aagatcgagc    5100
agccaccctc caaggacctt cagaacctgg agaaggagct cgatgccctc agcaaatct     5160 gggagatcgc acgagactgg gaggagaact ggaatgagtg gaagactggc cggttcctga    5220
tcctgcagac ggaaaccatg gagaccacg cccacgggct gtttcgtcgc ctcacaaaat     5280
tagccaaaga gtataaggac cgaaactggg aaattattga aaccactcgc tcaaaaatag    5340
```

-continued

```
agcagttcaa gaggaccatg cctctcatct cagacctgcg gaaccctgcc cttagagaga    5400
ggcactggga ccaggtccgg gatgagatcc agcgggagtt tgatcaggaa tctgaaagct    5460
tcaccttgga gcagattgtg gagcttggga tggatcagca tgtggagaaa attggggaga    5520
tctctgcttc agcaactaaa gagctggcta tagaagtggc tttacaaaac attgccaaga    5580
cctgggatgt gactcagctc gacatagtac cctacaagga taagggccat catcggctca    5640
gaggtacaga agaagtattc caggcactgg aagataacca ggtagctctg tctaccatga    5700
aggcatcacg ctttgtcaag gcctttgaga aggatgtgga ccactgggaa cgctgcctct    5760
ccctcatttt ggaggttatt gagatgattc tcacagtgca gcgtcagtgg atgtacttag    5820
agaatatctt cctaggagaa gacatccgca agcagctgcc caatgaatcg accttatttg    5880
accaggtcaa cagcaactgg aaagccatca tggacaggat gaacaaggac aacaatgctc    5940
tccggagcac ccatcaccca ggcctcctgg acacattgat agaaatgaat acaatcctgg    6000
aagatattca gaaatctctg gatatgtatt tagagaccaa gcgacatatt ttccccccgct    6060 tctacttctt gtccaatgat gacctgctgg agattctggg ccagtcccga aacccagagg    6120
ctgtgcagcc acacctcaaa aaatgctttg acaacatcaa gttgctgaga atccagaagg    6180
ttggagggcc cagcagcaaa tgggaagctg tggggatgtt ctcgggcgac ggcgagtaca    6240
ttgacttcct ccactcagta ttttttagaag gccctgtgga gtcctggctt ggcgatgtgg    6300
aacagaccat gagggtgacc ctgcgggacc ttctccggaa ctgccacctg gccctcagga    6360
agttcctcaa caagagggac aaatgggtga aggagtgggc tggccaggtg gtgatcactg    6420
ccagtcagat ccagtggacg gctgatgtca ccaagtgcct gctgacagcg aaggagcggg    6480
cagacaagaa aatcctcaag gtcatgaaga agaaccaggt gtcaatcctg aataagtatt    6540
cagaagccat caggggggaac ttgaccaaga tcatgcggct taaaattgtg gctctggtga    6600
cgatagaaat tcatgcccgg gatgtgttgg agaagcttta caagagtggc ctcatggatg    6660
tcaattcctt tgactggctc agccaacttc ggttctactg ggagaaggat cttgatgact    6720
gtgtcatccg ccagaccaac acgcaatttc agtataatta tgagtacttg ggtaactcgg    6780
gccggctcgt catcaccccc ctgacggaca ggtgttacat gacactgacc acggcattgc    6840
acctgcaccg agggggctcc cccaaaggcc ctgcaggcac aggcaagacc gagaccgtca    6900
aggacctggg caaggccctg ggcatatatg tcattgtggt caactgctct gagggcctgg    6960
actacaagtc catgggccga atgtactcag gtctggccca gactggagct tggggctgct    7020
ttgatgagtt taaccgcatc aacatcgagg tgctgtcagt ggtggcccac cagatcctgt    7080
gcatcctgtc tgccctggct gccggcctca cccatttcca ttttgatggc tttgaaataa    7140
atctggtgtg gtcctgtggg atcttcatta ccatgaatcc tggctatgct ggccgcacag    7200
agcttcccga aaatcttaaa tccatgttcc gcccaattgc catggtggtg cctgactcca    7260
ccctcattgc agaaatcatt ctctttggag agggctttgg caactgcaag attctggcca    7320
agaaggtgta cacactctac tcactggctg tgcagcagct gtccagacag gaccactatg    7380
actttggcct gcgtgccctc acctcccttc tgcgctatgc tggcaagaag cgccgcctac    7440
agccggatct gactgatgaa gaggttctgc tgctctcaat gagagatatg aacatcgcca    7500
agctcacttc agttgatgca cccctgttca atgccatcgt gcaagatctg tttcccaaca    7560
ttgagctgcc tgtcattgac tatggcaagc tgcgggagac cgttgagcag agagattcgag    7620 acatgggcct gcaaagcacg ccgttcaccc tcaccaaggt tttccagttg tatgaaacca    7680
agaactcccg ccactccacc atgatcgtgg gctgcacggg cagcggcaag actgcctcat    7740
```

```
ggcgcattct acaggcctcc ctgtcctctc tgtgccgcgc cggagaccct aacttcaaca   7800
ttgttagaga gttccctttg aaccccaagg cattgtccct aggggaactg tatggggaat   7860
atgacctcag caccaatgaa tggacagatg gcatcttgtc cagtgtcatg cggacggcat   7920
gtgcagatga gaaacccgac gagaagtgga tcctgttcga tggccccgtg gacacactgt   7980
ggatcgagaa catgaactcc gtcatggacg ataacaaggt gttgaccctc atcaacggcg   8040
agcgcatcgc gatgcccgag caggtgtctc tcctgtttga agtggaggac ctggcaatgg   8100
cctctccggc cactgtatcc cgctgcggga tggtctacac tgactacgct gacctgggct   8160
ggaagcccta tgttcagtca tggctggaga agaggccaaa ggctgaggtg gagcccttc    8220 aacgcatgtt cgaaaagctc atcaacaaga tgctggcctt taagaaggac aactgcaagg   8280
agctggtgcc cctgcccgag tacagcggta tcacctccct ctgcaagctg tactctgccc   8340
tggccacgcc agagaatggg gtgaacccag ctgacggcga gaactatgtc accatggtag   8400
agatgacatt tgtgttcagc atgatctggt ctgtgtgtgc ctctgtggat gaggagggcc   8460
ggaagaggat cgacagctac ctccgagaga tcgagggctc ctttcccaat aaggacacgg   8520
tatatgagta ttttgtggac cccaaaatac ggagttggac atcatttgag gacaagctcc   8580
ctaagagttg gcgctaccct ccaaacgccc ccttctataa gatcatggtg cccaccgtcg   8640
acactgttcg ctacaactac ctggtgagca gcttggtggc caaccagaat cccattctgc   8700
tggtgggtcc cgtggggact gggaagacct ccatcgccca gagcgttctg cagtccctgc   8760
cctccagcca gtggtcggtg ctcgttgtca acatgtccgc acagaccaca tccaataacg   8820
tgcagagcat cattgagagc agggttgaga agcgaaccaa gggtgtctac gtgccattcg   8880
ggggcaaaag catgatcacc tttatggatg acctaaatat gcccgctaag gacatgtttg   8940
ggtcccagcc acccctggag ctgatccgcc tctggattga ctatggcttc tggtatgacc   9000
gtacgaagca gaccatcaag tacattcgag aaatgttcct gatggctgcc atgggccccc   9060 ctggggggtgg acggactgtc atctccccaa ggctacggag tcgcttcaac attatcaaca   9120
tgaccttccc cacaaagtcc cagatcatcc gcatattcgg caccatgatc aatcagaagc   9180
ttcaggactt tgaggaagag gtgaagccca ttgggaacgt ggtgacagag gccaccctgg   9240
acatgtacaa caccgtggta cagcgcttcc tgcccacgcc caccaagatg cattacctct   9300
tcaaccttcg agacatctcc aaggtgttcc agggcatgct tagagccaac aaggacttcc   9360
atgataccaa gtccagcatc acacggctct ggatccatga atgtttcaga gtcttctctg   9420
accggctggt tgatgcggca gacacagaag ccttcatggg catcataagc gacaagctcg   9480
gctccttctt tgacctcaca tttcatcatc tctgtcccag caagcgtcct cctatctttg   9540
gggatttcct gaaggagccc aaggtgtatg aagacctcac ggatctgaca gtgctgaaga   9600
cagtcatgga gacagctcta aatgagtata acctgtcacc ctctgtcgtg cccatgcagc   9660
tagtgctctt ccgagaggct attgaacaca tcacacggat cgtgcgggtc attggacagc   9720
ctcggggcaa catgctcctg gtgggtatcg ggggcagcgg acgccagagt ctggcccgcc   9780
tggcttcatc catctgcgac tacaccacct tccagatcga ggtcaccaaa cattatcgga   9840
agcaggagtt ccgagatgat atcaagcgtc tgtatcgcca ggctggggtg gagctcaaga   9900
ccacgtcctt cattttttgtg gacacccaaa tagctgatga gtccttccta gaggacatca   9960
acaacatcct cagctcaggc gaggtgcccca atctctacaa gcctgatgaa tttgaagaga   10020
tccagtcgca tatcatagac caggcccggg tggagcaggt gcctgagtca tcggacagcc   10080
```

-continued

```
tcttcgccta cctcattgaa cgcgtgcaga acaacctgca catcgtgctc tgcctcagcc   10140
ccatggggga tcccttcagg aactggatcc gccagtaccc agccttggtg aactgcacaa   10200
ccatcaactg gttctcagag tggccccaag aggccctgct cgaggtggct gagaagtgcc   10260
tcataggagt agacctggga actcaggaga atatccacag gaaggtggcc cagatctttg   10320
tcactatgca ctggtcagta gctcagtatt cccagaagat gctgttggaa ctgcggagac   10380
acaactatgt cacacccacc aaatacctgg aactcctgtc tggatataag aagttgctgg   10440
gagaaaaacg gcaggagctg ctggcccaag ccaataaact gcggacaggc ttgttcaaga   10500
tcgacgaaac tagggaaaag gtgcaagtga tgtcgttgga gctggaggat gccaagaaga   10560
aggtggctga gttccagaag cagtgtgagg agtacctggt catcattgtg cagcagaagc   10620
gggaggcaga tgagcagcag aaggccgtaa cagccaacag tgaaaagatt gcagttgagg   10680
aaatcaagtg tcaggcactg gctgacaatg cccagaaaga tctagaagag gcactgcccg   10740
ccctggaaga ggccatgcgg gccctggagt ctctgaacaa gaaggatata ggagagatca   10800
agtcttatgg acggcccca gcccaagtgg agatagtgat gcaggcagtt atgattcttc   10860
gaggcaacga gcccacatgg gcagaggcca agaggcagct aggggaacag aacttcatca   10920
agtcactgat caactttgat aaagacaata tctcagataa ggttctgaag aagattgggg   10980
cctactgcgc ccagcctgac ttccagcctg atatcatcgg ccgcgtctcc ctggctgcca   11040
agtccctctg catgtgggtg cgggccatgg agctgtatgg gcggctatat cgggtggtgg   11100
agcccaagcg aatccgaatg aacgctgcct tggctcagct tcgggagaag caagccgcgc   11160
tcgctgaggc ccaggagaag ctgcgggagg tagctgagaa actggagatg ctaaagaaac   11220
agtatgatga gaagctggca cagaaggagg agcttcgcaa gaagtctgaa gagatggagc   11280
tgaagctgga gcgagctggg atgctcgtgt cggggttggc tggcgagaag gccagatggg   11340
aggagacagt ccagggcctg gaggaggacc tgggctacct ggtgggggac tgtctcctgg   11400
cagctgcctt cctgtcctac atgggaccct tcctgaccaa ctaccgggat gagattgtca   11460
accaaatctg gatcgggaag atctgggagc ttcaggttcc ttgctcccct tctttcgcca   11520
tcgataactt cctgtgcaat cctaccaaag tccgggactg gaacatccaa gggttgccct   11580
cagacgcctt ctccactgag aatggcatca tcgtcacccg aggcaacagg tgggcactga   11640
tgatcgaccc tcaggcccag gccctgaaat ggattaagaa catggaagga ggccagggcc   11700
tgaagatcat cgacctgcag atgagcgatt acctgcgaat cctagaacac gccattcact   11760
ttggataccc ggtgctactt cagaacgtgc aggaatatct ggaccccaca ctgaacccca   11820
tgctcaacaa atctgtagcc cgaatcggtg tcggctgtt gatgcgcatt ggcgataagg   11880
aggtggaata taataccaat ttccgtttct acatcaccac caagctctcc aaccccact   11940 acagcccaga gacctcagcc aagaccacca tcgtcaactt tgctgttaaa gaacagggcc   12000
tggaggccca gctgctgggc attgtggtgc ggaaggagcg gcctgagctg gaggagcaga   12060
aggactcact ggtcatcaac atcgcggctg gtaaaaggaa gctcaaggag ctggaggatg   12120
agatcctgcg gctgctgaat gaggccaccg gctccctgct ggatgatgtg cagctggtga   12180
acacgctgca tacctccaag atcacagcca cagaggtgac tgagcagctg gagaccagtg   12240
agaccacaga gatcaacact gacttggcgc gggaggctta ccgcccatgc gcccagcggg   12300
catcaatcct gttcttcgtg ctcaatgata tgggctgcat cgaccccatg taccagttct   12360
cactggatgc ctacatcagc ctctttattc tcagcattga caaaagccac cgcagcaata   12420
agctggagga ccgcattgac tacctgaatg actaccacac ctacgctgtc tacaggtaca   12480
```

-continued

```
cctgccgtac ccttttcgaa cgccacaaac tactattcag ttttcatatg tgtgccaaaa   12540
tcttggagac ttctggcaag ctcaacatgg atgaatacaa cttctttcta cgtgggggtg   12600
tggtcttgga tcgggagggc caaatggaca atccatgtag tagctggctt gcagatgcct   12660
actgggataa catcacagag ctagacaaac tgaccaactt ccacggactc atgaactcct   12720
ttgagcagta ccctcgtgac tggcacctgt ggtataccaa tgctgccccg gagaaggcga   12780
tgctgccagg tgagtgggaa aatgcctgca atgaaatgca acggatgctg atcgttcgct   12840
ccctgcgcca ggaccgcgtg gccttctgcg tgacctcctt catcatcacc aaccttggct   12900
cccgcttcat cgagccgcct gtgctgaata tgaagtcggt gctggaggat tcaaccccac   12960
gatccccact cgtgttcatc ctgtccctg gtgtggaccc caccagtgcc ctgctgcagc   13020
tggcagagca catgggcatg gcccagcgct ccacgccct gtccctgggc cagggccagg   13080
cccccatcgc tgctcggctc ctccgagagg gtgtgactca gggacactgg gtgttcctgg   13140
caaactgcca cctgtcactg tcttggatgc ctaatctgga caagctggtg gagcagctgc   13200
aggtggagga tcctcatcca tccttccgcc tctggctcag ctccatcccc cacccagact   13260
tccctatctc aatcttgcag gtcagcatca agatgaccac agagccacca aagggcctaa   13320
aggccaacat gacacgtctt taccaactga tgtcagaacc acagttttcc cgctgctcca   13380
aacctgccaa atataagaag ctgctgtttt cactctgttt cttccactct gtgttacttg   13440
aacgcaaaaa gttcctgcag cttggctgga acatcatcta tggcttcaat gactccgact   13500
ttgaggtgtc agaaaacttg ctgagcctct atctcgatga gtacgaggag acaccttggg   13560
acgcacttaa gtacctcatt gccggcatca actatggtgg acatgtcaca gatgactggg   13620
accggcgcct gctgaccacc tacatcaatg attatttctg tgaccagtct ctatcaactc   13680
ccttccaccg gttgtcagca ctggagactt atttcatccc caaggatggc agcctcgctt   13740
cttacaagga atacatcagc ttattgcctg gcatggaccc ccctgaggcc tttggccagc   13800
accccaatgc tgatgtggcc tctcagatca ctgaggcaca aaccctcttt gatactttgc   13860
tttccttgca acctcagatt acacccacca gggctggagg ccagacccgg gaagagaagg   13920
tccttgagtt ggccgctgat gtgaagcaga agatccctga aatgatcgac tatgagggga   13980
ctcaaaaact gctagctctc gacccctccc ccctcaatgt ggtccttctg caggagatcc   14040
agagatacaa cacactgatg cagaccatcc tgttctcact gacagaccta gagaaaggca   14100
tccagggtct catcgtcatg tctacaagcc tggaagagat tttcaattgc atctttgatg   14160
cccatgttcc tccgctctgg ggaaaggcat acccctcaca aaagccattg gctgcctgga   14220
cccgggactt ggccatgcgt gtggagcagt ttgagctgtg ggccagccgg gcccggcctc   14280
ctgtgatctt ctggttgtct ggtttcacct ttcccactgg cttcctcact gctgtgctgc   14340
agtcttcagc tcgccaaaac aacgtttcag tggacagcct ctcctgggag tttatcgttt   14400
ccactgtgga tgacagcaac ctagtgtatc cccccaagga tggtgtctgg tccggggcc   14460 tgtacctgga aggtgctggc tgggaccgga agaactcctg cttggtggag gcagagccca   14520
tgcagcttgt ctgcctcatg cccacgatcc acttccggcc tgcagagagc cgcaagaaga   14580
gcgccaaggg catgtactcc tgccctgct attactatcc caaccgggca ggcagctcag   14640
accgagcctc ctttgtcatc ggcattgacc tgcggtctgg ggccatgaca cctgatcatt   14700
ggatcaagag gggcactgct ctactcatga gcctggacag ctgagaccte ctcctcttct   14760 ccgcttgaga gagagggtca gggactccag gagctaagac agatgttgca cctaggactg   14820
```

-continued

```
aggccggacc tcactcagac tttgaccttg gccgaatttg tgtgatgtgg ccctggagat   14880
acctagttgt gttagccata aaagtgaaag agttgtattg gagctcagtg ctgtaaaaca   14940
cccgcgacaa caagc                                                    14955

<210> SEQ ID NO 8
<211> LENGTH: 13480
<212> TYPE: DNA
<213> ORGANISM: Homo sapiens

<400> SEQUENCE: 8
ttattttttc aaatggtgta gccgccggag gtgcggtgct cagttcttgg aagggggcccg     60 gatgtactga ggatgcgtta cagtttcact cgaggaggca gtagtggaaa ggagcagttt    120
ttggggtttg atgccataat gggaatcagg taatcgtcgg cggggaagaa gaaacgctgc    180
agaccacggc ttcctcgaat cttgcgcgaa agccgccggc ctcggaggag ggattaatcc    240
agacccgccg gggggtgttt tcacatttct tcctcttcgt ggctgctcct cctattaaaa    300 ccattttttgg tccatggtca atgagaatac gaggatgtac attccagagg aaaaccacca    360
aggttccaac tatgggagcc cacgccccgc ccatgccaac atgaatgcca atgcggcagc    420
ggggctggcc cctgagcaca tccccacccc gggggctgcc ctgtcgtggc aggcggccat    480
cgacgcagcc cggcaggcta agctgatggg cagcgctggc aatgcgacca tctccacagt    540
cagctccacg cagcggaagc ggcagcaata tgggaaaccc aagaagcagg gcagcaccac    600
ggccacacgc ccgccccgag ccctgctctg cctgaccctg aagaacccca tccggagggc    660
ctgcatcagc attgtcgaat ggaaaccatt tgaaataatt attttactga ctatttttgc    720
caattgtgtg gccttagcga tctatattcc cttcccagaa gatgattcca acgccaccaa    780
ttccaacctg gaacgagtgg aatatctctt tctcataatt tttacggtgg aagcgttttt    840
aaaagtaatc gcctatggac tcctctttca ccccaatgcc tacctccgca acggctggaa    900
cctactagat tttataattg tggttgtggg gcttttttagt gcaattttag aacaagcaac    960
caaagcagat ggggcaaacg ctctcggagg gaaaggggcc ggatttgatg tgaaggcgct   1020
gagggccttc cgcgtgctgc gccccctgcg gctggtgtcc ggagtcccaa gtctccaggt   1080
ggtcctgaat tccatcatca aggccatggt cccccctgctg cacatcgccc tgcttgtgct   1140
gtttgtcatc atcatctacg ccatcatcgg cttggagctc ttcatgggga agatgcacaa   1200
gacctgctac aaccaggagg gcatagcaga tgttccagca gaagatgacc cttcccttg    1260 tgcgctggaa acgggccacg ggcggcagtg ccagaacggc acggtgtgca gcccggctg    1320 ggatggtccc aagcacggca tcaccaactt tgacaacttt gccttcgcca tgctcacggt   1380
gttccagtgc atcaccatgg agggctggac ggacgtgctg tactgggtca atgatgccgt   1440
aggaagggac tggcccctgga tctatttttgt tacactaatc atcatagggt cattttttgt   1500
acttaacttg gttctcggtg tgcttagcgg agagttttcc aaagagaggg agaaggccaa   1560
ggcccgggga gatttccaga agctgcggga gaagcagcag ctagaagagg atctcaaagg   1620
ctacctggat tggatcactc aggccgaaga catcgatcct gagaatgagg acgaaggcat   1680
ggatgaggag aagccccgaa acatgagcat gcccaccagt gagaccgagt ccgtcaacac   1740
cgaaaacgtg gctggaggtg acatcgaggg agaaaactgc ggggccaggc tggcccaccg   1800
gatctccaag tcaaagttca gccgctactg cgccggtgg aatcggttct gcagaaggaa   1860
gtgccgcgcc gcagtcaagt ctaatgtctt ctactggctg gtgattttcc tggtgttcct   1920
caacacgctc accattgcct ctgagcacta caaccagccc aactggctca cagaagtcca   1980
```

-continued

```
agacacggca aacaaggccc tgctggccct gttcacggca gagatgctcc tgaagatgta   2040
cagcctgggc ctgcaggcct acttcgtgtc cctcttcaac cgctttgact gcttcgtcgt   2100
gtgtggcggc atcctggaga ccatcctggt ggagaccaag atcatgtccc cactgggcat   2160
ctccgtgctc agatgcgtcc ggctgctgag gattttcaag atcacgaggt actggaactc   2220
cttgagcaac ctggtggcat ccttgctgaa ctctgtgcgc tccatcgcct ccctgctcct   2280
tctcctcttc ctcttcatca tcatcttctc cctcctgggg atgcagctct ttggaggaaa   2340
gttcaacttt gatgagatgc agacccggag gagcacattc gataacttcc cccagtccct   2400
cctcactgtg tttcagatcc tgaccgggga ggactggaat tcggtgatgt atgatgggat   2460
catggcttat ggcggcccct cttttccagg gatgttagtc tgtatttact tcatcatcct   2520
cttcatctgt ggaaactata tcctactgaa tgtgttcttg gccattgctg tggacaacct   2580
ggctgatgct gagagcctca catctgccca aaaggaggag gaagaggaga aggagagaaa   2640
gaagctggcc aggactgcca gcccagagaa gaaacaagag ttggtggaga gccggcagt   2700 gggggaatcc aaggaggaga agattgagct gaaatccatc acggctgacg gagagtctcc   2760
acccgccacc aagatcaaca tggatgacct ccagcccaat gaaaatgagg ataagagccc   2820
ctaccccaac ccagaaacta caggagaaga ggatgaggag gagccagaga tgcctgtcgg   2880
ccctcgccca cgaccactct ctgagcttca ccttaaggaa aaggcagtgc ccatgccaga   2940
agccagcgcg tttttcatct tcagctctaa caacaggttt cgcctccagt gccaccgcat   3000
tgtcaatgac acgatcttca ccaacctgat cctcttcttc attctgctca gcagcatttc   3060
cctggctgct gaggacccgg tccagcacac ctccttcagg aaccatattc tgttttattt   3120
tgatattgtt tttaccacca ttttcaccat tgaaattgct ctgaagatga ctgcttatgg   3180
ggctttcttg cacaagggt ctttctgccg gaactacttc aacatcctgg acctgctggt   3240
ggtcagcgtg tccctcatct cctttggcat ccagtccagt gcaatcaatg tcgtgaagat   3300
cttgcgagtc ctgcgagtac tcaggcccct gagggccatc aacagggcca aggggctaaa   3360
gcatgtggtt cagtgtgtgt ttgtcgccat ccggaccatc gggaacatcg tgattgtcac   3420
caccctgctg cagttcatgt ttgcctgcat cggggtccag ctcttcaagg gaaagctgta   3480
cacctgttca gacagttcca agcagacaga ggcggaatgc aagggcaact acatcacgta   3540
caaagacggg gaggttgacc accccatcat ccaaccccgc agctgggaga acagcaagtt   3600
tgactttgac aatgttctgg cagccatgat ggccctcttc accgtctcca ccttcgaagg   3660
gtggccagag ctgctgtacc gctccatcga ctcccacacg gaagacaagg gccccatcta   3720
caactaccgt gtggagatct ccatcttctt catcatctac atcatcatca tcgccttctt   3780
catgatgaac atcttcgtgg gcttcgtcat cgtcaccttt caggagcagg gggagcagga   3840
gtacaagaac tgtgagctgg acaagaacca gcgacagtgc gtggaatacg ccctcaaggc   3900
ccggcccctg cggaggtaca tccccaagaa ccagcaccag tacaaagtgt ggtacgtggt   3960
caactccacc tacttcgagt acctgatgtt cgtcctcatc ctgctcaaca ccatctgcct   4020
ggccatgcag cactacggcc agagctgcct gttcaaaatc gccatgaaca tcctcaacat   4080
gctcttcact ggcctcttca ccgtggagat gatcctgaag ctcattgcct tcaaacccaa   4140
gcactatttc tgtgatgcat ggaatacatt tgacgccttg attgttgtgg gtagcattgt   4200
tgatatagca atcaccgagg taaacccagc tgaacatacc caatgctctc cctctatgaa   4260
cgcagaggaa aactcccgca tctccatcac cttcttccgc ctgttccggg tcatgcgtct   4320
```

-continued

```
ggtgaagctg ctgagccgtg gggagggcat ccggacgctg ctgtggacct tcatcaagtc      4380
cttccaggcc ctgccctatg tggccctcct gatcgtgatg ctgttcttca tctacgcggt      4440
gatcgggatg caggtgtttg ggaaaattgc cctgaatgat accacagaga tcaaccggaa      4500
caacaacttt cagaccttcc cccaggccgt gctgctcctc ttcaggtgtg ccaccgggga      4560
ggcctggcag gacatcatgc tggcctgcat gccaggcaag aagtgtgccc cagagtccga      4620
gcccagcaac agcacggagg gtgaaacacc ctgtggtagc agctttgctg tcttctactt      4680
catcagcttc tacatgctct gtgccttcct gatcatcaac ctctttgtag ctgtcatcat      4740
ggacaacttt gactacctga caagggactg gtccatcctt ggtccccacc acctggatga      4800
gtttaaaaga atctgggcag agtatgaccc tgaagccaag ggtcgtatca aacacctgga      4860
tgtggtgacc ctcctccggc ggattcagcc gccactaggt tttgggaagc tgtgccctca      4920
ccgcgtggct tgcaaacgcc tggtctccat gaacatgcct ctgaacagcg acgggacagt      4980
catgttcaat gccaccctgt ttgccctggt caggacggcc ctgaggatca aaacagaagg      5040
gaacctagaa caagccaatg aggagctgcg ggcgatcatc aagaagatct ggaagcggac      5100
cagcatgaag ctgctggacc aggtggtgcc ccctgcaggt gatgatgagg tcaccgttgg      5160
caagttctac gccacgttcc tgatccagga gtacttccgg aagttcaaga agcgcaaaga      5220
gcagggcctt gtgggcaagc cctcccagag gaacgcgctg tctctgcagg ctggcttgcg      5280
cacactgcat gacatcgggc ctgagatccg acgggccatc tctggagatc tcaccgctga      5340
ggaggagctg gacaaggcca tgaaggaggc tgtgtccgct gcttctgaag atgacatctt      5400
caggagggcc ggtggcctgt tcggcaacca cgtcagctac taccaaagcg acggccggag      5460
cgccttcccc cagaccttca ccactcagcg cccgctgcac atcaacaagg cgggcagcag      5520
ccagggcgac actgagtcgc catcccacga gaagctggtg gactccacct tcacccccag      5580
cagctactcg tccaccggct ccaacgccaa catcaacaac gccaacaaca ccgccctggg      5640
tcgcctccct cgccccgccg gctacccag cacggtcagc actgtggagg gccacgggcc      5700 cccctttgtcc cctgccatcc gggtgcagga ggtggcgtgg aagctcagct ccaacaggtg      5760
ccactcccgg gagagccagg cagccatggc gggtcaggag gagacgtctc aggatgagac      5820
ctatgaagtg aagatgaacc atgacacgga ggcctgcagt gagcccagcc tgctctccac      5880
agagatgctc tcctaccagg atgacgaaaa tcggcaactg acgctcccag aggaggacaa      5940
gagggacatc cggcaatctc cgaagagggg tttcctccgc tctgcctcac taggtcgaag      6000
ggcctccttc cacctggaat gtctgaagcg acagaaggac cgaggggggag acatctctca      6060 gaagacagtc ctgcccttgc atctggttca tcatcaggca ttggcagtgg caggcctgag      6120
ccccctcctc cagagaagcc attccctgc ctcattccct aggccttttg ccaccccacc      6180
agccacacct ggcagccgag gctggccccc acagcccgtc cccaccctgc ggcttgaggg      6240
ggtcgagtcc agtgagaaac tcaacagcag cttcccatcc atccactgcg gctcctgggc      6300
tgagaccacc cccggtggcg ggggcagcag cgccgcccgg agagtccggc ccgtctccct      6360
catggtgccc agccaggctg gggccccagg gaggcagttc cacggcagtg ccagcagcct      6420
ggtggaagcg gtcttgattt cagaaggact ggggcagttt gctcaagatc ccaagttcat      6480
cgaggtcacc acccaggagc tggccgacgc ctgcgacatg accatagagg agatggagag      6540
cgcggccgac aacatcctca gcgggggcgc cccacagagc cccaatggcg ccctcttacc      6600
ctttgtgaac tgcaggacg cggggcagga ccgagccggg ggcgaagagg acgcgggctg      6660
tgtgcgcgcg cggggtcgac cgagtgagga ggagctccag gacagcaggg tctacgtcag      6720
```

-continued

```
cagcctgtag tgggcgctgc cagatgcggg cttttttttta tttgtttcaa tgttcctaat    6780
gggttcgttt cagaagtgcc tcactgttct cgtgacctgg agttaaccgg aacagcgtct    6840
tcattcattt ctgttgggac cagacgcgga gcctgggtgc gcgagccgcc ctccgggagg    6900
aaggcgcccg gctgcgtctg cagaggcggg gagaggaggc ggcgagggtc ccggggcgcg    6960
aggaaggcgc ctgccctctc ccagctcgca ggccccgggc ccggccgcgc ctccgcgggg    7020
agagcacccc ggcttcccgc gcgccctcac caaaaggacc ctacagcaaa cgggtgtctt    7080
tcgactctgc ttgtagaaac catttgcaca tattctgtac gagcctcgct gtctccctag    7140
agccagggcc ctgcggattt ggagaaggga gcggggcagg acttccagga ggaccccaac    7200
ccggcccgga gagggaggag gaggcctcca ggggcgcgga gctctgggga tgggcgtcgg    7260
gccggcagtg gtgcggctca ctccgtccct gcccacctgc gacgggatcc cccgaccggc    7320
acgggccacg ccgagctccc ggccagccgc cggcccgcag gcagcgcgag ggaggagctg    7380
cgccgccggc tccgcccaac caggtggtgc tgagcttccg ctgagcgctc ttttgttttg    7440
tggtttgaca cttttcttga cagcatgttg cagtttcttt tcggtttttgg tttttttttaa    7500 atgtttatt ttgctttccc agcgggaggg gaggaagaag agtgtttaca aagtcctgta    7560 gcccctcac ctttctgttt tcacttttgc caatgtacat cgggtttggt tttcttgtat    7620
tatttaaacg gttgtggttt ccttttttcca cggaggttca atagaagccg ctgcaggaga    7680
gttttaccaa ccattgtgta tgcccaataa tttgttatca tttccttagg tagtaaccta    7740 ttttttgttct ggtttggttc ggttatctaa tggaaaggta actggcaatg cacttgatgt    7800
ggtcttgcac atgtgggtga tagagttggg ttccttttta tgctgggtgt acaggtgggt    7860
ttgggagaga ggagcatgcg cgagagagtc tccgagtgtg tgcgacgcgt gtgtgtgtgg    7920
tgggttgtct gtgtgcatat gtcctgcccg tgtatatgca cccacaccat gtgcccgtgc    7980
acaccagtga ctacgcagtc ccccctttct ggtttagctg tgggaagatc tgaatctggg    8040
gccgtttgaa agcaaaaaca aaccactgtc tctgcttctg aaacgggaat cagtaactct    8100 ttgcatttc tgtcccacaa gatatgcaaa aacaatgcaa taatattcat ttaaaaatac    8160
aattgtgagt tgtgttggca ttaaaactgt attttaaaaa aagacagaaa tttaagggaa    8220
aaacacaaga aggcattttg cttcaatata ttccgtgtaa tgttttattg cattgataat    8280
gtttctgttg aagaaaccgt tatacttgaa ttcaggtcag tttcagtatt tttcaaatat    8340
ttttttaaaa ctgaattgca attgtgccaa gcgaatataa tgaattgaat taagttggtt    8400
ttcggattca cttcttgtat attttgctgc atgtaaagta aatcattttg tatttggagt    8460
gtgacaagct ttacctttga actcaagtgc ttttctatat gtggttgggg gaaagggaac    8520
aagtttcctt tagtttgcac aatgagcaaa ggtatcacca gtgtagtcat tattctgctc    8580
tccacaaaca ggtttggaca ttactgtttt gcatatcttg tgtttgctta catttccctc    8640
aatttttcca aaatcgtttg ctgggtatgt ttgtaccgcc tcttgctgtg agagaccagg    8700
acctatttta ttccagtctt cactctgtcc actctgctct ggtcatctga tttggtactt    8760
ctccaagaac agcccttcac tgtgaggtgc agggaggcgt tctgatgagc cctcagtcac    8820
tgggccgtca tccgcatccc ccatggaaga ggtagctggc tttcccttcc cttccaccac    8880
acggaatttt ctctttggct tccttaggaa agtgtacact aaccgggagg ataaaattaa    8940
agtcaggctg cttggaggga ggggcatcct cacttccgga ttcttgttgc tctacccaac    9000
aaggacagca ggggctcgag aaaggaactg gtgaaaccct gatccatctg aaagtcaact    9060
```

-continued

```
ctgcgtgctc ctttctccat cccttcctca ctctggagca gcctttcctt caggcttgcc    9120
ctaatgtttg ggctgccggg gagggggcca ggacaaggga agaggcatcc ggagctcaca    9180
gtgggggtgg gaacagattt ttgtgggggc atctctaatg ctcacttata tctccctaga    9240
acatcactct tttggtgctg tgtccttcaa atgtatgtca acagtggtgg ctgaaaaggg    9300
actgctttgg ggaaaacagg acccaaccat tcacccagaa ttgacccatt aaatctcttc    9360
cagtcctagt gttccctgag cccctcttgg cacatatata agtaagctag aaattacaat    9420
aagggacagt ccattcctct atgacagctt gctggactga ttcatgacaa agtggagaaa    9480
tgtactcaat actccccggt taacacagtc tagaaacaga gtttcttttat ggatatccac    9540 acccaagtca tccaaacttt cttgattcct tttcactgcc atcaaggtcc tctagaaatt    9600
gagtttaggt atcatccttt gaaaagttcc caagatttct accaggaggt acacacaggc    9660
gttccctgtc tagggcagga ggactatcct agcttgacct tctgatccac tagaataaga    9720
ctggcgtatg atgcctgtca tcagaacaga ctggcacaag tagtgacatc aatgaaccac    9780
agcacaatct tccaagtgat gtctactctc cacctaaaat ggaattttcc ccatgacctt    9840
gtaaaacata attgtcacat cttccatacc cctcctgaca gcccccaagt gtcaggagaa    9900
aacagtcagg ggctaagggc ccaagggact tgaagaaaca acagtttaag gtctgcagtt    9960
tggtcaactt aattcttgtc ctccgaccag ccctgcctct ttcatttcca gaccttggag    10020 aattttttccc agctttgatt cagaaggtac tagttataac ccctttcctt cttcttaatc    10080
caataggcct cactctcact gggaaatcca ctcaaaggaa caaggcaatg tctctcattc    10140
tatttcccag ttccaaattc caggtgcttg tctggagtga agctacccgt tactttctcc    10200
cagcttttct ccacccagca tgtctcctgc ccatgcagct gaagacagtg gggcaacctc    10260
aggagaagca gacctttcca tgcccaagtt catctcctga gcaacagtga cacctagaaa    10320
atgaggactt tggaagtcac ccaaaagatg gtggctactt tatggagtcc tgaagataca    10380
cagccaccac tcctaaaggc aaagaaagaa aacacgaatg taggtcaggg atagagtgga    10440
accctggtca tcggggtttt tagcctcatc gtgggaaagg tggtaaagga ggatgatggc    10500
atctccatcc ctagaggcca agaattgaaa tatcattgtc aaggattaga aacaattcag    10560
caaagaggcc acaaaaaggg cctgctgact cccagaagac ctctttaaac cccaggggag    10620
gcaaatactt gctgatggag tctgggccgt ttccatattt taaagaagac ctgcctctgg    10680
ggcaaatgtc agcacagaga ggactgggag gagaatggag gcaagaaaag ggcatatttt    10740
gactccctct gtgcctcttc ccagttcatg gaaggatgtg ttcagcttac ccacccacag    10800
tgaccagtgt ggtggagccg ctgacatctc aaggatctat ttgggaaggt gagaagagta    10860
ctcattccat ctgggggtgt tgttccagcc acatcagcct acctggtggg atgtgggggt    10920
gtctgccacc ctgtcccccc tctgctgatg tccctcccct caggctgtcc aggtgccacc    10980
tgacacaggc tgctgtgcaa agacaggcgg ggaagcccaa acctcactcc cagggaggcc    11040
ctcagccgcc agagtccagg ttctccagag gctacgattt gaggaggttg aggggaagaa    11100
caggagggaa agaaaagtcc tacaactgtc aggaatgggg cacctttccc tgtccctaag    11160
caaagctccc tcttcccact gccctcccca gccccagctc cctgtcctcc caacaccta     11220 gtgagaaaga cggtgcgtgg aagggagtcc catgggcaga tgcttacacg acctctttgt    11280
gaagcctctt ctgggtttaa cttcattcat caatttattc ttatgtcaaa gcaatgaaac    11340
ttttctttct ggagccagat accaatacaa caggtgaacg ggtttctgcc acatctctac    11400
attgacgggg gatgcttgaa caacccccct cactacacag acacacaccg ttaaggcaca    11460
```

-continued

```
agggctgggg ttgagctcta gatgagggac tttcctgctc ctgcaagggt gagcactgta      11520
tacacagaca aggagggtgc agtagagtga ctcccttgga tggaagtagt accatcagaa      11580
cctactatta ttatgacata aattctattt acatacattg agagaatact acaatcaaca      11640 cttttttcctg ggatgacttt aagaggtttg agccacagca cctgaagtgg caaagatcca     11700
tggtctttgt agggtattag agaactcttc cagtcacctc tgaaagcact ctagatcttg      11760
cagctgagtg gatgaagtgt aacaaatctg ttgcacgctg agaggagtca gaattagcat      11820
ttttcatgaa agttccccac gtctctacta agaatgagga agaaaagact aagactaggt      11880
aattacacag aggcttgaaa tgttacatca ccagagccaa gtcctctccc ttcagatcag      11940
ttactggctg ctacacaggg acacccccac cttttcaggg catcccatgc actccacttc      12000
tcaggatcta aggaatttga ctttgtaggg atcccagaaa gggcactgtg ccacttcccc      12060
tggtgtgaat cagacataca ttgtacattc atttctaaaa ttcactcatg cacctcaaac      12120
caaggtcatt atccaaaaaa aaaaaaaaaa agctctgggt ggaagagttt gtaagtttta      12180
agagagggtc atttctatgt gaggaaatgc agaaatggac agaatgattc ttattcactg      12240
tttgggtctg gagaattccc attgtggaaa tcttagagat ctcaagttta ttaccaaggg      12300
aataaggaaa aaaaggtgag caggcaccag gccaagcagt ggctcccttg ccaaggaacc      12360
tgaggctgca ggtttcaggg accccccttga agaaacctct cctggccatt ggccaggaga     12420
aaagagaagt ctctcctgta gagtcacaag agaagcaaaa gagggtgggt cactgggtcc      12480
tggacatagc ccccaacccc aagacttccc aatatggaga aactacacca atgtttaaaa      12540
ggggaaaagg aaagaacttg tacatcaagg gaagatgatt tgtaaacaca cagtcctgtg      12600
cagaaagatc cccttcagga ggtgtctcca gcatcccaaa gctgtgcgca ccttctcttt      12660
tcctgcctca ggccacctat gcatccagct gcagcccata cccacacctg aaatccatct      12720
cttgaatccc agccaggtta tataccaccc cattgccatg tcctgtcctg gccagaatgc      12780
atgctgttcc cccaagcctc gtgggagtga ggccatggga aacagagatg agcatgtctg      12840
gacaagtctg tgatggtagt ggatgagaat aacccatggc aaaacacgca cattcattaa      12900
gaaatagggc gacagattcc ccgttggtga agcactgaaa ggtctattac tctcataata      12960
ttgctgtttt attttaatcc accagagcta ccatgcaaaa ctttcctcct gtgaaacgct      13020
ccagataaag ctcctctaat ctccccttcc ctcatgtcct ccagctcaaa cccaccttca      13080
tcccccaaac caatctgtat catgcctgtt atcagagagg cacagaaaga tgggcagtgc      13140
ctccgttgtc accattcccc acacccctac acacccccac accctcccct ccaggctcca      13200
cgacttcaca gtcttactgt tgtaaatatc attgtacagt ttgtaatcct caaataatcc      13260
cattgtcaga ggcctcgcct gatgggcctt ctcaccctcg agaaaggcca gggaatctag      13320
aaggggcaac ccttcaagga gagcttcagg gtcatctctg tgtgagacac tattgtatat      13380
tcctgtaaga ttgcattttt atctaaggaa tgatgttatt taaaaaacaa acaaaaaaca      13440
caaaaaataa gaattgcaaa taaatttctt aacaatgtct                            13480
```

<210> SEQ ID NO 9
<211> LENGTH: 2737
<212> TYPE: DNA
<213> ORGANISM: Homo sapiens

<400> SEQUENCE: 9

```
gctctcagtc ggagcgaagc ggctggcgga gcagaacgga ttgcagggtc agccatgtca       60
```

-continued

```
tctgagcctc ccccaccacc acagccccc acccatcaag cttcagtcgg gctgctggac      120
acccctcgga gccgtgagcg ctcaccatcc cctctgcggg gcaacgtggt cccaagccca      180
ctgcccactc gccggacgag gaccttctcg gcgacggtgc gggcttcaca gggccccgtc      240
tacaaaggag tctgcaaatg cttctgccgg tccaagggcc atggcttcat taccccagct      300
gatggcggcc ccgacatctt cctgcacatc tctgatgtgg aaggggagta tgtcccagtg      360
gaaggcgacg aggtcaccta taaaatgtgc tccatcccac ccaagaatga gaagctgcag      420
gccgtggagg tcgtcatcac tcacctggca ccaggcacca agcatgagac ctggtctgga      480
catgtcatca gctcctagga gatggtggaa gcacccttg tcctgtgctt gtgggagact      540
ttgcagggag gaggcagcag acactggaga tgacattctt ccacacgaga cggggcttca      600
gccgggcatg gtccctctca agtatctcct ggaggaaggg gtatgggggg caggtgtggg      660 gtgtgggtg ttcccggcca tcagcacagc ctatgaccat tgcaacaacc tctcaccatc      720
tgaagagcat taaaagcatt taaaaaggag aggtgcccac tggtggctga gtggaggttc      780
caaccccatc ccagggagtg gatcaagggt ggtatttctc cagctgctca gacacatggg      840
ctcaacccac agaatccctc ttcctcctgg agctggaggc cccagattcc cagatctggc      900
cccctggcag cctgacaggg accttgcgtg acttctccaa ggcaaatttc cacctaagtg      960
ccccttgcgc ctctcctggg gcctgggcaa agcagttttc taattcttgg cttggttggt     1020
tctaggggag ctggcttgaa gtgggtgggg aaaggcgggg gtggcggtct ttggattgga     1080
cggatgttgc cttttggtgc ctttgcagtg ggaggcggca tagctgcctg tctggggaag     1140
acagttctcc cagcactccc acccctgggc acagcaggct ggtactggga ggctgaaccc     1200
ctcttagagc ctgacctttt catctgcctt ctggttgtgt gaccatcact caacagccat     1260
ttcacagccc ctgtaattat ggcggcgggg ggctggggtg gtggtggtgg gaagggcttg     1320
tggagaggac acagtctttg tttaaaaact ttgtcccgat ccatccagaa aagagtaggt     1380
agcttgcatc ctgacagcct ggcaaagtca agaaagttga aggagaaaca tacctttgga     1440 gaggggttt tctttaaaac tagtgttaag aaatgcttag ggattttttt tttcttattt     1500
ttcataacta aagctttcac ccagagccgg ctctgtttgc actttgctgc cgacattgca     1560
aactttttgg cagggtggga gactgagtct cattctgtca cccaggctgg agtgcagtgg     1620
cccgatctca gcttactgca acctctgccc tccagggttc tggcaattcc gcctcagtct     1680
cctgagtagc tgggattaca ggcatgcgcc accacacccg gttaattttt gtattttag      1740 tagagaccag gtttcatcat gttgggcagg atggtcttga acccctgacc tcagatgatc     1800
tgcccatctc ggcctctcaa agtgctggga ttacaagtgt gagccatcgc gccggcctg      1860 caaacttttt tgtaggtatt tctggtaaac aaatccttag gttatctttg ctgtggttgt     1920
ggtttggctt tagtcatgat ttcaaagtag aaatagctag gcattatttt ttgaaatata     1980
tgacctatat gtagtcaaga atccactgaa cagaggcaag caaacctttt ggaaactggc     2040
ttttgggcag acagtaaacg tccagtttga tgctggaagc atgaacagct tcatcaggta     2100
ggtactcctc aactctgatg agtttgtcct ttcagcctaa gggggtggaa gggagttgtt     2160
tgagaataga aaatacgcat gttgattgcg agtgtgtgga gacaaaggca gttcccacca     2220
cagttaggtc ctggccattg tttcctcgcc tgcgatgctc cttgtacatc ctcaccctcc     2280
tctcccgcct ctgccttctg ctgggtcaaa ggtggccttt tctctccagc cttgaattgt     2340
tccctgttgg cttcccaagg gcccatctgc tggtacagtc cacacttcca cagccaagac     2400
ccgagagggc tttcactgcc ccaagcctct ctcctgtgac cctgggattc tgtcttggca     2460
```

-continued

```
gaatcctttg tcagcggctc ttactctgtc cttcctgttt ggccacagct ctttcaatca    2520
atgggtattc tagaaccgca ggatgtcaga gctggaaggg acgcgatacc ggtttacaca    2580
aggggaaact cctcgaggct ctgggaggga cggagggttt tggtgacaga gcgagagcta    2640
aaattgagga ttcctgaatc cagatcttgc ctcccatcag ccatctttct cccaataaat    2700
ttttgttttg tgcaaggcta aaaaaaaaaa aaaaaaa                             2737
```

<210> SEQ ID NO 10
<211> LENGTH: 8980
<212> TYPE: DNA
<213> ORGANISM: Homo sapiens

<400> SEQUENCE: 10

```
ggaggttgtg gggccgccgc cgcggagcac cgtccccgcc gccgcccgag cccgagcccg     60
agcccgcgca cccgcccgcg ccgccgccgc cgccgcccga acagcctccc agcctgggcc    120
cccggcggcg ccgtggccgc gtcccggctg tcgccgcccg agcccgagcc cgcgcgccgg    180
cgggtggcgg cgcaggctga ggagatgcgg cgcggagcgc cggagcaggg ctagagccgg    240
ccgccgccgc ccgccgcggt aagcgcagcc ccggcccggc gcccgcgggc cattgtccgc    300
cgcccgcccc gcgccccgcg cagcctgcag gccttggagc ccgcggcagg tggacgccgc    360
cggtccacac ccgccccgcg cgcggccgtg ggaggcgggg gccagcgctg gccgcgcgcc    420
gtgggacccg ccggtcccca gggccgcccg gccccttctg gacctttcca cccgcgccgc    480
gaggcggctt cgcccgccgg ggcgggggcg cggggtggg cacggcaggc agcggcgccg     540
tctcccggtg cggggcccgc gccccccgag caggttcatc tgcagaagcc agcggacgcc    600
tctgttcaac ttgtgggtta cctggctcat gagaccttgc cggcgaggct cggcgcttga    660
acgtctgtga cccagccctc accgtcccgg tacttgtatg tgttggtggg agtttggagc    720
tcgttggagc tatcgtttcc gtggaaattt tgagccattt cgaatcactt aaaggagtgg    780
acattgctag caatgagctc ccaaagccat ccagatggac tttctggccg agaccagcca    840
gtggagctgc tgaatcctgc ccgcgtgaac cacatgccca gcacggtgga tgtggccacg    900
gcgctgcctc tgcaagtggc cccctcggca gtgcccatgg acctgcgcct ggaccaccag    960
ttctcactgc ctgtggcaga gccggccctg cgggagcagc agctgcagca ggagctcctg   1020
gcgctcaagc agaagcagca gatccagagg cagatcctca tcgctgagtt ccagaggcag   1080
cacgagcagc tctcccggca gcacgaggcg cagctccacg agcacatcaa gcaacaacag   1140
gagatgctgg ccatgaagca ccagcaggag ctgctggaac accagcggaa gctggagagg   1200
caccgccagg agcaggagct ggagaagcag caccgggagc agaagctgca gcagctcaag   1260
aacaaggaga agggcaaaga gagtgccgtg gccagcacag aagtgaagat gaagttacaa   1320
gaatttgtcc tcaataaaaa gaaggcgctg gcccaccgga atctgaacca ctgcatttcc   1380
agcgaccctc gctactggta cgggaaaacg cagcacagtt cccttgacca gagttctcca   1440
ccccagagcg gagtgtcgac ctcctataac cacccggtcc tgggaatgta cgacgccaaa   1500
gatgacttcc ctcttaggaa aacagcttct gaaccgaatc tgaaattacg gtccaggcta   1560
aagcagaaag tggccgaaag acggagcagc ccctgttac gcaggaaaga cgggccagtg    1620
gtcactgctc taaaaaagcg tccgttggat gtcacagact ccgcgtgcag cagcgcccca   1680
ggctccggac ccagctcacc caacaacagc tccgggagcg tcagcgcgga gaacggtatc   1740
gcgcccgccg tccccagcat cccggcggag acgagtttgg cgcacagact tgtggcacga   1800
```

-continued

```
gaaggctcgg ccgctccact tcccctctac acatcgccat ccttgcccaa catcacgctg   1860
ggcctgcctg ccaccggccc ctctgcgggc acggcgggcc agcaggacgc cgagagactc   1920
acccttcccg ccctccagca gaggctctcc cttttccccg gcacccacct cactccctac   1980
ctgagcacct cgcccttgga gcgggacgga ggggcagcgc acagccctct tctgcagcac   2040
atggtcttac tggagcagcc gccggcacaa gcacccctcg tcacaggcct gggagcactg   2100
cccctccacg cacagtcctt ggttggtgca gaccgggtgt ccccctccat ccacaagctg   2160
cggcagcacc gcccactggg gcggacccag tcggccccgc tgccccagaa cgcccaggct   2220
ctgcagcacc tggtcatcca gcagcagcat cagcagtttc tggagaaaca caagcagcag   2280
ttccagcagc agcaactgca gatgaacaag atcatcccca agccaagcga gccagcccgg   2340
cagccggaga gccacccgga ggagacggag gaggagctcc gtgagcacca ggctctgctg   2400
gacgagccct acctggaccg gctgccgggg cagaaggagg cgcacgcaca ggccggcgtg   2460
caggtgaagc aggagcccat tgagagcgat gaggaagagg cagagccccc acgggaggtg   2520
gagccgggcc agcgccagcc cagtgagcag gagctgctct tcagacagca agccctcctg   2580
ctggagcagc agcggatcca ccagctgagg aactaccagg cgtccatgga ggccgccggc   2640
atccccgtgt ccttcggcgg ccacaggcct ctgtcccggg cgcagtcctc acccgcgtct   2700
gccaccttcc ccgtgtctgt gcaggagccc cccaccaagc cgaggttcac gacaggcctc   2760
gtgtatgaca cgctgatgct gaagcaccag tgcacctgcg ggagtagcag cagccacccc   2820
gagcacgccg ggaggatcca gagcatctgg tcccgcctgc aggagacggg cctccggggc   2880
aaatgcgagt gcatccgcgg acgcaaggcc accctggagg agctacagac ggtgcactcg   2940
gaagcccaca ccctcctgta tggcacgaac cccctcaacc ggcagaaact ggacagtaag   3000
aaacttctag gctcgctcgc ctccgtgttc gtccggctcc cttgcggtgg tgttggggtg   3060
gacagtgaca ccatatggaa cgaggtgcac tcggcggggg cagcccgcct ggctgtgggc   3120
tgcgtggtag agctggtctt caaggtggcc acaggggagc tgaagaatgg ctttgctgtg   3180
gtccgccccc ctggacacca tgcggaggag agcacgccca tgggcttttg ctacttcaac   3240
tccgtggccg tggcagccaa gcttctgcag cagaggttga gcgtgagcaa gatcctcatc   3300
gtggactggg acgtgcacca tggaaacggg acccagcagg ctttctacag cgaccccagc   3360
gtcctgtaca tgtccctcca ccgctacgac gatgggaact tcttcccagg cagcggggct   3420
cctgatgagg tgggcacagg gcccggcgtg ggtttcaacg tcaacatggc tttcaccggc   3480
ggcctggacc cccccatggg agacgctgag tacttggcgg ccttcagaac ggtggtcatg   3540
ccgatcgcca gcgagtttgc cccggatgtg gtgctggtgt catcaggctt cgatgccgtg   3600
gagggccacc ccacccctct tgggggctac aacctctccg ccagatgctt cgggtacctg   3660
acgaagcagc tgatgggcct ggctggcggc cggattgtcc tggccctcga gggaggccac   3720
gacctgaccg ccatttgcga cgcctcggaa gcatgtgttt ctgccttgct gggaaacgag   3780
cttgatcctc tcccagaaaa ggttttacag caaagaccca atgcaaacgc tgtccgttcc   3840
atggagaaag tcatggagat ccacagcaag tactggcgct gcctgcagcg cacaacctcc   3900
acagcggggc gttctctgat cgaggctcag acttgcgaga cgaagaagc cgagacggtc   3960 accgccatgg cctcgctgtc cgtgggcgtg aagcccgccg aaaagagacc agatgaggag   4020
cccatggaag aggagccgcc cctgtagcac tccctcgaag ctgctgttct cttgtctgtc   4080
tgtctctgtc ttgaagctca gccaagaaac tttcccgtgt cacgcctgcg tcccaccgtg   4140
gggctctctt ggagcaccca gggacaccca gcgtgcaaca gccacgggaa gcctttctgc   4200
```

-continued

```
cgcccaggcc cacaggtctc gagacgcaca tgcacgcctg ggcgtggcag cctcacaggg   4260
aacacgggac agacgccggc gacgcgcaga cacacggaca cgcggaagcc aagcacactc   4320
tggcgggtcc cgcaagggac gccgtggaag aaaggagcct gtggcaacag gcggccgagc   4380
tgccgaattc agttgacacg aggcacagaa aacaaatatc aaagatctaa taatacaaaa   4440
caaacttgat taaaactggt gcttaaagtt tattacccac aactccacag tctctgtgta   4500
aaccactcga ctcatcttgt agcttatttt tttttaaaga ggacgttttc tacggctgtg   4560
gcccgcctct gtgaaccata gcggtgtgcg gcgggggggtc tgcacccggg tgggggacag   4620
agggaccttt aaagaaaaca aaactggaca gaaacaggaa tgtgagctgg gggagctggc   4680
ttgagtttct caaaagccat cggaagatgc gagtttgtgc ctttttttttt attgctctgg   4740 tggatttttg tggctgggtt ttctgaagtc tgaggaacaa tgccttaaga aaaaacaaac   4800
agcaggaatc ggtgggacag tttcctgtgg ccagccgagc ctggcagtgc tggcaccgcg   4860
agctggcctg acgcctcaag cacgggcacc agccgtcatc tccgggggcca ggggctgcag   4920 cccggcggtc cctgttttgc tttattgctg tttaagaaaa atggaggtag ttccaaaaaa   4980
gtggcaaatc ccgttggagg ttttgaagtc caacaaattt taaacgaatc caaagtgttc   5040
tcacacgtca catacgattg agcatctcca tctggtcgtg aagcatgtgg taggcacact   5100
tgcagtgtta cgatcggaat gcttttttatt aaaagcaagt agcatgaagt attgcttaaa   5160
ttttaggtat aaataaatat atatatgtat aatatatatt ccaatgtatt ccaagctaag   5220
aaacttactt gattcttatg aaatcttgat aaaatatttta taatgcattt atagaaaaag   5280
tatatatata tatataaaat gaatgcagat tgcgaaggtc cctgcaaatg gatggcttgt   5340
gaatttgctc tcaaggtgct tatggaaagg gatcctgatt gattgaaatt catgtttttct   5400 caagctccag attggctaga tttcagatcg ccaacacatt cgccactggg caactaccct   5460
acaagtttgt actttcattt taattatttt ctaacagaac cgctcccgtc tccaagcctt   5520
catgcacata tgtacctaat gagttttttat agcaaagaat ataaatttgc tgttgatttt   5580
tgtatgaatt ttttcacaaa aagatcctga ataagcattg ttttatgaat tttacatttt   5640
tcctcaccat ttagcaattt tctgaatggt aataatgtct aaatctttttt cctttctgaa   5700 ttcttgcttg tacattttttt tttacctttc aaaggttttt aattatttttt gtttttattt   5760 ttgtacgatg agttttctgc agcgtacaga attgttgctg tcagattcta ttttcagaaa   5820
gtgagaggag ggaccgtagg tctttttcgga gtgacaccaa cgattgtgtc tttcctggtc   5880
tgtcctagga gctgtataaa gaagcccagg ggctcttttt aactttcaac actagtagta   5940
ttacgagggg tggtgtgttt ttcccctccg tggcaagggc agggagggtt gcttaggatg   6000
cccggccacc ctgggaggct tgccagatgc cggggcagt cagcattaat gaaactcatg   6060
tttaaacttc tctgaccaca tcgtcaggat agaattctaa cttgagtttt ccaaagacct   6120
tttgagcatg tcagcaatgc atggggcaca cgtgggggctc tttacccact tgggtttttc   6180
cactgcagcc acgtggccag ccctggattt tggagcctgt ggctgcaagg aacccaggga   6240
cccttgttgc ctggtgaacc tgcagggagg gtatgattgc ctgaccagga cagccagtct   6300
ttactctttt tctcttcaac agtaactgac agtcacgttt tactggtaac ttatttttcca   6360 gcacatgaag ccaccagttt cattccaaag tgtatattgg gttcagactt gggggcagaa   6420
gttcagacac accgtgctca ggagggaccc agagccgagt tcggagtttt ggtaaagttt   6480
acagggtagc ttctgaaatt aactcaaact tttgaccaaa tgagtgcaga ttcttggatt   6540
```

-continued

```
cacttggtca ctgggctgct gatggtcagc tctgagacag tggtttgaga gcaggcagaa    6600
cggtcttggg acttgtttga ctttcccctc cctggtggcc actctttgct ctgaagccca    6660
gattggcaag aggagctggt ccattcccca ttcatggcac agagcagtgg cagggcccag    6720
ctagcaggct cttctggcct ccttggcctc attctctgca tagccctctg gggatcctgc    6780
cacctgccct cttaccccgc cgtggcttat ggggaggaat gcatcatctc actttttttt    6840
tttaagcaga tgatgggata acatggactg ctcagtggcc aggttatcag tgggggggact   6900 taattctaat ctcattcaaa tggagacgcc ctctgcaaag gcctggcagg gggaggcacg    6960
tttcatctgt cagctcactc cagcttcaca aatgtgctga gagcattact gtgtagcctt    7020
ttctttgaag acacactcgg ctcttctcca cagcaagcgt ccagggcaga tggcagagga    7080
tctgcctcgg cgtctgcagg cgggaccacg tcagggaggg ttccttcatg tgttctccct    7140
gtgggtcctt ggacctttag cctttttctt cctttgcaaa ggccttgggg gcactggctg    7200
ggagtcagca agcgagcact ttatatccct ttgagggaaa ccctgatgac gccactgggc    7260
ctcttggcgt ctgccctgcc ctcgcggctt cccgccgtgc cgcagcgtgc ccacgtgccc    7320
acgccccacc agcaggcggc tgtcccggag gccgtggccc gctgggactg gccgcccctc    7380
cccagcgtcc cagggctctg gttctggagg gccactttgt caaggtgttt cagtttttct    7440
ttacttcttt tgaaaatctg tttgcaaggg gaaggaccat ttcgtaatgg tctgacacaa    7500
aagcaagttt gattttttgca gcactagcaa tggactttgt tgtttttctt tttgatcaga    7560
acattccttc tttactggtc acagccacgt gctcattcca ttcttctttt tgtagacttt    7620
gggcccacgt gttttatggg cattgataca tatataaata tatagatata aatatatatg    7680
aatatatttt tttaagtttc ctacacctgg aggttgcatg gactgtacga ccggcatgac    7740
tttatattgt atacagattt tgcacgccaa actcggcagc tttggggaag aagaaaaatg    7800
cctttctgtt cccctctcat gacatttgca gatacaaaag atggaaattt ttctgtaaaa    7860
caaaaccttg aaggagagga gggcggggaa gtttgcgtct tattgaactt attcttaaga    7920
aattgtactt tttattgtaa gaaaaataaa aaggactact taaacatttg tcatattaag    7980
aaaaaaagtt tatctagcac ttgtgacata ccaataatag agtttattgt atttatgtgg    8040
aaacagtgtt ttagggaaac tactcagaat tcacagtgaa ctgcctgtct ctctcgagtt    8100
gatttggagg aattttgttt tgttttgttt tgtttgtttc cttttatctc cttccacggg    8160
ccaggcgagc gccgcccgcc ctcactggcc ttgtgacggt ttattctgat tgagaactgg    8220
gcggactcga aagagtcccc ttttccgcac agctgtgttg acttttttaat tacttttagg   8280 tgatgtatgg ctaagatttc actttaagca gtcgtgaact gtgcgagcac tgtggtttac    8340
aattatactt tgcatcgaaa ggaaaccatt tcttcattgt aacgaagctg agcgtgttct    8400
tagctcggcc tcactttgtc tctggcattg attaaaagtc tgctattgaa agaaaaagaa    8460
agcgaacagt ttttgtttgt ttttttttgcc gtgtgtgctc catagtggag gcgctatttt   8520
ccaattgatg agaatgacaa acatatataa tctatctatc tatctatcta tctatctatc    8580
tatacagggg gcttgaacct tactcaccca agagcttctt acggaatgtg gtagaaaacc    8640
aagttgtaac gacactgtaa cctacctgat gcctgttcgc gcccgccgtg agctgcgcac    8700
tggccgtggc caccattcac ctctgtaatt taatccgttt ctcttggatt gtctggacgt    8760
gcccgatggt tctttctttt gctcagtgga gttggaggtt ttgtgtttgg ttttctcatt    8820
cttgtcttgt tttgtgtggg tggattttca ccgaccaatg atatcctctt ctgacggtca    8880
ccttctttcc acttcactgg agtccagtat tctgtaccac atcacgcaac gtgttatctt    8940
```

-continued

```
gtggtgtaaa taaagactgc gttacttgcc ctcccaaaaa                    8980

<210> SEQ ID NO 11
<211> LENGTH: 8293
<212> TYPE: DNA
<213> ORGANISM: Homo sapiens

<400> SEQUENCE: 11
caaccgtggc cgggtcctcg cggctggaga acccaaccga cagtgggcgg caggacgcac      60
cgcggacccc ggagagagcg gacgagcagg gcgccggcgc catggacctg gtcatcacgc     120
aggagctggc ccgcgccgag agccagcaag atgctgcgtc cttgaagaag gcctacgagt     180
tgatcaaatc ggccaaccta gggaaatcgg agtttgaccc ctcagagagc ttcagcccag     240
acctgtttgt tctgtgtgca gagcaggccc tgaagatgag gcagccagag gtgagcgagg     300
actgcatcca aatgtacttc aaggtgaagg cgcccatcac ccagtttctg ggccgagcgc     360
acctgtgcag ggcccagatg tgtgccccga agtcggcaga aaacctggag gaatttgaaa     420
attgcgtgac tgagtacatg aaggccataa actttgccaa aggagaaccg aggtactact     480
ttttggtgta caatgcatca gtcctctact ggcagatggt gaggccgttc ctcaagcctg     540
gatatcgtca ccatctgatc cccagccttt cccaaatcat aaacgtgctg agtcagactg     600
aggaggaaga caaggagtgg cgtgctgagc tgatgctgga acttctggag tgttatctgc     660
aagccggaag aaaggaggag gctgccaggt tctgctccac ggcagctccg ttcattaagt     720
ctcacgtgcc acagaaatac cggcagatat tctctgttat ggttcgtcat gaattaatgg     780
acgaacttca gttaaaggaa gaaaagaaaa attccattag cctgtcagtc actttctata     840
ttaatatgct aaaggcaaaa gcggagcaaa atgatttacc aggtgacatc agtgtcattc     900
tgaggaaggc ctacagacac ttaggtcatt acaaccacca gcgctttccc tctatcagtg     960
aagaaaaaat gcttttgctt tttgaattgg cgcgtttttc cttgaccttg aaatgcatgg    1020
agatctcctc tgcctgcctc tcagacctga agaagatgga aagcaaagat cctgggaagc    1080
ttattgaaat ggaatgtctg gagtgtgaat cggaagcttt aagacttgaa agtaagatga    1140
aagtgtacaa ccgagcggct gttgaggccc agctggatat catacagagg ctagacgtcg    1200
cgctgcagcg agccgtgcgc ctgggcgacc cccgggtcat ccacgtggtg tgcgccacgc    1260
agtggaacac ctgcctgccc ctgctgcagc acaacctgcg gcaccacctg cggaagcccc    1320
tggctggcgt tgcggacgtg ctggagaagc tggacagcct catgacgctt ctccgctgtc    1380
aagtgcacat ggagatggcg cagatcgagg aggacgagga ccggctggag cccgccacgg    1440
agcacctccg gaaagccgcg cgcctggaca gcctgggcct ctaccgggac aggatccaga    1500
tggcctccac ccggctgcgt ctgtgcacca cgctatacca ggcccctgag cgcgcagagg    1560
acaaggccat catggccgtt gagcaggcaa aaaaagctac accaaaggac agcgtcagga    1620
agaagcgggc cctcctggtg aatgcaggcc tggccttagc ccctgacgcg tttcagattg    1680
tgctggacag tgagaatgag gccaaagtct ccaccgggaa gaacaggggc cggttcacct    1740
acctctgtgc gaaggcgtgg caccacaccg tcagcgtgga caaagctgcc gggcacctgc    1800
ggcgcctggg caacgaaaac gacaaggaga ggatacagat ttgggcagag ctggccaaag    1860
tggcccggaa acaaggcgtg tgggacgtct gtcggacggc gagccgcttc tgcctcctgt    1920 atgcaacgt caaggtgaag aagttgaggc tgcggcgagg gaagaagaag cgaggtaggg    1980
acggctcggt gcaggacacc tggagccagc ctgaggtcgt cctgcagagg caggtgtgcc    2040
```

-continued

```
ccgacctgct gcggaagttc gcggaggtgg ggttcatcca tgctgaggcc acggttcatt      2100
tgctgcggtc agaaggtgta gagctgaatg accgggccat cccccccgaa gacctgagcc      2160
agcacccagc tggctacgtg cctgagcccc cggaggtgaa tgctgagtgg atcacataca      2220
gaacctggat cgagagtctg tcccggtgtg ccatgaataa ctggctgcgc tccgcagaga      2280
tcggacagga gatccaggag gcgtggattg tgcagaacgc cgtggtctac gtcctgaacc      2340
acaaccacca cctgatcctg gccgggcggc agaaggagct ggtggacgcc ctgtaccacc      2400
tcctgagcat cgttaaggcc acaggccaca gtggggaccc cgtgatgctg gtgacgctct      2460
gcaacacctt ggcgcgaggc ctgatcatca gctggattcc agtccaggct gccgagaagt      2520
ccaggaaatt catgcgacca aacgcgtttc acagcccact ggacgcagga gccacttccg      2580
agatcaaaac agcggtggag gtctgcgagt ttgccctgaa cctgaccaat gggagtgcgc      2640
ccgaggagac ggtgcccacc ggcacccggc agcagcttat cgccacctgg gtcaaggcca      2700
agcagctgct gcagcagcag attgggccac ggctgggcac cgaggagcag ggcaccaatg      2760
aggatgtcag ctcggtgacc agagtcctcg ttgccttgga aatgtactca tgcaacgggc      2820
tgggcctcat ggacttcact gtccctccc tggcccagtt ggtgaaaatg gcttccgagt        2880
gcaactggtc ggacccctg gtggagctgc agacctgac gcggctgacc cacttcgccc         2940
atgcagcgcg tgaccatgag accaccatgg cctgtgctca cagggctctg gagatgggca      3000
tcaagtacct gaagaaattt gggcccgagg agtcccggct ggtggcagag atgctgtgca      3060
cagccacggc catccagggc aggagcatca tggaaaacct gaagggccgg aagcagctgc      3120
gactggtggc agccaaggcc ttcacggaga gcgccaggtt cggaggcatc gcgggcagca      3180
gcgccctggt gatgctggcc gcgcggcatt actggaacgc ctggctccca ctgctgtcct      3240
cagccgtcta caggaagaag gccaagggtg ccctgaagag gctcatcggc atcatcaaca      3300
agacagaggc cagaaagcag gagaaaggaa agacgctgct tctgcaccag tggcccacgg      3360
ccgacttcca gggtggcggg acgaccgaag gatattttct tccaggggct gaggacgacc      3420
tggcgctccg tgctgcgctc tacggcctgc tcttccacag ccatgccgac caggacgact      3480
gggagggcgg cctcaaggtg ctggacgagg ctgtgcaggt gctgccaagg acggcccacc      3540
gcctcttgat cttcaagcac atggtcatcg tgaaggccaa gctcgggcag aatttttcga      3600
tggaaataca gaaattcaag gccgagagtg aggactactt ggcgcgcatg tggcaccgcc      3660
tggccctgaa ctcgccgagc gtgtctggag agctggcctg ctacaacaac gccatccagg      3720
ccttgcagaa gcctgagatg gagtggcaga aggtggagta cctcatggag ttcgccagt        3780 ggctccatca cagacacttt cctctcgagg acgtggtctt ccacctccgc tgggctgtcg      3840
agatcctgct ggccatgaag ccgccggcg atgtccctga gccacagccc acgccggatg        3900
gggagtacgt ggctgtggag atgcccccac ggagcccgt gtccgaggcc gaggaggcgg        3960
tgtccttgga gcagctgcgt agcgtgcggc agctggaggc gctggcccgc gtgcacatcc      4020
tgctggccct ggtgctgtcg ccgggcgccg agggctacga ggactgctgc cttgcagcct      4080
acgccttctt caggcacatc tggcaggttt ctttgatgac agcaggaaaa tcagttctgg      4140
aaaacagacc cctggcagca accagctcac atctgttatt gcctaaaaaa gagaaggaga      4200
atgagaggag taaagagaag gagaaggaga ggagtaaaga gaaggagaat gagaggagta      4260
aagagaagga caaggagaag ggaaaggagg agaaagtcaa ggagcccaag cagtctcaaa      4320
gcccagctcc tatcaaacaa ctggaagact acccatgag catagaagag tgggcttcct        4380
actcctgccc cgaggaagtg ctgtctgtac tgaaacagga cagaagtgac tctactgtga      4440
```

```
acccctcaag tatccagaag ccgacataca gtttgtattt cctggaccac ctggtcaagg    4500
ccctgcagaa gatgtgcctg cacgaactca cggttcccgt cctgcagttg ggggtgctga    4560
tttcggactc cgtggtggga agcaagggcc tgtcggatct ctaccacctt cgcctcgccc    4620
acgcgtgctc cgagctgaag ctgagagaag cagccgcgcg ccatgaagag gcggtcgggc    4680
aggtgtgcgt cagcgagctg gagcaggcca gctgcagaaa agagatcgcg ttgaaaaaag    4740
agaaaaataa ggagccttta ttagaagaaa gcctgccagc actgaatgag cagacacttc    4800
ctgtccagcc tggggagatc aaaccactgg acgccaagga caagattttg aagatgaatg    4860
gggagaccgg gagggacctg gatgggacgt cctttcccca cctgtggatg ctgaaggcag    4920
aagttctgct ggagatgaac ctgtaccagc ctgcacggct gctcctgtcg gaggcttacc    4980
tggctttcca ggagctggat gagccttgtg cagaggccca gtgcctgctc ctcctcgcac    5040
agttggccaa caaggagaaa aactatggac aagccaagaa aatgatcgca caggcccagc    5100
acctgggcgg aagtgaggag ttctggtaca attccactct gaccctggca gaggcgctct    5160
tgtccatgga acactcagga agggaagcta cggtgtgtca catatttcag aagctcatca    5220
atgccttcaa gatcctcaag aaagaaagac caaaccgatt gcctttactg gaattcatga    5280
tcacagatct agaagccagg tgcctgagcc tgcgggtcag agttgcgcag cactcagcgg    5340
tcactgaacc cacagagtgc tcgttgctac tgaaagagat ggatgatggc ctgttggaaa    5400
ttgagagaaa gtttatcgac tgtggctgca aagagaattg tgttgacgta aaactagagc    5460
gtgcgaagat caagaggtta cgtgcccaga acgagaaaga tgaagaacaa aaaactgcgt    5520
attacttgga agcgtatggc ctggcccagg gtgccgtagc tgaggaagaa gggaggcttc    5580
acagcatcca gggcttatat ggcctggccc agggcgccat ggctgaggaa gaagggaggc    5640
ttcacagcgt ccagggccta ttgtcacttc aagacttgca gaacgtcaac acgcccctga    5700
tgaggaagct ggcgcgcctc aagctcggcc tcgtggaaat ggctctggac atgctccagt    5760
tcatctggga ggaggcccac gggcagcaga gtgagcaggg gtccctggag aagctgctgg    5820
cggactatct gcagaacacc agtgactaca cttccgtcgg cctgcaatgg ttcacgctga    5880
agcggactct agcacacggg gcactggcac agctggggag cctgcagccg ctgagcgtgg    5940
gctgtgtgga gatccgcgcc cggctcctgg gcctggccgg gagggccctg cacctgctgg    6000
ccatgcaagc tgaccctgtg caccctacct gctactggga ggcgggcccc tcggtgggcg    6060
ccaagctgag cggcctcaag tctctggagc tggaggtaga ggaagagggt gccacaaagt    6120
ccagcaggga cccgccggcc tccagggcag ccccggagga gcactgcagg agaggcgagg    6180
acctgaagag gaggatggtt ctggcccagc agtacctggc tcaggcgtca gaggtgctgc    6240
tgcagtgcct acaggtggcc cttggcagtg gcctcctgga tgtcgcagca gccgccagcc    6300
tggagatggt ggagtgtgtc ggcaccctgg accctgcaac tacctgccag ttcctggctc    6360
tgtctcagat gctgctcggc ctcagagacga tgagggatgt cctgcttgca gccacagcca    6420
acaccagcag ctcacagctg gcggccctgc tgcagctaca gcaccagctc cggtgccaag    6480
acaggaccac caccagcctg ggcgcccgtg tggagcagag gctggccgcc gtgtccaagg    6540
cttggcaaaa tctctgcgtc actgagcagc atttttaacct cttgaatgag atgcctccga    6600 cctttttggat cctctttctg cacctctcag gggacaggtc ccgtctgtac ggcgctgcct    6660
acgagaaacc caagttcatt actgcagcca aaggaaaggt gcaggcggtg ggaggctcct    6720
gcaaggtgat gcgtctggcc ataagtccca ctgccttctc ccacctgctg gcctgtgccc    6780
```

-continued

```
agcagttccg gaagcagacc caggcccagg tgtacagtga ggacatggcc ctgaacatag    6840
gctcggaacc agaaggcctg caggtggaag agaaggagcg ccctgtgcag aggctcagta    6900
gcgtcctggg gcccctggag gagcttctgc agccgctatt cccctgctc agcctctcca    6960 aggccagagt gcagacacct gcggttgttg ccgattcagg gaagtcgaag ggcaaagaca    7020
aggagaggaa aacgtccaca ggacaacaca gcacagtcca gcctgaggtt gccgataaga    7080
tagtcctggt cgcagacaga catctcctgg agctgccact ggaaggtctc tctgtgttcg    7140
atgaagggac aatttcctct gtgtcacgag aattttctct tcaaatgctg tggaatcgcc    7200
tccataaaga agagacagaa ggtggcgtga aaaaggaggg aagaagcaga gaccccaaaa    7260
agagaagcct agcgaagaag ggcaggaagg gcagcatccc ccggaccatc cccctgact    7320 gcatcatagt cgactcagac aacttcaagt tcgtcgtgga cccatacgag gaggcccagg    7380
gcccagaaat gctaactcct gtctccatca cccaagacat tttggaaaga ttccaagaca    7440
cattcacgtc gcgatgggcg ggacatctgg gaagcaagca ctttcccagc caggcccagt    7500
gggagcaggc cctgggcagc tgcagcggtt tcttcttcta tggaatggag agcttcctgt    7560
cccatatatt agtggagaga ttggtcgcca tgaacttgca agagtgccag gtggcagtcc    7620
tgctggacct ggcgcggtcc taccagagct tgaagaggca catggagagc gtggagcaca    7680
ggagatctgt tggccgttgg gaagccaatt ggagaaacag tgcgtctcct tcagaagatg    7740
agtggcgacg aggcggtgaa ccaagacgag gcttctcaga ccttgaagga caagctgctg    7800
ctgctccaaa gctccgagct ccttcccacc acgctcaact tggtcctgta tgggctgccg    7860
caccaagcca tcgggtagtg caggcctgga cctgcctccc atcagctgct ggggcccag    7920 cacttgcctc tgcccttggc tctgcccctc tgccaaccca tccccacctc ccggctccca    7980
tccccagctc ccagctcgct ctccccttcc tgggcctctc cccagcccctt ggtgcagcct    8040 cagccaggga ccctcccccca gcgacttccc gcaaggcagc cgcctggacc tcgagctctg    8100
cctgcctgtg tgcgccatgg ggtctgcgtc ggggctggag ctgcgtctct ccccgggggcc    8160 aggacaaggg cggcctcccc ttggcggcgc tggtgctgag ttgcttagac cagaagacta    8220
ttcagaccgt gagcctgttt ttgatttgag tgttccacta aacaaacaac aaaagccaaa    8280
aaaaaaaaaa aaa    8293
```

```
<210> SEQ ID NO 12
<211> LENGTH: 2605
<212> TYPE: DNA
<213> ORGANISM: Homo sapiens

<400> SEQUENCE: 12
```

```
cttaaacgcg actcaaggcg tcgggtttgt tgtcaaccaa tcacaaggca gcctcgctcg    60
agcgcaggcc aatcggcttt ctagctagag ggtttaactc ctatttaaaa agaagaacct    120
ttgaattcta acggctgagc tcttggaaga cttgggtcct tgggtcgcag gtgggagccg    180
acgggtgggt agaccgtggg ggatatctca gtggcggacg aggacggcgg ggacaagggg    240
cggctggtcg gagtggcgga gcgtcaagtc ccctgtcggt tcctccgtcc ctgagtgtcc    300
ttggcgctgc cttgtgcccg cccagcgcct ttgcatccgc tcctgggcac cgaggcgccc    360
tgtaggatac tgcttgttac ttattacagc tagagggtct cactccattg cccaggccag    420
agtgcgggga tatttgataa gaaacttcag tgaaggccgg gcgcggtggc tcatgcccgt    480
aatcccagca ttttcggagg ccgaggctgg agtgcaatgg tgtgatctca gctcactgca    540
acctctgctt cctgggttta agtgattctc ctgcctcagc ctcccgagta gctgggatta    600
```

```
caggcatcat ggaccgatct aaagaaaact gcatttcagg acctgttaag gctacagctc      660
cagttggagg tccaaaacgt gttctcgtga ctcagcaatt tccttgtcag aatccattac      720
ctgtaaatag tggccaggct cagcgggtct tgtgtccttc aaattcttcc cagcgcattc      780
ctttgcaagc acaaaagctt gtctccagtc acaagccggt tcagaatcag aagcagaagc      840
aattgcaggc aaccagtgta cctcatcctg tctccaggcc actgaataac acccaaaaga      900
gcaagcagcc cctgccatcg gcacctgaaa ataatcctga ggaggaactg gcatcaaaac      960
agaaaaatga agaatcaaaa aagaggcagt gggctttgga agactttgaa attggtcgcc     1020
ctctgggtaa aggaaagttt ggtaatgttt atttggcaag agaaaagcaa agcaagttta     1080
ttctggctct taaagtgtta tttaaagctc agctggagaa agccggagtg gagcatcagc     1140
tcagaagaga agtagaaata cagtcccacc ttcggcatcc taatattctt agactgtatg     1200
gttatttcca tgatgctacc agagtctacc taattctgga atatgcacca cttggaacag     1260
tttatagaga acttcagaaa ctttcaaagt ttgatgagca gagaactgct acttatataa     1320
cagaattggc aaatgccctg tcttactgtc attcgaagag agttattcat agagacatta     1380
agccagagaa cttacttctt ggatcagctg gagagcttaa aattgcagat tttgggtggt     1440
cagtacatgc tccatcttcc aggaggacca ctctctgtgg caccctggac tacctgcccc     1500
ctgaaatgat tgaaggtcgg atgcatgatg agaaggtgga tctctggagc cttggagttc     1560
tttgctatga attttttagtt gggaagcctc cttttgaggc aaacacatac caagagacct     1620
acaaaagaat atcacgggtt gaattcacat tccctgactt tgtaacagag ggagccaggg     1680
acctcatttc aagactgttg aagcataatc ccagccagg gccaatgctc agagaagtac      1740
ttgaacaccc ctggatcaca gcaaattcat caaaaccatc aaattgccaa aacaaagaat     1800
cagctagcaa acagtcttag gaatcgtgca gggggagaaa tccttgagcc agggctgcca     1860
tataacctga caggaacatg ctactgaagt ttattttacc attgactgct gccctcaatc     1920
tagaacgcta cacaagaaat atttgtttta ctcagcaggt gtgccttaac ctccctattc     1980
agaaagctcc acatcaataa acatgacact ctgaagtgaa agtagccacg agaattgtgc     2040
tacttatact ggttcataat ctggaggcaa ggttcgactg cagccgcccc gtcagcctgt     2100
gctaggcatg gtgtcttcac aggaggcaaa tccagagcct ggctgtgggg aaagtgacca     2160
ctctgccctg accccgatca gttaaggagc tgtgcaataa ccttcctagt acctgagtga     2220
gtgtgtaact tattgggttg gcgaagcctg gtaaagctgt tggaatgagt atgtgattct     2280 tttttaagtat gaaaataaag atatatgtac agacttgtat tttttctctg gtggcattcc     2340
tttaggaatg ctgtgtgtct gtccggcacc ccggtaggcc tgattgggtt tctagtcctc     2400
cttaaccact tatctcccat atgagagtgt gaaaaatagg aacacgtgct ctacctccat     2460
ttagggattt gcttgggata cagaagaggc catgtgtctc agagctgtta agggcttatt     2520
tttttaaaac attggagtca tagcatgtgt gtaaacttta aatatgcaaa taaataagta     2580
tctatgtcta aaaaaaaaaa aaaaa                                          2605
```

<210> SEQ ID NO 13
<211> LENGTH: 987
<212> TYPE: DNA
<213> ORGANISM: Homo sapiens

<400> SEQUENCE: 13

```
aatataagtg gaggcgtcgc gctggcgggc attcctgaag ctgacagcat tcgggccgag       60
```

-continued

```
atgtctcgct ccgtggcctt agctgtgctc gcgctactct ctctttctgg cctggaggct    120
atccagcgta ctccaaagat tcaggtttac tcacgtcatc cagcagagaa tggaaagtca    180
aatttcctga attgctatgt gtctgggttt catccatccg acattgaagt tgacttactg    240
aagaatggag agagaattga aaaagtggag cattcagact tgtctttcag caaggactgg    300
tctttctatc tcttgtacta cactgaattc accccactg aaaaagatga gtatgcctgc    360
cgtgtgaacc atgtgacttt gtcacagccc aagatagtta agtgggatcg agacatgtaa    420
gcagcatcat ggaggtttga agatgccgca tttggattgg atgaattcca aattctgctt    480
gcttgctttt taatattgat atgcttatac acttacactt tatgcacaaa atgtagggtt    540
ataataatgt taacatggac atgatcttct ttataattct actttgagtg ctgtctccat    600
gtttgatgta tctgagcagg ttgctccaca ggtagctcta ggagggctgg caacttagag    660
gtggggagca gagaattctc ttatccaaca tcaacatctt ggtcagattt gaactcttca    720
atctcttgca ctcaaagctt gttaagatag ttaagcgtgc ataagttaac ttccaattta    780
catactctgc ttagaatttg ggggaaaatt tagaaatata attgacagga ttattggaaa    840
tttgttataa tgaatgaaac attttgtcat ataagattca tatttacttc ttatacattt    900
gataaagtaa ggcatggttg tggttaatct ggtttatttt tgttccacaa gttaaataaa    960
tcataaaact tgatgtgtta tctctta                                       987
```

<210> SEQ ID NO 14
<211> LENGTH: 426
<212> TYPE: DNA
<213> ORGANISM: Homo sapiens

<400> SEQUENCE: 14

```
gactcacagc ccacagagtt ccacctgctc acaggttggc tggctcagcc aaggtggtgc     60
cctgctctga gcattcaggc caagcccatc ctgcaccatg gccaggtaca gatgctgtcg    120
cagccagagc cggagcagat attaccgcca gagacaaaga agtcgcagac gaaggaggcg    180
gagctgccag acacggagga gagccatgag gtgctgccgc cccaggtaca gaccgcgatg    240
tagaagacac taattgcaca aaatagcaca tccaccaaac tcctgcctga gaatgttacc    300
agacttcaag atcctcttgc cacatcttga aaatgccacc atccaataaa aatcaggagc    360
ctgctaagga acaatgccgc ctgtcaataa atgttgaaaa gtcatcccaa aaaaaaaaaa    420
aaaaaa                                                              426
```